US011672639B2

(12) United States Patent
Gilson et al.

(10) Patent No.: US 11,672,639 B2
(45) Date of Patent: *Jun. 13, 2023

(54) VASCULAR FILTER SYSTEM

(71) Applicant: Novate Medical Limited, Dublin (IE)

(72) Inventors: Paul Gilson, Galway (IE); Steven Horan, Galway (IE); Karl Keating, Galway (IE); Dara Finneran, County Roscommon (IE); Jacqueline O'Gorman, County Clare (IE); Damien Ryan, Galway (IE); Megan Macdonagh, County Galway (IE); Paul Bateman, Esher (GB)

(73) Assignee: Novate Medical Limited, Galway (IE)

(*) Notice: Subject to any disclaimer, the term of this patent is extended or adjusted under 35 U.S.C. 154(b) by 420 days.

This patent is subject to a terminal disclaimer.

(21) Appl. No.: 16/866,238

(22) Filed: May 4, 2020

(65) Prior Publication Data
US 2020/0261203 A1    Aug. 20, 2020

Related U.S. Application Data

(63) Continuation of application No. 14/774,576, filed as application No. PCT/EP2014/054822 on Mar. 12, 2014, now Pat. No. 10,687,930.

(Continued)

(51) Int. Cl.
*A61F 2/01*      (2006.01)

(52) U.S. Cl.
CPC .......... *A61F 2/01* (2013.01); *A61F 2002/016* (2013.01); *A61F 2002/018* (2013.01);
(Continued)

(58) Field of Classification Search
CPC ...... A61F 2/01; A61F 2/82; A61F 2/95; A61F 2002/016; A61F 2002/0075; A61F 2250/0059
See application file for complete search history.

(56) References Cited

U.S. PATENT DOCUMENTS

| | | |
|---|---|---|
| 5,344,427 A | 9/1994 | Cottenceau et al. |
| 5,375,612 A | 12/1994 | Cottenceau et al. |

(Continued)

FOREIGN PATENT DOCUMENTS

| | | |
|---|---|---|
| DE | 4030998 A1 | 4/1991 |
| DE | 102008031299 A1 | 1/2010 |

(Continued)

OTHER PUBLICATIONS

International Search Report dated Dec. 22, 2014, in corresponding International PCT Application No. PCT/EP2014/054822, filed on Mar. 12, 2014 (7 pages).

(Continued)

*Primary Examiner* — Sarah W Aleman
(74) *Attorney, Agent, or Firm* — Seager, Tufte & Wickhem LLP

(57) ABSTRACT

A vascular filter device (1) has a support (2) for engaging the wall of a blood vessel. A filter has filter elements (5) having proximal segments (10) connected to the support (3) and distal segments at least temporarily restrained at a distal apex (7) by a holder when in a filtering closed position. At least one filter element (5) extends radially outwardly with respect to a device longitudinal axis when unconstrained. The filter element may extend in a curve with a concave portion facing radially outwardly in an unconstrained configuration.

16 Claims, 72 Drawing Sheets

Related U.S. Application Data

(60) Provisional application No. 61/798,083, filed on Mar. 15, 2013.

(52) U.S. Cl.
CPC ............... *A61F 2210/0004* (2013.01); *A61F 2220/0075* (2013.01); *A61F 2230/0006* (2013.01); *A61F 2230/0067* (2013.01); *A61F 2230/0069* (2013.01); *A61F 2250/0036* (2013.01); *A61F 2250/0059* (2013.01)

(56) References Cited

U.S. PATENT DOCUMENTS

| | | |
|---|---|---|
| 5,383,887 A | 1/1995 | Nadal |
| 5,634,942 A | 6/1997 | Chevillon et al. |
| 5,725,550 A | 3/1998 | Nadal |
| 5,800,525 A | 9/1998 | Bachinski et al. |
| 5,853,420 A | 12/1998 | Chevillon et al. |
| 5,968,071 A | 10/1999 | Chevillon et al. |
| 6,193,739 B1 | 2/2001 | Chevillon et al. |
| 6,214,025 B1 | 4/2001 | Thistle et al. |
| 6,241,746 B1 | 6/2001 | Bosma et al. |
| 6,248,128 B1 | 6/2001 | Berry et al. |
| 6,267,776 B1 | 7/2001 | O'Connell |
| 6,312,461 B1 | 11/2001 | Unsworth et al. |
| 6,482,227 B1 | 11/2002 | Solovay |
| 6,517,559 B1 | 2/2003 | O'Connell |
| 6,527,962 B1 | 3/2003 | Nadal |
| 6,582,447 B1 | 6/2003 | Patel et al. |
| 6,605,111 B2 | 8/2003 | Bose et al. |
| 6,652,558 B2 | 11/2003 | Patel et al. |
| 6,666,882 B1 | 12/2003 | Bose et al. |
| 6,669,721 B1 | 12/2003 | Bose et al. |
| 6,852,076 B2 | 2/2005 | Nikolic et al. |
| 6,881,218 B2 | 4/2005 | Beyer et al. |
| 6,932,832 B2 | 8/2005 | Patel et al. |
| 6,966,923 B2 | 11/2005 | Gittings |
| 6,972,025 B2 | 12/2005 | WasDyke |
| 7,001,424 B2 | 2/2006 | Patel et al. |
| 7,094,248 B2 | 8/2006 | Bachinski et al. |
| 7,261,731 B2 | 8/2007 | Patel et al. |
| 7,279,007 B2 | 10/2007 | Nikolic et al. |
| 7,534,251 B2 | 5/2009 | WasDyke |
| 3,057,507 A1 | 11/2011 | Horan et al. |
| 8,162,970 B2 | 4/2012 | Gilson et al. |
| 8,647,360 B2 | 2/2014 | Gilson et al. |
| 8,668,713 B2 | 3/2014 | Horan et al. |
| 8,821,530 B2 | 9/2014 | Horan et al. |
| 2001/0044652 A1 | 11/2001 | Moore |
| 2003/0120303 A1 | 6/2003 | Boyle et al. |
| 2003/0176888 A1 | 9/2003 | O'Connell |
| 2003/0208227 A1 | 11/2003 | Thomas |
| 2003/0208253 A1 | 11/2003 | Beyer et al. |
| 2004/0019374 A1 | 1/2004 | Hojeibane et al. |
| 2004/0220611 A1 | 11/2004 | Ogle |
| 2005/0096735 A1 | 5/2005 | Hojeibane et al. |
| 2005/0107822 A1 | 5/2005 | WasDyke |
| 2005/0222604 A1 | 10/2005 | Schaeffer |
| 2005/0234504 A1 | 10/2005 | WasDyke |
| 2006/0025852 A1 | 2/2006 | Armstrong et al. |
| 2007/0032816 A1 | 2/2007 | O'Connell et al. |
| 2007/0112372 A1 | 5/2007 | Sosnowski et al. |
| 2007/0203571 A1 | 8/2007 | Kaplan et al. |
| 2008/0188887 A1 | 8/2008 | Batiste |
| 2008/0208245 A1 | 8/2008 | Hoffman |
| 2008/0275486 A1 | 11/2008 | Dwyer et al. |
| 2010/0185227 A1 | 7/2010 | Horan et al. |
| 2010/0185229 A1 | 7/2010 | Horan et al. |
| 2010/0185230 A1 | 7/2010 | Horan et al. |
| 2010/0228281 A1 | 9/2010 | Gilson et al. |
| 2011/0137335 A1 | 6/2011 | Hallisey |
| 2012/0029552 A1 | 2/2012 | Horan et al. |
| 2012/0245620 A1 | 9/2012 | Gilson et al. |
| 2014/0207176 A1 | 7/2014 | Gilson et al. |
| 2014/0207177 A1 | 7/2014 | Horan et al. |
| 2015/0025565 A1 | 1/2015 | Horan et al. |
| 2015/0150671 A1 | 6/2015 | Gilson et al. |

FOREIGN PATENT DOCUMENTS

| | | |
|---|---|---|
| EP | 0565395 A1 | 10/1993 |
| EP | 0582493 A1 | 2/1994 |
| EP | 0598635 A1 | 5/1994 |
| EP | 0605276 A1 | 7/1994 |
| EP | 0655228 A1 | 5/1995 |
| EP | 0678284 A1 | 10/1995 |
| EP | 0737451 A1 | 10/1996 |
| EP | 0759287 A1 | 2/1997 |
| EP | 0935975 A1 | 8/1999 |
| EP | 1103233 A1 | 5/2001 |
| EP | 1258228 A1 | 11/2002 |
| EP | 1616530 A1 | 1/2006 |
| EP | 2208479 A1 | 7/2010 |
| EP | 2381893 A1 | 11/2011 |
| FR | 2718950 A1 | 10/1995 |
| FR | 2764503 A1 | 12/1998 |
| FR | 2814670 A1 | 4/2002 |
| WO | 9638101 A1 | 12/1996 |
| WO | 0012004 A1 | 3/2000 |
| WO | 0056390 A1 | 9/2000 |
| WO | 0066031 A1 | 11/2000 |
| WO | 2004016192 A2 | 2/2001 |
| WO | 0162184 A2 | 8/2001 |
| WO | 0222048 A2 | 3/2002 |
| WO | 03092537 A2 | 11/2003 |
| WO | 2006020425 A1 | 2/2006 |
| WO | 2006074163 A2 | 7/2006 |
| WO | 2006107939 A1 | 10/2006 |
| WO | 2006116636 A1 | 11/2006 |
| WO | 2008010197 A2 | 1/2008 |
| WO | 2010082187 A1 | 7/2010 |
| WO | 2012118696 A1 | 9/2012 |

OTHER PUBLICATIONS

Rogers, "Five-year Follow-up of Prophylactic Vena Cava Filters in High-Risk Trauma Patients," Archives of Surgery (now JAMA Surgery), vol. 133, No. 4, pp. 406-412, Apr. 1998, (10 pages).

DETAIL A
SCALE 10:1

VASCULAR FILTER SYSTEM

This application is a continuation of U.S. patent application Ser. No. 14/774,576, filed Sep. 10, 2015, which is a 371 of PCT/EP2014/054822 filed Mar. 12, 2014, which claims benefit of U.S. Patent Application Ser. No. 61/798,083, filed Mar. 15, 2013, all applications are hereby incorporated by reference.

INTRODUCTION

The invention relates to vascular filter devices.

EP2208279 describes a vascular filter having a support with a proximal hoop and a distal hoop interconnected by support struts. Filter elements are connected to the support and are temporarily joined at their distal ends for form an apex in a filtering position. When the filter elements are not so retained they spring back to lie genially alongside the vessel wall. Further examples are described in our prior patent specification nos. WO2008/010197, EP2208479, and EP2381893.

Many currently available devices are variations of a conical filter design that are permanent, retrievable or temporary. The present invention relates to convertible filters which are an advancement of retrievable and temporary filters. Permanent filters are indicated for long term use where the patient has an indefinite or long term risk of pulmonary embolism while also being contraindicated to anti-coagulant medication. Retrievable, temporary, and convertible filters are indicated for short term use where the patient has an acute risk of pulmonary embolism. It is well known that permanent filters cause thrombosis of the vena cava after two or more years of use while a large number of patients only require filtration for a shorter period of time.

Retrievable filters are most effective when removed after a relatively short time period of 14 days, after which endothelial growth serves to provide enhanced adhesion to the vessel wall. With enhanced adhesion, the risk of vessel trauma at the vessel wall increases during retrieval of the filter and may cause thrombosis or perforation of the vessel wall. Most retrievable devices are of a teepee construction comprising a number of filter legs extending upstream from a central apex and are prone to tilting as they have limited longitudinal support. Other variations include a design where a conical filter is supported caudally with an annular ring; such an arrangement is also prone to tilting as it has limited longitudinal support. This understanding is supported in clinical literature; reference Rogers, F. B., et al., Five-year follow-up of prophylactic vena cava filters in high-risk trauma patients. Arch Surg, 1998. 133(4): p. 406-11; discussion 412. Upon advancement from a femoral approach, vascular geometry forces the delivery catheter tip against the wall of the vena cava. During deployment, the apex of the conical filter is released first and is free to point into or along the vessel wall (i.e. the filter is in a tilted position during deployment).

The filter does not expand until its most caudal end is released from the catheter. This instantaneous expansion causes the filter to assume the tilted position of the delivery catheter. Tilted filters present a risk of inability to retrieve as the apex or hook becomes embedded in the vessel wall. This negates the benefit of retrievable devices intended to mitigate against thrombosis after two years for patients that present an acute risk of pulmonary embolism.

Temporary filters are attached to a catheter that can be accessed externally from the patient. This reduces the risk of vessel trauma during removal and allows the filters to be in place for longer time periods; however, infection complications are known to occur frequently and the presence of a catheter extending from the vena cava to an external location is cumbersome.

Convertible filters have the ability to move to an open position at the end of a short term filtration time period dictated by the switching mechanism which allows the filter to change from the thrombus-capturing position to the non-filtering open position. Known switching mechanisms for convertible filter devices comprising biostable filter elements include biodegradable and mechanical holder members that prevent the filter elements from moving to a biased open position until elapse of the filtering period of time. Examples of such switching mechanisms are described in WO2010/082187.

However there is a risk that endothelial growth during filtering may restrict the extent of outward radial movement of the filter elements when the filter opens. This may cause the filter elements to extend partially into the blood flow in the vessel. This presents the risk of thrombosis similar to permanent filters, a risk that convertible filters are intended to mitigate.

Further, there is a risk that fibrin and/or thrombus formation at the apex may further restrict the filter from opening when presented in combination with endothelial growth and may leave the filter fully or partially closed.

The invention is directed towards reducing this risk.

SUMMARY OF THE INVENTION

According to the invention, there is provided a vascular filter device comprising: [0012] a support for engaging the wall of a blood vessel; [0013] a filter supported on the support and comprising filter elements having proximal segments connected to the support and distal segments at least temporarily restrained at a distal apex when the filter elements are across at least part of the cross-section of a vessel when in a filtering closed position, [0014] wherein at least one filter element extends radially outwardly with respect to a device longitudinal axis when unconstrained.

In another aspect, the invention provides a vascular filter device comprising a support for engaging the wall of a blood vessel, at least one filter element extending radially outwardly in an unconstrained configuration, the filter element being at least temporarily restrained across at least part of the cross-section of a vessel in a filtering closed position.

In another embodiment, the filter element extends in a curve with a concave portion facing radially outwardly in an unconstrained configuration. In one embodiment, the filter element is V-shaped with two ends connected to the support frame. In one embodiment, the filter element is Y-shaped with two ends connected to the support frame.

In another embodiment, the circumferential width of the filter element varies along its length. In one embodiment, the filter elements are held in the filtering closed position by a holder. In one embodiment, the holder is biodegradable. In another embodiment, the holder is flexible such that it is slack when in a compressed delivery configuration and wherein the holder is taut and forms a planar structure in the filtering closed position. In one embodiment, the filter element is prevented from applying a force on the holder in the compressed delivery profile, and wherein the filter element is restrained from moving to the filtering open position by the holder when in the filtering closed position, thereby resulting in the holder changing from a slack state to a taut state.

In one embodiment, the holder is rigid and compressible. In another embodiment, the distal segment extends radially outwardly at an angle to the proximal segment. In one embodiment, based on a datum of the direction from proximal to distal along the longitudinal axis as being 0.degree., when unconstrained, the distal segment extends radially outwardly at an angle of between 1.degree. and 90.degree., more preferably between 5 and 60.degree., even more preferably between 10.degree. and 45.degree. relative to the longitudinal axis of the device.

In another embodiment, based on a datum of the direction from proximal to distal along the longitudinal axis as being 0.degree., the proximal segment extends at an angle of between 60.degree. radially inwardly and 60.degree. radially outwardly, and preferably between 45.degree. radially inwardly and 45.degree. radially outwardly, and more preferably between 15.degree. radially inwardly to 15.degree. radially outwardly, and wherein the combined proximal and the distal segments extend radially outwardly.

In one embodiment, at least another filter element includes at least one articulation to vary the stiffness of the filter element along its length.

In another embodiment, at least one filter element includes a portion with a reduced circumferential width radially outwardly relative to the same portion radially inwardly.

In another embodiment, the distal segment of at least one filter element is twisted axially in the filtering closed position such that a thinner portion of the filter element faces radially outwardly and changes to face circumferentially or radially inwardly when the device changes to a filtering open position.

Preferably, V-shaped or Y-shaped filter elements are constructed with a radius where filter element members merge. In another embodiment, the radius is between 0.5 and 10 mm, more preferably between 1 mm and 5 mm, even more preferably between 2 mm and 4 mm.

In one embodiment, the filter elements include a reception space at their distal ends to receive a holder.

In another embodiment, the reception space is an eyelet.

In one embodiment, the support includes a proximal support hoop, a distal support hoop, and connector struts extending between the proximal and distal support hoops.

In another embodiment, the proximal and distal hoops include between 2 and 12 proximal and distal peaks and wherein the number of filter elements is between 1 and 16, more preferably between 2 and 12, even more preferably between 4 and 8.

In one embodiment, the distal segment of at least one filter element extends radially inwardly relative to the proximal segment.

In another embodiment, the distal segments of the filter elements extend distally towards a central apex such that a conical reception space is provided in the centre of the lumen for reception of blood clots. In one embodiment, the distal segment of the filter elements extend proximally towards a central apex such that an annular reception space is provided at the vessel wall for reception of blood clots.

In a further aspect, the invention provides a vascular filter device as claimed in any preceding claim comprising: a support for engaging the wall of a blood vessel; at least one filter element with a proximal segment with a length of less than 10 mm and preferably less than 7 mm and a distal segment and being arranged to be temporarily restrained in a filtering closed position across at least part of the cross-section of a vessel; the filter element extending radially outwardly when unconstrained, wherein the filter element is configured so that, when unconstrained, the proximal segment has an angle with respect to the longitudinal axis of between 45.degree. radially inwardly and 45.degree. radially outwardly.

In another embodiment, the support comprises struts extending approximately parallel to the device longitudinal axis, and at least one of the filter elements is connected to the support at a strut.

In one embodiment, at least one filter element comprises two or more arms each having a proximal segment connected to the support and a distal segment connected to at least one other arm.

In another embodiment, at least one filter element comprises an intermediate segment between the proximal and distal segments, said segments being delimited by bends turning the element outwardly to a greater angle with respect to the device longitudinal axis.

In another embodiment, at least one filter element comprises an arm with a cross-sectional shape which is progressively wider in the radial inward direction.

In one embodiment, the arm has a tapered shape. In one embodiment, the arm has a curved outer surface.

In another embodiment, the support comprises a hoop configured to press against a vessel wall. In one embodiment, the support comprises a proximal hoop and a distal hoop interconnected by struts.

In another embodiment, the support and at least one filter element are configured so that the filter element has at its distal segment a radial outward force in the range of 0.1 N to 1.0 N where the device unconstrained diameter is in the range of 20 mm to 40 mm.

In another embodiment, the support and at least one filter element are configured so that the filter element has at its distal segment a radial outward force in the range of 0.1 N to 0.4 N where the device unconstrained diameter is in the range of 25 mm to 35 mm.

In one embodiment, at least one filter element has a length in the range of 15 mm to 30 mm, and more preferably 17 mm to 23 mm. In one embodiment, the distal segment extends at an angle of under 90.degree., preferably under 50.degree., and more preferably between 10.degree. and 30.degree. with respect to the device longitudinal axis, radially outwardly when unconstrained.

In another embodiment, the distal segment length is in the range from 10 mm to 40 mm, more preferably from 15 to 30 mm, and even more preferably from 17 to 25 mm.

In one embodiment, the proximal segment length is in the range of 2 mm to 20 mm, more preferably from 3 mm to 15 mm, and even more preferably from 5 mm to 10 mm.

In another embodiment, the filter element is configured so that a transitional part of a filter element, between the proximal and the distal segments, protrudes radially inwardly when lying against a blood vessel wall. In another embodiment, the distal segment has a smaller cross-sectional area than the remainder of the filter element sufficient to provide additional flexibility for the distal segment that would allow a distal extremity or eyelet to conform to the vessel wall.

In another embodiment, at least one filter element is formed with articulations at different locations along the length of the filter element, said articulations providing flexibility for the filter element along its length so that the filter element can conform to irregular vessel shapes and so that if minimal endothelial growth has occurred, the distal end will bend radially inwardly in order to reduce the risk of perforation of the vessel wall with the distal extremity.

In another embodiment, the articulations are laser cut into at least one filter element material when cutting the device from raw tubing and before expanding and heat setting.

In another embodiment, the filter elements have sufficient radial outward force to open even if there is endothelial growth acting to constrain the filter element.

In one embodiment, at least one filter element has attributes including at least one of a length less than 25 mm, a decreasing wall thickness towards the filter element extremity, and a decreasing filter element width in the radial direction.

In another embodiment, the device comprises a hook to facilitate retrieval.

In another embodiment, the device comprises a curved spring support frame with a plurality of proximal peaks and distal peaks.

In one embodiment, the device is adapted to facilitate placement of a second filter at a later stage without the need to overlap support frames. In another embodiment, at least some filter elements comprise extensions extending proximally. In one embodiment, the support comprises proximal and distal support hoops and the extensions extend from proximal peaks of a distal support hoop.

In another embodiment, the device comprises filter springs that extend between the filter extensions and filter elements which are collapsible. In one embodiment, at least some of the filter elements are helical.

In another embodiment, at least some filter elements extend between proximal and distal supports in the open configuration with eyelets positioned approximately half way along the filter elements.

In one embodiment, the device comprises a distal support hoop which is twisted so that terminations of helical filter elements move closer together and form a central apex where they are held in place. In another embodiment, the terminations have eyelets.

In one embodiment, at least some filter elements have different lengths such that their ends are staggered to form a lumen for insertion of a holder member.

In one embodiment, at least some filter elements have one end slidably attached to connector struts and with the other end fixed, to form a double cone filter. In another embodiment, the device comprises secondary filter elements attached to the proximal ends of the filter elements, forming a proximal apex and the distal ends of the secondary filter elements are slidably attached to the support.

In one embodiment, at least some filter elements are spring-like and extend between the support and an apex such that upon conversion, the springs apply a radially outward force to the apex.

In another embodiment, at least some of the filter elements have barbs that are bent out of plane such that they extend radially inwardly during filtering and being configured to retain a clot after conversion.

In one embodiment, at least some of the filter elements extend distally towards a central apex from the support, and filter element terminations are positioned proximally of the proximal ends of the filter elements at a central apex.

In another embodiment, the filter elements are restrained by a holder and at least some filter elements extend past the position of the holder.

In another embodiment, at least some filter elements are twisted about a longitudinal axis such that the filter element applies a torsional force upon opening.

In one embodiment, the support comprises proximal and distal support hoops and wherein helical or stepped connector struts extend between distal peaks of a proximal support hoop and proximal peaks of a distal support hoop that are offset from each other.

In one embodiment, at least some filter elements extend towards an apex in a spiral.

In another embodiment, at least some filter elements include springs such the filter element shortens when moving from the filtering closed position to the filtering open position.

In one embodiment, the support comprises proximal and distal coils joined by a central bridge between the distal end of the proximal coil and the proximal end of a distal coil and a longitudinal strut between the proximal and distal ends of the proximal and distal coils respectively. In another embodiment, the central peak is wound radially inwardly to form a filtering configuration wherein the device is prevented from unwinding by a holder extending through openings in the coils wherein a stop feature is provided proximally of at least one coil for the proximal coil and distally of at least one coil for the distal coil. In another embodiment, the holder is biodegradable. In one embodiment, the device includes a hook for retrieval.

In another embodiment, the filter elements include openings proximal to their distal ends such that when held together by a holder, the distal ends are bent radially outwardly relative to the filter elements thereby storing energy that will be released upon opening to aid in retraction to the vessel wall. In another embodiment, a filter holder is shaped with a conical or bull nose pointing proximally for improved flow dynamics.

In another embodiment, in a compressed hoop is included at the ends of the filter elements forming a filter apex such that upon conversion, the hoop radially expands applying a force to move the filter elements radially outwardly to press against the vessel wall.

In one embodiment, the filter elements are detachable from the support frame. In one embodiment, the filter apex includes hooks for reception of a snare to facilitate retrieval using a retrieval catheter.

In another embodiment, the filter is connected to the support by a releasable connector so that the device can be left in place to open passively or the filter can be selectively removed by way of a second intervention.

In another embodiment, at least some filter elements extend towards a filter apex in a wave pattern. In one embodiment, at least some filter elements extend towards a filter apex and include struts extending from the filter elements.

In another embodiment, at least some filter elements extend towards a filter apex and include members forming one or more filtering cells.

In another embodiment, at least one filter element extends radially outwardly in a non-planar path.

In another embodiment, at least part of a filter element is narrower in the circumferential direction with a sharpened section to achieve less resistance to break through thrombus.

In another embodiment, the holder comprises a filament engaging the filter element distal segments in a manner whereby at least some filter element distal segments are spaced-apart in the circumferential direction.

In one embodiment, the holder forms a passageway for blood flow between the filter element distal segments. In one embodiment, the holder filament is trained through eyelets in at least some filter element distal segments. In one embodiment, the holder filament forms a plurality of loops by being trained through the eyelets at least twice. In one embodiment, the holder filament is tied in a knot onto one filter element.

In another embodiment, one or both ends of the filament is tied in an individual knot, each said knot preventing the filament from being pulled through a filter element eyelet. In one embodiment, the holder comprises a loop and a filament extending across the loop.

In another embodiment, the loop is formed by a first filament and a second filament of smaller cross-sectional area extends across the loop.

In another embodiment, the holder comprises a plurality of filaments or filament segments each restraining a sub-set of the filter elements.

In one embodiment, the holder restrains each of a plurality of subsets of filter element distal segments in a group.

In another aspect, the invention provides a vascular filter device comprising: [0083] a support for engaging the wall of a blood vessel; [0084] a filter supported on the support and comprising filter elements having proximal segments connected to the support and distal segments at least temporarily restrained by a holder at a distal apex when the filter elements are across at least part of the cross-section of a vessel when in a filtering closed position, and [0085] wherein the holder comprises a filament which engages the filter element distal segments in a manner whereby at least some of said filter element distal segments are spaced-apart in the circumferential direction.

DETAILED DESCRIPTION OF THE INVENTION

Brief Description of the Drawings

The invention will be more clearly understood from the following description of some embodiments thereof, given by way of example only with reference to the accompanying drawings in which:—

FIG. 22 is an oblique view of the device unconstrained and FIG. 23 shows plan, elevation, and end views of the device unconstrained. FIGS. 24 and 25 show the device in a filtering configuration with endothelial growth. FIG. 26 and FIG. 27 depict the device post conversion and illustrate the wedging effect of endothelial growth formation between the filter elements and connector struts;

DESCRIPTION OF THE EMBODIMENTS

In various embodiments a filter device of the invention has a support for engaging a blood vessel wall and a filter supported on the support. The filter device may be formed from a laser cut NiTi or other shape memory alloy tube by expanding and constraining the filter in a fixture or on a mandrel and then performing a heat treatment step to set the new shape. This method is referred to here as "shape setting". The filter can then be crimped down to a diameter that is greater than, equal to, or less than that of the raw tube and loaded into a delivery sheath for low profile delivery to the implant site. When deployed into an environment that is above the Af temperature, the filter will revert to its expanded form provided by the shape-setting step (for example, if the material's Af temperature is 20.degree. C., it will revert to its shape set form in an environment that is above 20.degree. C. such as that of blood at 37.degree. C. It is appreciated that materials without shape memory properties may alternatively be used.

In various embodiments, the filter elements can be manually formed into a shape and then heat treated (annealing) to remove stresses and strains introduced through work hardening. The preferred embodiment uses shape memory materials as they are capable of withstanding much higher strains.

In this specification the terms "proximal" and "distal" are with reference to the direction of blood flow, the proximal parts being upstream of the distal parts.

Figure 1:
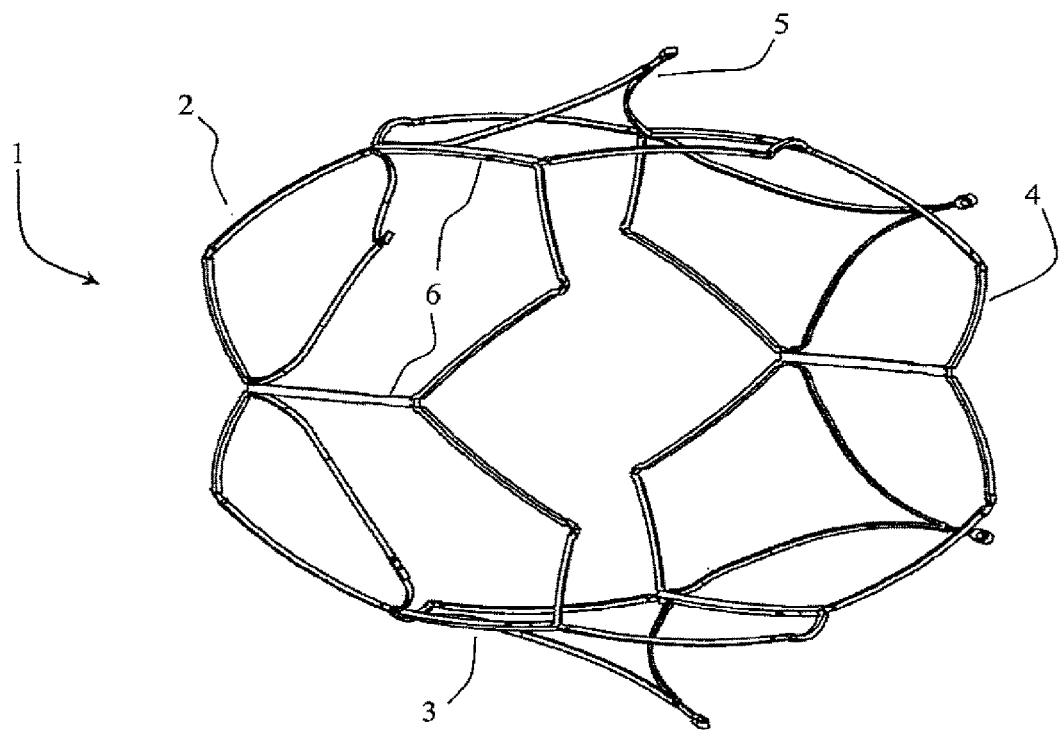
FIG. 1 is a perspective view of a vessel of the device of the invention with the filter elements unconstrained.
Figure 2:
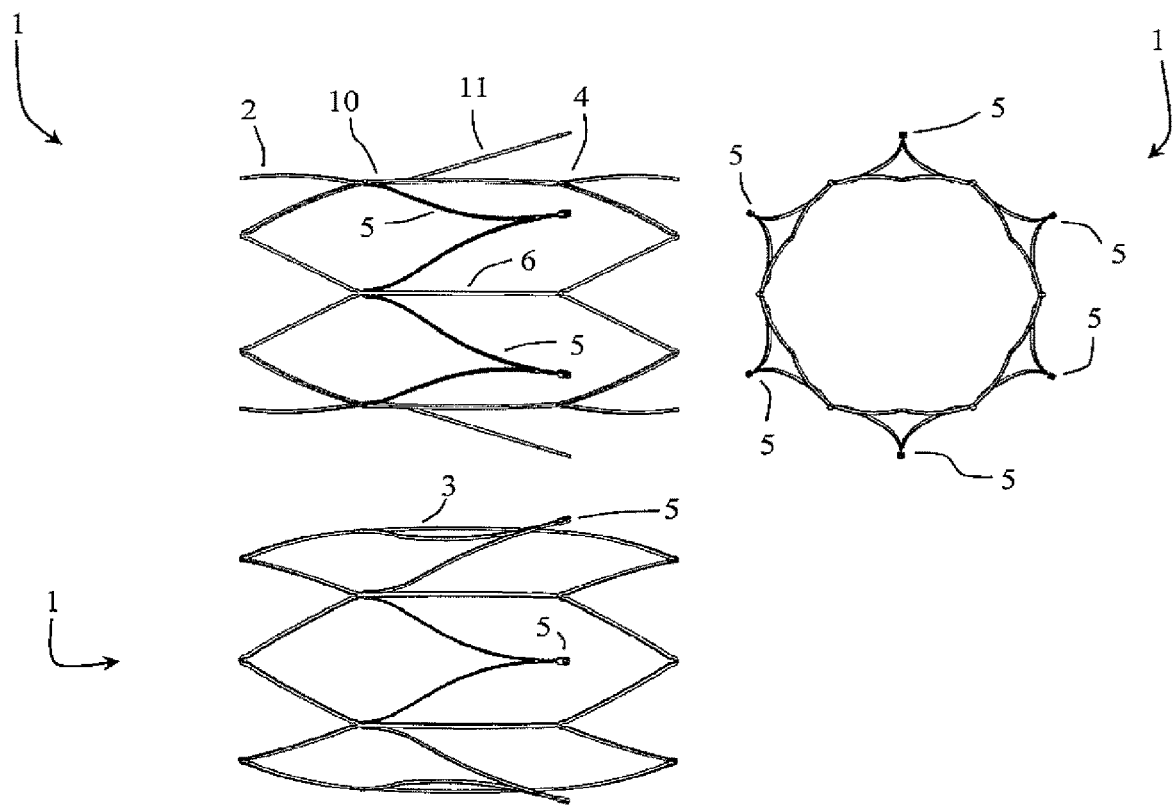
FIG. 2 is a set of views including two side views and an end view with the filter elements unconstrained.
Figure 3A:
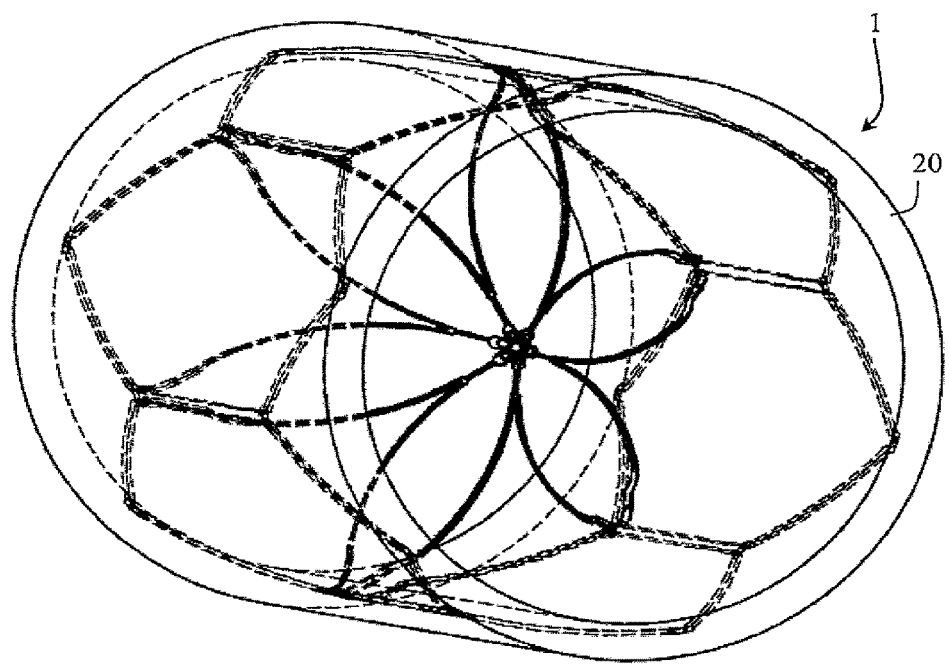
FIG. 3(a) is a perspective view.
Figure 3B:
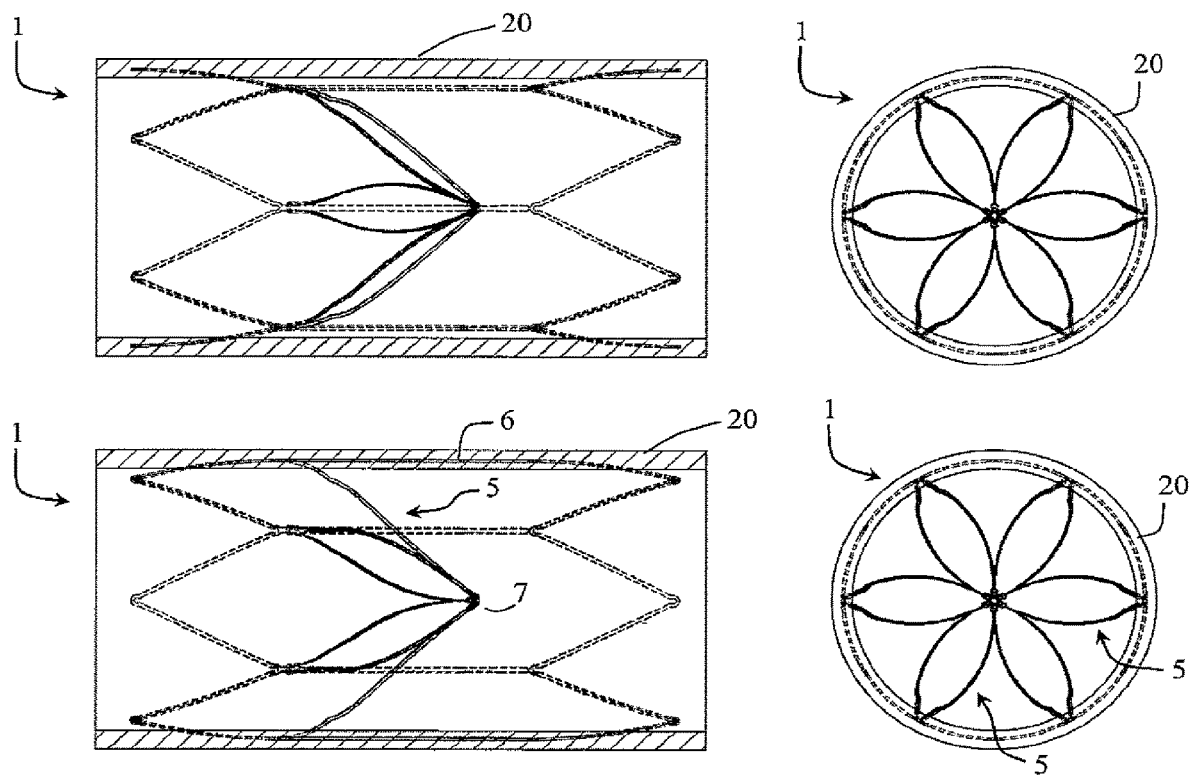
FIG. 3(b) shows pairs of side and end views of the device in use with endothelial growth during filtering.
Figure 4:
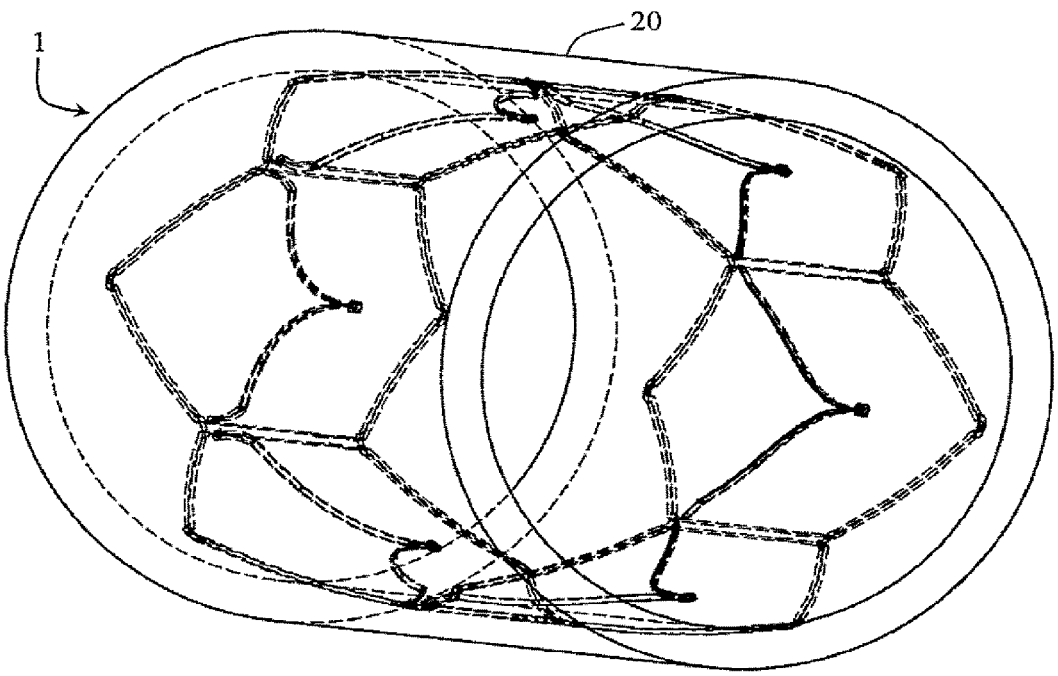
FIG. 4 is a perspective diagram illustrating use of the device shortly after the filter opens when there has been endothelial growth prior to the filter opening.
Figure 5A:
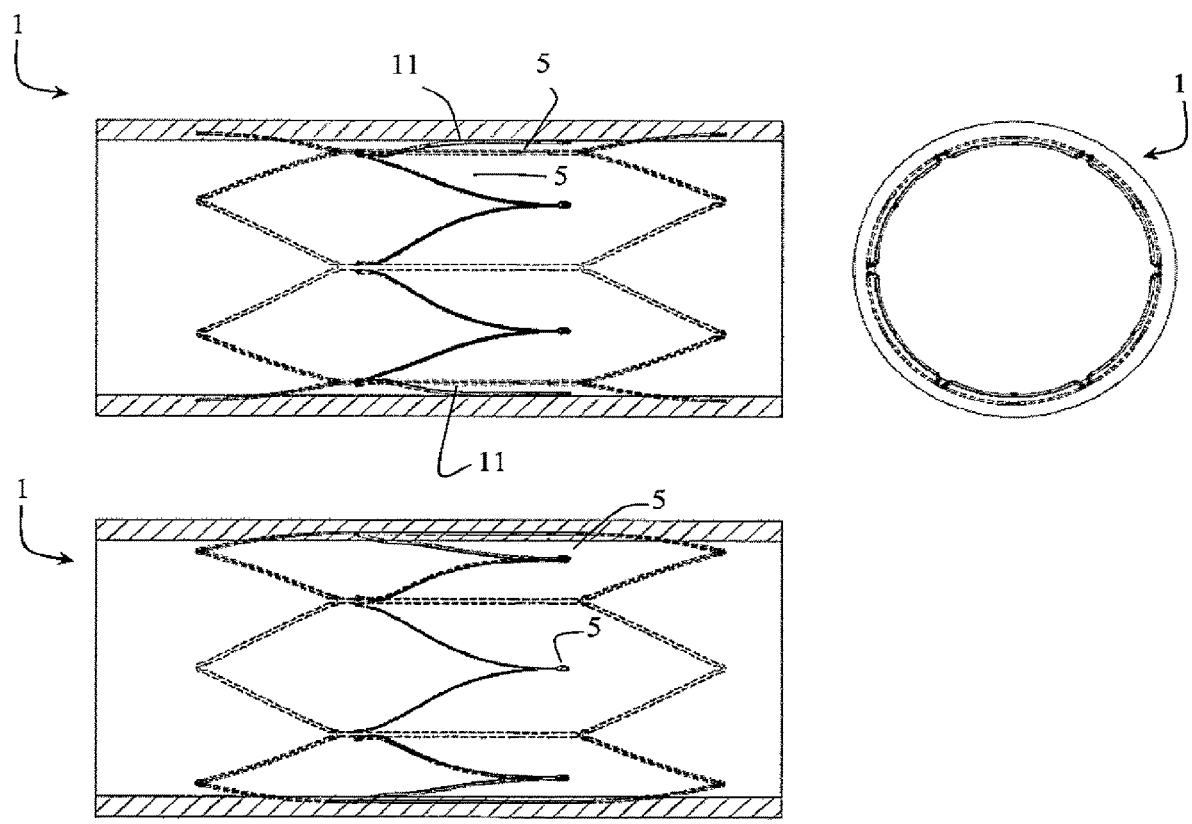
FIG. 5(a) is a pair of side views and an end view.
Figure 5B:
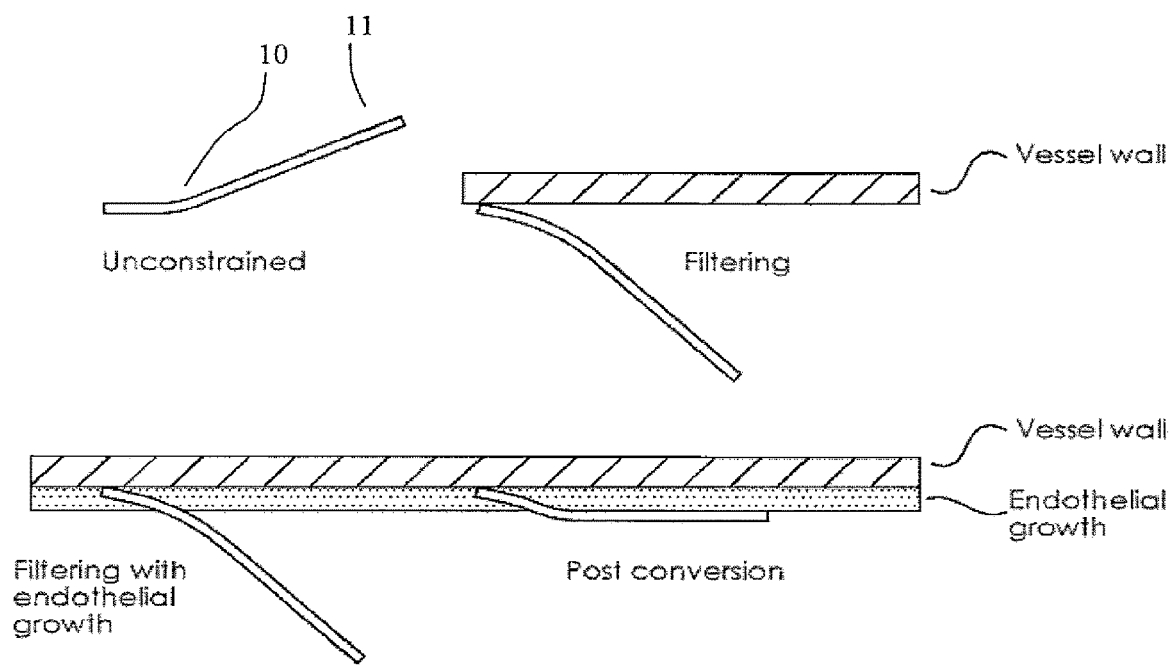
FIGS. 5(b) and 5(c) illustrate the interaction between the filter elements and the vessel wall where the filter elements are shaped with straight and curved distal segments respectively.

Referring to FIGS. 1 to 5 a vascular filter device 1 comprises a proximal support hoop 2, a longitudinal support 3, a distal support hoop 4, and filter elements 5. FIGS. 1 and 2 show the device in an unconstrained configuration during manufacturing while FIG. 3 shows the device in a filtering configuration after endothelial growth in a blood vessel. FIGS. 4 and 5 show the filter in an open state with unrestricted blood flow.

Filter elements 5 have arms each extending from struts 6 of the longitudinal support 3 and being joined at a distal apex 7 in the filtering configuration as shown in FIG. 3. Each filter element arm has a proximal segment 10 and a distal segment 11. The proximal segment 10 is joined to strut(s) 6 and is approximately parallel to the device's longitudinal axis. The distal segment 11 is splayed radially out when the distal ends of the filter elements 5 are not constrained to form the apex 7 for filtering. This is best viewed in FIG. 2.

While the proximal segment 10 is substantially parallel to the device axis, it may be at an angle of under 90.degree., preferably under 50.degree., and more preferably between 10.degree. and 30.degree. with respect to the device's axis. A larger angle will provide more radial force to assist in overcoming endothelial growth and any fibrin growth or thrombus formation at the apex if present, however, the angle must not be so high at the distal end of the filter element as to press too firmly at the vessel wall and risk perforation. A more acute angle will suffice in aiding the filter arm to conform to the vessel wall in the open configuration by negating the wedging effect of endothelial growth at the proximal ends of the filter elements while also contributing towards additional radial force at the distal peaks of the filter elements to overcome growth or thrombus formation at the apex 7. Such an acute angle will also keep the distal peaks of the filter elements more tangential with the vessel wall in the open configuration thus reducing any risk of perforation. The distal segment length contributes to the opening force at the distal peaks of the filter elements and the capture volume, a shorter length affording more opening force and less capture volume—the capture volume being the volume of the conically shaped filter basket. For a device that affords sufficient radial force to overcome endothelial growth at the vessel wall, fibrin and/or thrombin growth at the apex and sufficient capture volume in order to prevent occlusion of the vessel, the distal filter element segment length must be balanced between these attributes. Preferably, the distal segment length should range from 10 to 40 mm, more preferably from 15 to 30 mm, and even more preferably from 17 to 25 mm. The proximal segment length determines the level of endothelial growth that can be overcome with a larger length being capable of overcoming larger wall thicknesses of endothelial growth. In the filtering configuration, this segment is pulled down into the blood flow. Any endothelial growth will have a tendency to set the proximal segment in it 'filtering' position and after conversion, the distal segment will spring back to lie against the vessel wall. Refer to FIG. 5(*b*) showing how the proximal segment position is set in the filtering position post conversion when sufficient endothelial growth has occurred. Note that, there may be slight spring back of the proximal segment post conversion due to the compression of the endothelial layer; this must also be considered when forming the filter element profile. In this manner, the length of the proximal segment accounts for endothelial growth by offsetting the bending zone for the distal segment so that the distal segment is not subjected to positional fixing by the endothelial layer. The length of the proximal segment must not be set too long as this will cause the transition between the proximal and distal segments to extend into the flow post conversion. The proximal segment length should be set to overcome a clinical average for endothelial growth wall thickness while accommodating a range of thicknesses either side of this average. Preferably, the proximal segment length should range from 2 to 20 mm, more preferably from 3 to 15 mm, and even more preferably from 5 to 10 mm. FIG. 5(*c*) shows how a filter element with a curved distal section interacts with endothelial growth, the curved section allowing for compensation of variable thicknesses of endothelial growth.

The barrel shape of the support frame in the unconstrained configuration (shown in FIG. 2, previously disclosed in U.S. Pat. No. 8,057,507) and sufficient radial force provided by the proximal and distal hoops prevent the filter elements from pulling the struts 6 inwardly during filtering. This is best shown in FIG. 3(*b*) bottom side view. In order to apply less stress to the connector strut 6 and the connection between the connector strut 6 and the proximal arm segment 10, the proximal arm segment 10 and the distal arm segment 11 may be formed with a radius connecting them. Preferably, this radius is less than 10 mm and more preferably less than 5 mm, allowing the filter element to bow out with a more obtuse angle between segments 10 and 11 during filtering. The distal segment 11 may also be formed with a concave curve facing radially outwardly. This would provide a substantially straight shape for the distal segment in the filtering configuration if a slight concave curve is applied for the unconstrained configuration. If a more acute concave curve facing radially outwardly is applied for the unconstrained configuration, a less concave shape will result for the distal segment in the filtering configuration. A substantially straight or concave shape is preferred in the unconstrained configuration to ensure that the distal tips of the filter elements lie against the vessel wall post conversion. A concave shape facing radially outwardly post conversion will accommodate a wider range of thicknesses of endothelial growth—refer to FIG. 5(*c*). In contrast, a substantially straight or convex curve facing radially outwardly is preferred in the filtering configuration in order not to reduce the capture volume of the filter. A smaller radius between the proximal and distal segments in conjunction with a more acute concave curve for the distal segment in the open configuration will provide additional springback to aid in bringing the filter elements back to the vessel wall upon conversion, overcoming any endothelial growth and fibrin or thrombus that may have formed at the apex during implantation. Preferably, the distal segment will have a slightly concave curve facing radially outwardly in the unconstrained configuration.

As shown most clearly in FIG. 5, when the filter opens and the elements 5 are unconstrained the distal arm segment 11 presses into the endothelial growth resulting in unrestricted blood flow. This is by virtue of a bend between the proximal and distal segments 10 and 11 respectively and also the fact that the proximal segment 10 extends axially. The proximal segment of the filter elements accounts for the wedging effect of endothelial growth (where endothelial layer forms between connector struts 6 and proximal segment 10 having the effect of wedging the proximal segment in the position assumed after initial implantation in the filtering configuration) while the distal segment flare pushes against the vessel wall to promote endothelial encapsulation. Note that the filter elements will be covered by endothelial growth in the weeks after initial conversion.

Figure 6:
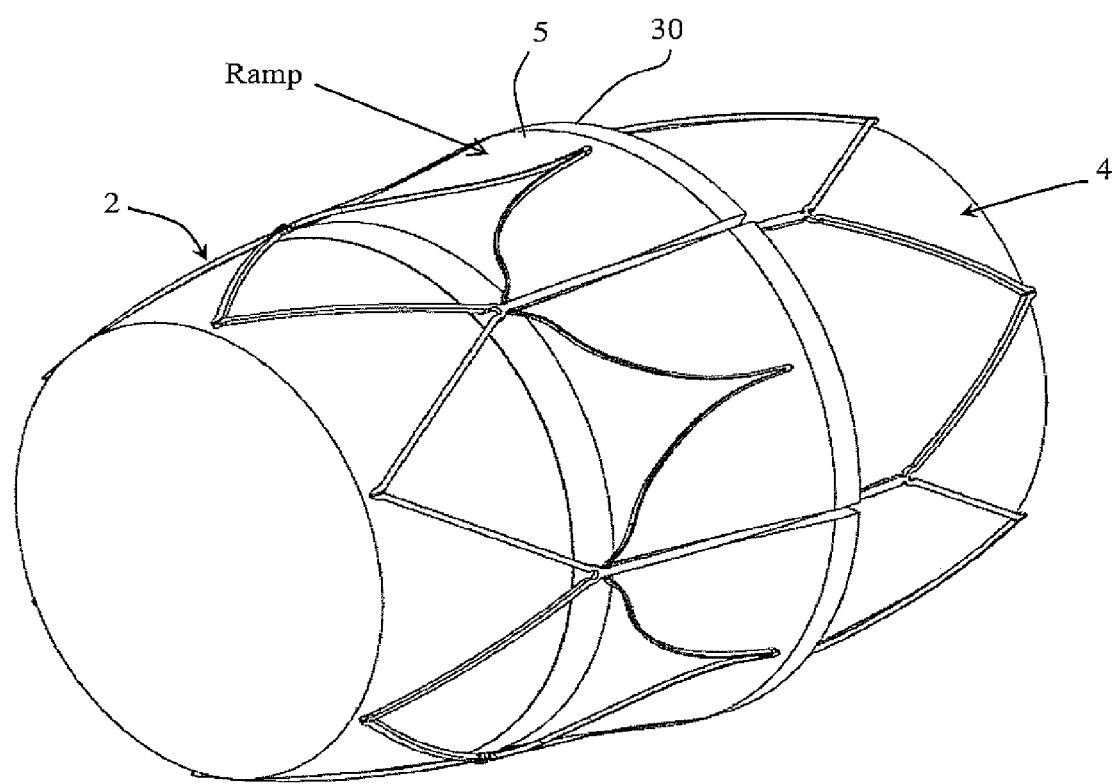
FIGS. 6 and 7 are perspective views showing use of a forming tool during production of the device.

FIG. 6 shows the filter frame on a barrel shaped forming tool 30. Ramps on the tool give the filter elements their flared shape. Pins are added to the tool in order to apply curvature to the filter element profile along the surface of the tool. Clamps may also be used to press struts against the tool if forming sharp curves.

Figure 7:
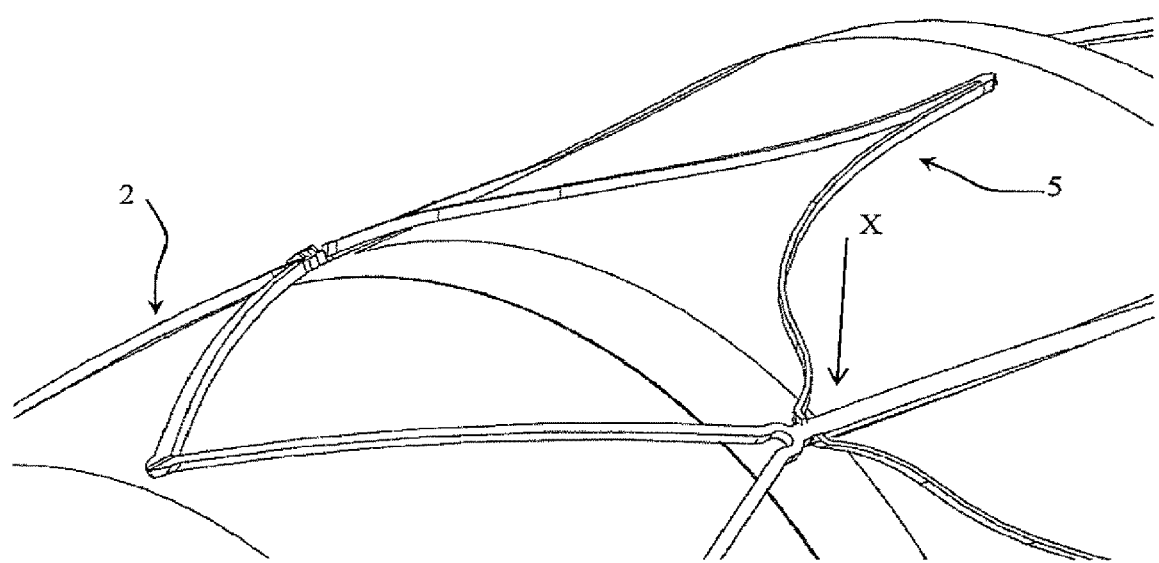

Referring to FIG. 7, as the filter element comes down the side of the barrel shape the height reduces, and when this is viewed in elevation it appears that there is a hump in the geometry.

Figure 8:
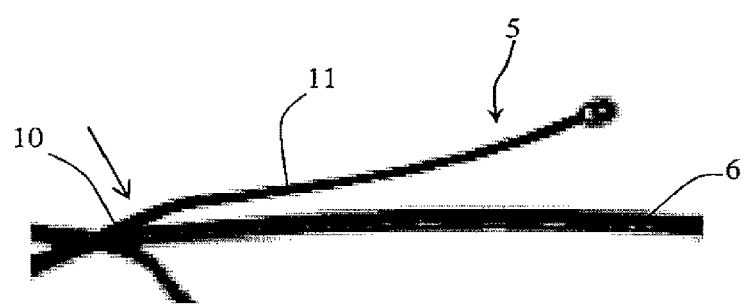
FIG. 8 shows an individual filter element profile.

FIG. 8 shows a hump or kink that is visible in the profile of the filter elements between the segments 10 and 11. This shape is due to the 3D nature of the filter—i.e. the hump is a visual effect of the circumferentially curved profile of the filter element.

Figure 9:
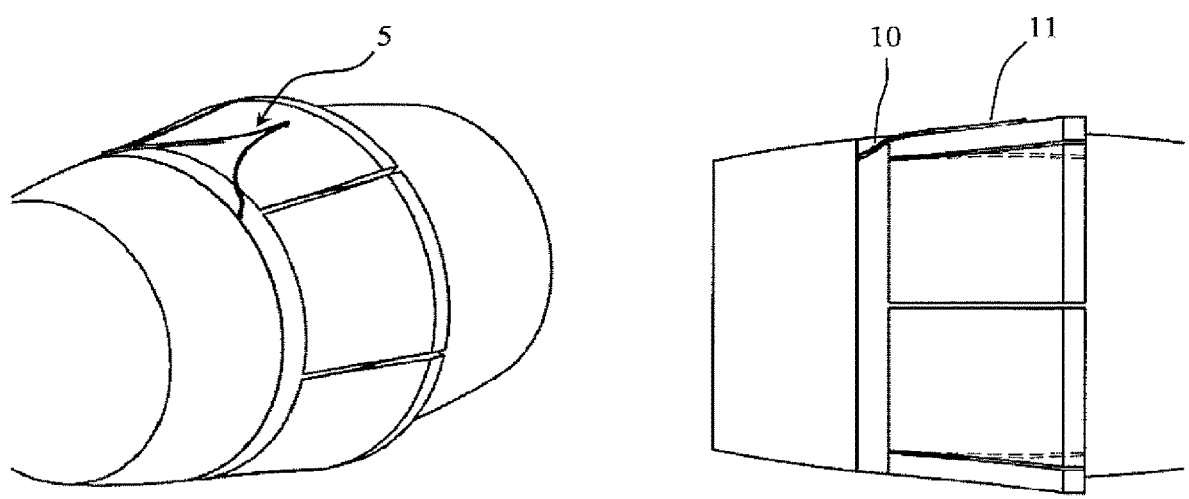
FIG. 9 shows more detail of the filter element on the forming tool.

Referring to FIG. 9, this shows a filter element on the forming tool. When the filter element 5 extends down the side of the barrel shape, a hump is visible in elevation view.

Figure 10:
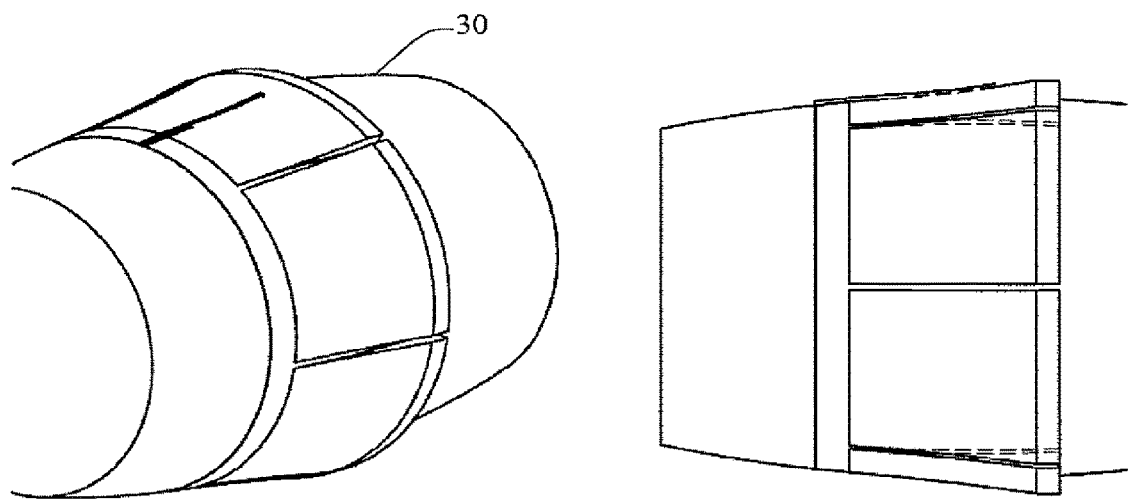
FIG. 10 is a view of a single-arm filter element that depicts how the filter element of FIGS. 6 to 9 will interact with the vessel wall.

Referring to FIG. 10, if a filter element was formed using a single arm that extends axially in the direction of the device's central axis, the hump is not visible as the filter element does not extend down the side of the barrel. This 'single arm profile' shape shown in FIG. 10 represents how the 3D V-shaped filter element contacts the vessel wall and the hump visible on the 3D element in FIG. 9 is a function of the cylindrical profile of the filter element.

Figure 11:
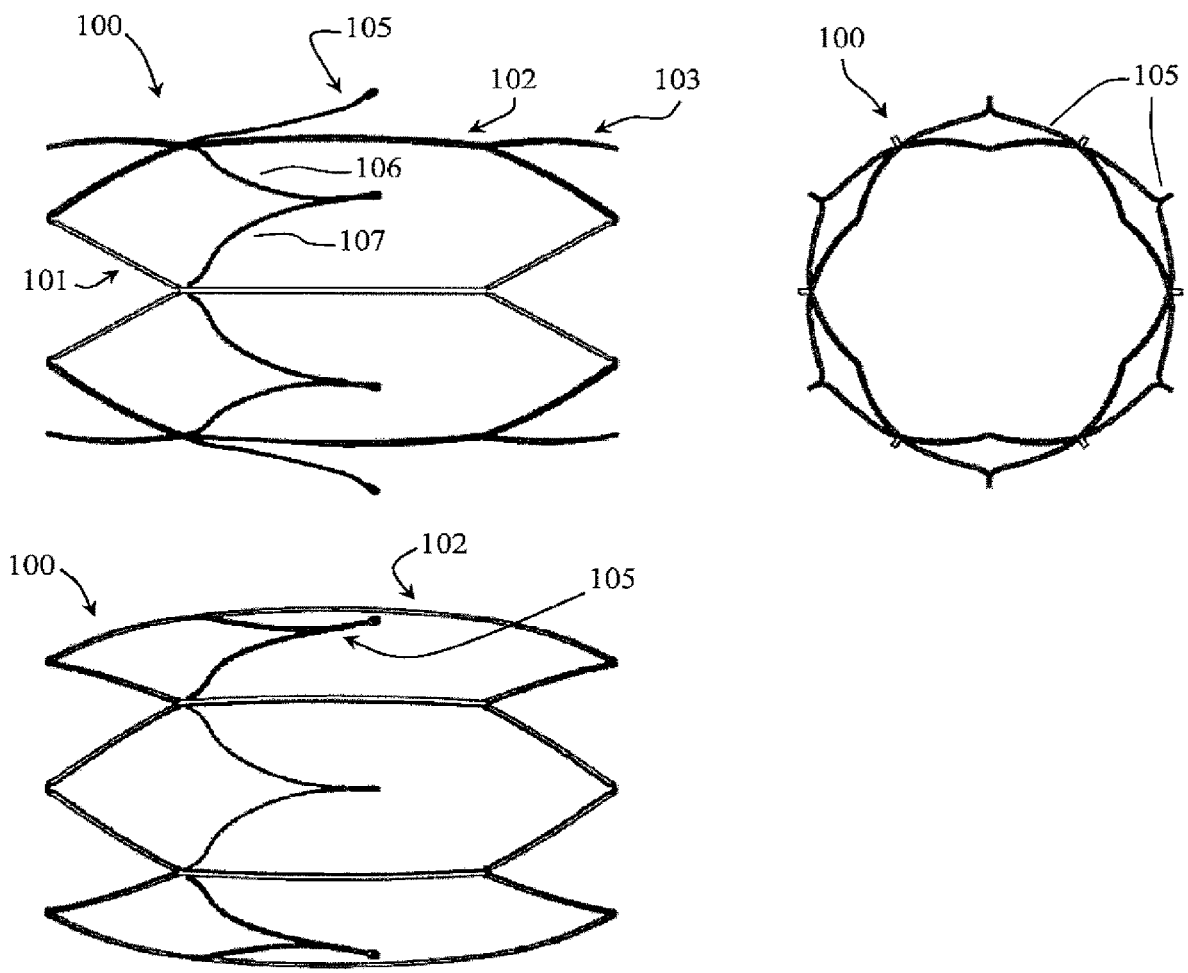
FIG. 11 is a set of two side views and an end view of another device of the invention and FIG. 12 is a view of a single-arm filter element that depicts how the filter element of FIG. 11 will interact with the vessel wall.
Figure 12:
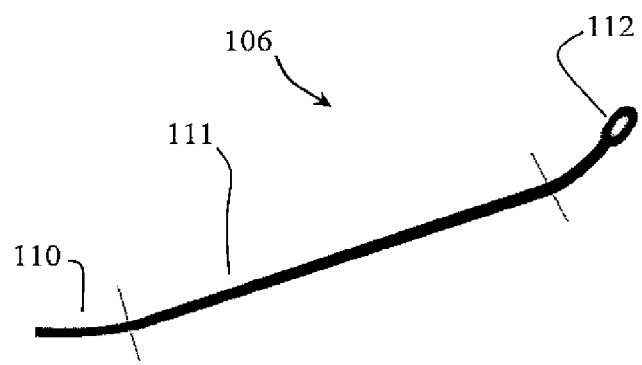
Figure 13:
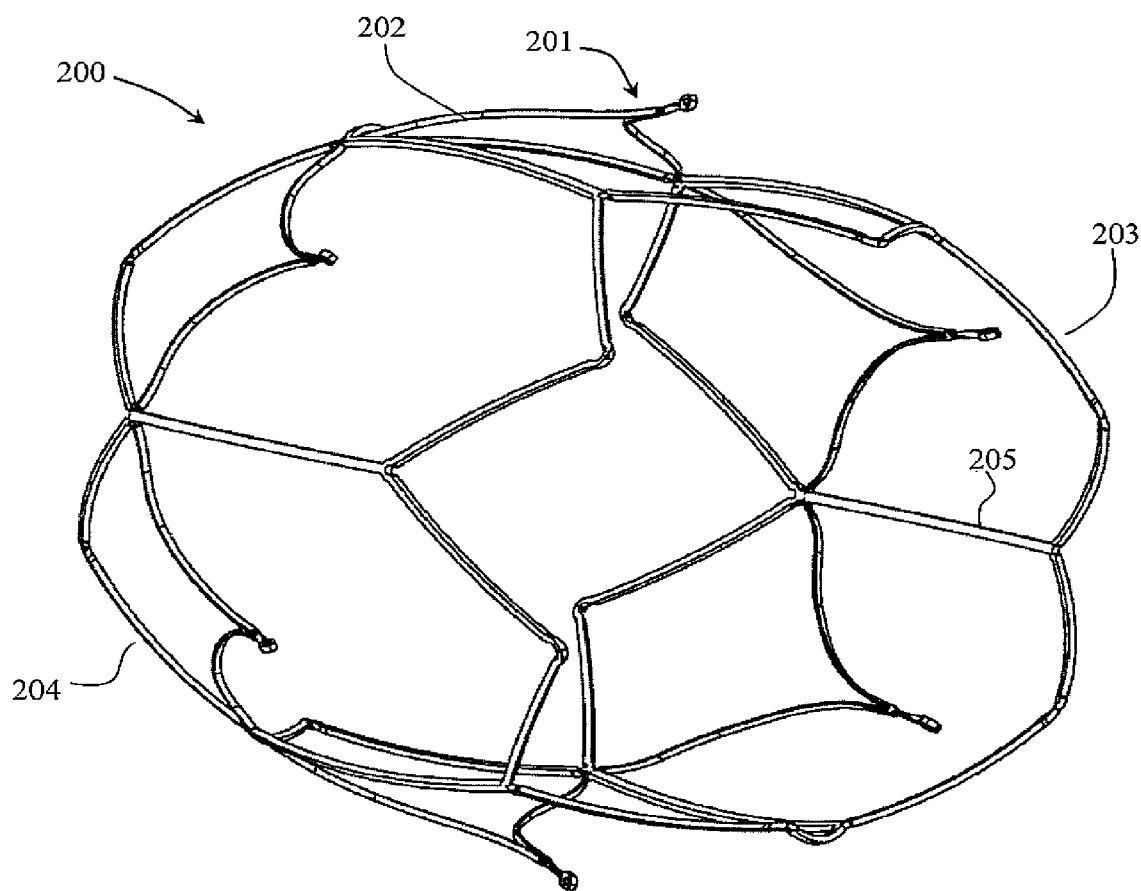
FIG. 13 is a perspective view of a further device.

Referring to FIGS. 11 and 12 an alternative device 100 has a proximal hoop 101, a distal hoop 103 and intermediate support struts 102. Filter elements 105 have arms 106 and 107 each with proximal, intermediate, and distal segments 110, 111, and 112 respectively.

The segments 110 and 112 are angled relative to the section 111. The profile shown in FIG. 12 is the 2D profile that represents how the 3D V-shaped filter element contacts the vessel wall. During conversion, the proximal segment 110 overcomes the wedging effects of endothelial growth as previously discussed for device 1 while the segment 112 ensures that the eyelet is not obstructing the vessel wall. The filter element is designed so that even if the intermediate segment 111 protrudes slightly into the blood flow, due to unforeseen wedging from endothelial growth, the distal tip will still bend radially outwardly and make contact with the vessel wall, preventing it from obstructing the blood flow further. The distal segment may be formed using a lower strut width and/or thickness than the proximal and intermediate segments 110 and 111 in order to provide additional flexibility for the distal segment that would allow the distal tip or eyelet to conform to the vessel wall and not cause perforation of the vessel. Alternatively, or in combination with the strut width and/or thickness adjustments, a radius can be supplied between the intermediate and distal segments for further flexibility enhancements. In another embodiment, the transition between the intermediate and distal segments may incorporate an s-bend or a wave pattern to enhance flexibility.

FIGS. 13 to 21 show a device 200, having the same overall architecture as the devices 1 and 100, with filter elements 201 having joined arms 202 connected to a support frame comprising a proximal hoop 204 and a distal hoop 203 and a plurality of connector struts 205 extending between the distal peaks of the proximal hoop 204 and the proximal peaks of the distal hoop 203. In this case, the filter element arm 202 is configured with a proximal straight section 206 and a distal section 207 with a continuous radius and an eyelet 208. Alternatively, the filter arm may be supplied with one continuous radius and no proximal straight section.

Figure 5C:
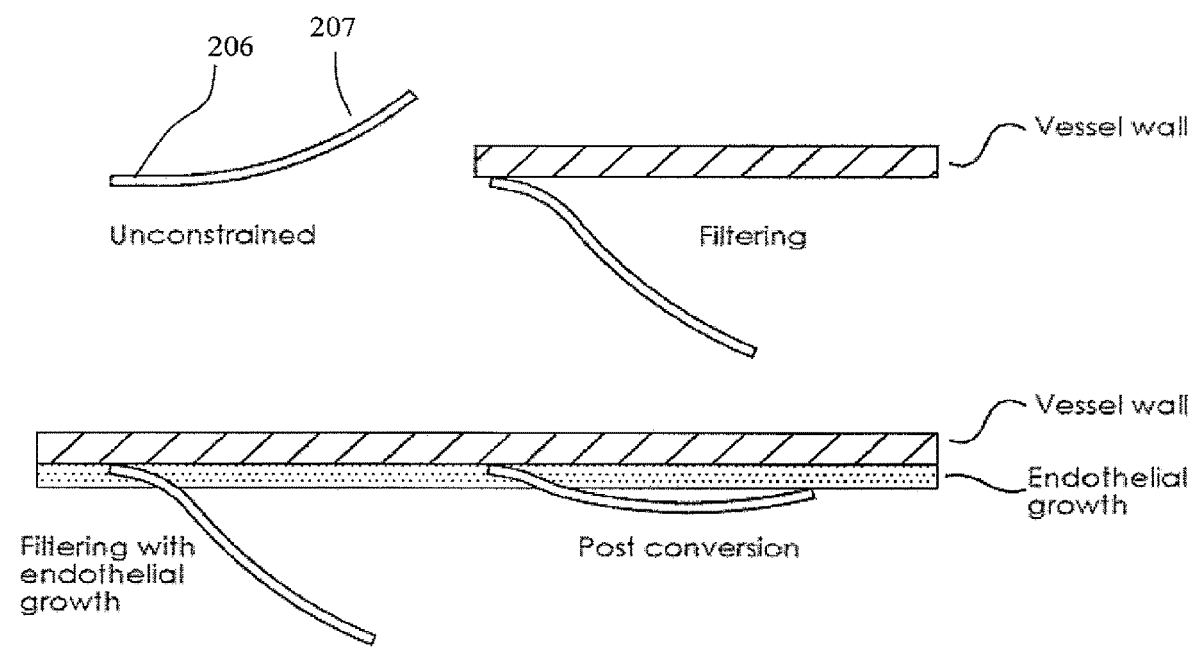
Figure 14:
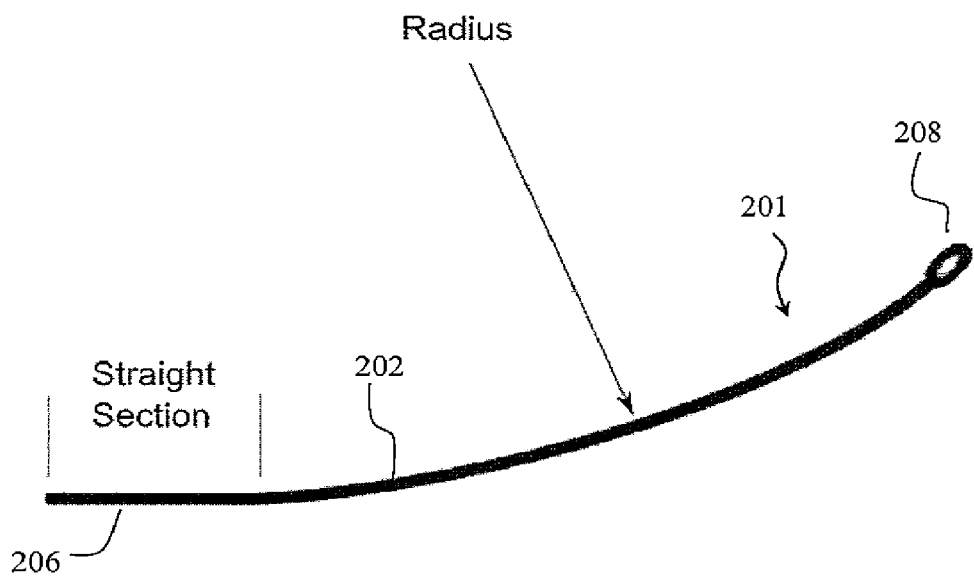
FIG. 14 is a view of a single-arm filter element that depicts how the filter element of FIG. 13 and FIGS. 15 to 16 will interact with the vessel wall.

The profile shown in FIG. 14 is the 2D profile that represents how the 3D V-shaped filter element contacts the vessel wall when in use. As with devices 1 and 100, the proximal section offsets the bending location for the distal section, the distal section being formed so that the eyelet extends radially outwardly in the open configuration post conversion in the presence of endothelial growth. The concave curved profile of the distal section 207 accommodates for various thicknesses of endothelial growth as shown in FIG. 5(c).

Figure 15:
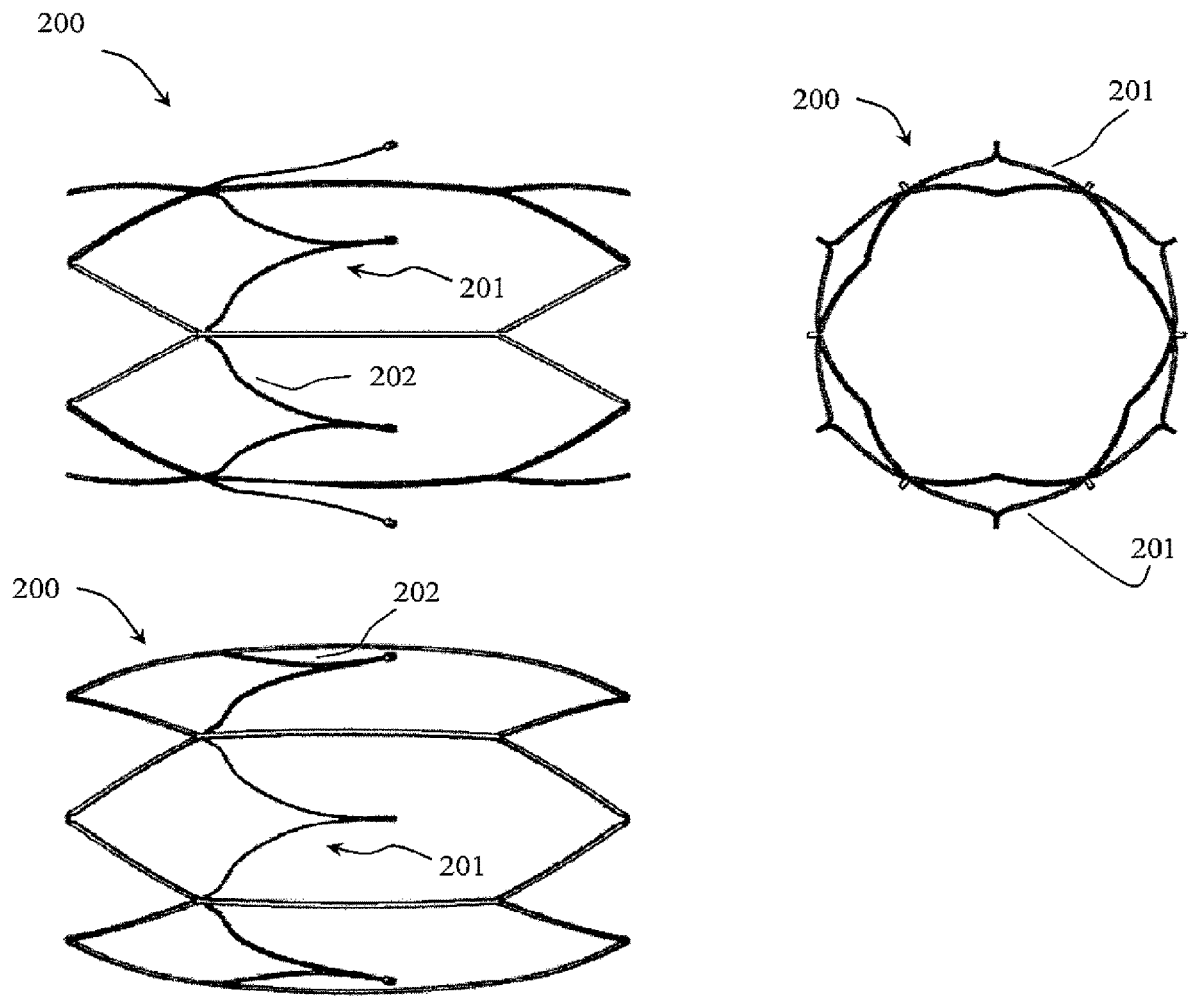
FIG. 15 is a pair of side views and an end view.
Figure 16:
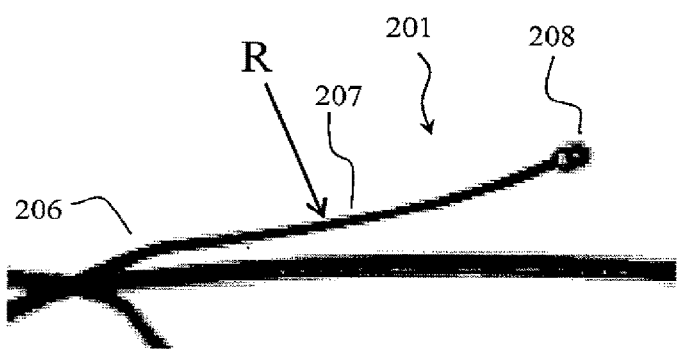
FIG. 16 shows enlarged detail of an element arm and its joint to a support.

FIG. 15 shows the device in an unconstrained configuration and FIG. 16 shows a detailed image of the filter element 201 profile in elevation view. The bump at the start of the filter element is a visual effect of the 3D geometry as the proximal straight section 206 (shown in FIG. 14) follows the contours of the barrel shape as each of the arms 202 curve toward each other before they merge into the distal tip of the filter element 201. This visual effect occurs because the position of the filter element arm 202 rises along the surface of the barrel shape as shown in FIG. 6 to FIG. 10. The visual hump effect is more prominent at the proximal end of the filter element 201 as the arms 202 are further apart and merge distally together at a sharp angle. At the distal end of the filter element 201 as shown in FIG. 16, the arms 202 are closer together and the distally merging angle is less sharp which affords the elevation profile of the 3D shape a truer representation of the 2D profile. Another way of looking at this visual effect shown in FIG. 16 is to imagine a vertical plane slicing through the device along the central axis (through the eyelet 208) and parallel to the elevation view plane, the distance between each of the filter arms 202 and the vertical plane is greatest at the proximal end and reduces rapidly for the proximal segment 206 while the distance reduces to zero more gradually towards the distal end in where the two arms merge. The greater the distance between the arms and the shorter the distance the arms merge over, the greater the visual effect of the hump as the filter arm position will appear to rise as it extends in a circumferential curve towards the vertical plane. The axial curve of the distal section allows the distal tip of the filter element to curve back towards the vessel wall post conversion ensuring that even in the presence of unforeseen endothelial growth; the distal tip will extend radially outwardly for minimised obstruction to the blood flow. A perceived disadvantage to this design is that a central portion of the distal curved section 207 may extend into the blood flow where little endothelial growth has occurred. To mitigate against this, the distal end of the distal section may be manufactured with reduced strut width and/or thickness to provide additional flexibility so that the distal tip and eyelet bend back when in contact with the vessel wall and allow the central portion of the distal section to lie closer to the vessel wall. However, in the long term this is not viewed as a disadvantage as the gap between the central portion and the vessel wall will be minimal and in time, endothelial growth will extend along the filter arms for unobstructed blood flow.

Figure 17:
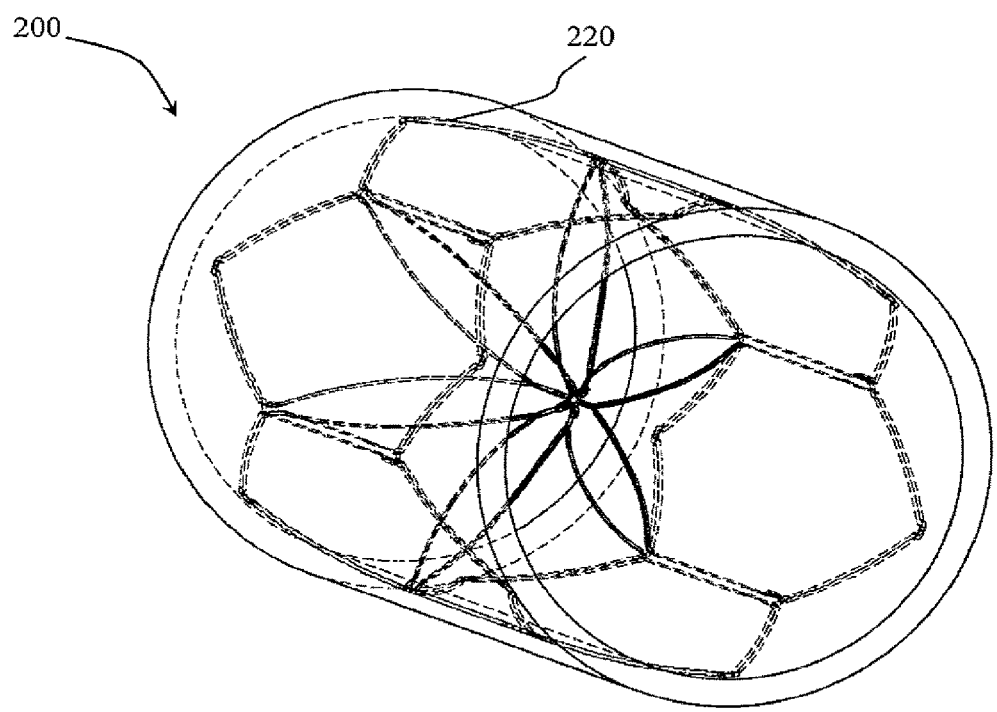
FIGS. 17 and 18 are views of a further device in use while filtering with endothelial growth.
Figure 18:
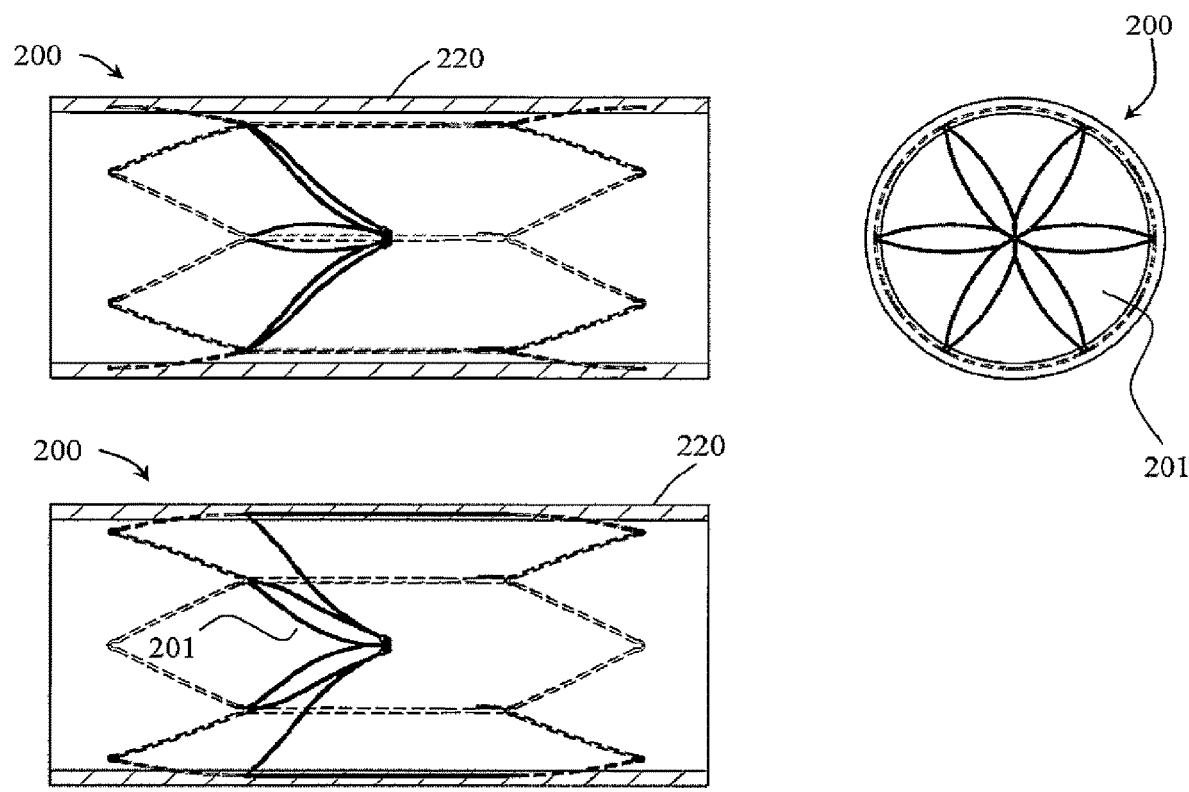

FIGS. 17 and 18 show use of the device 200 during filtering. The filter elements 202 form a less concave curve facing radially outwardly in the filtering configuration when compared to the unconstrained configuration, however, most of the bending required to bring the filter elements from the unconstrained configuration to the filtering configuration occurs over the first 10 to 15 mm of the filter element where the transition between the proximal section 206 and the distal section 207 is located. A gradual transition is preferred here to enhance durability and fatigue performance, preferably with a radius greater than 5 mm. This will aid in moving the strain away from the connection at or adjacent to the distal peak of the proximal support hoop 204.

Figure 19:
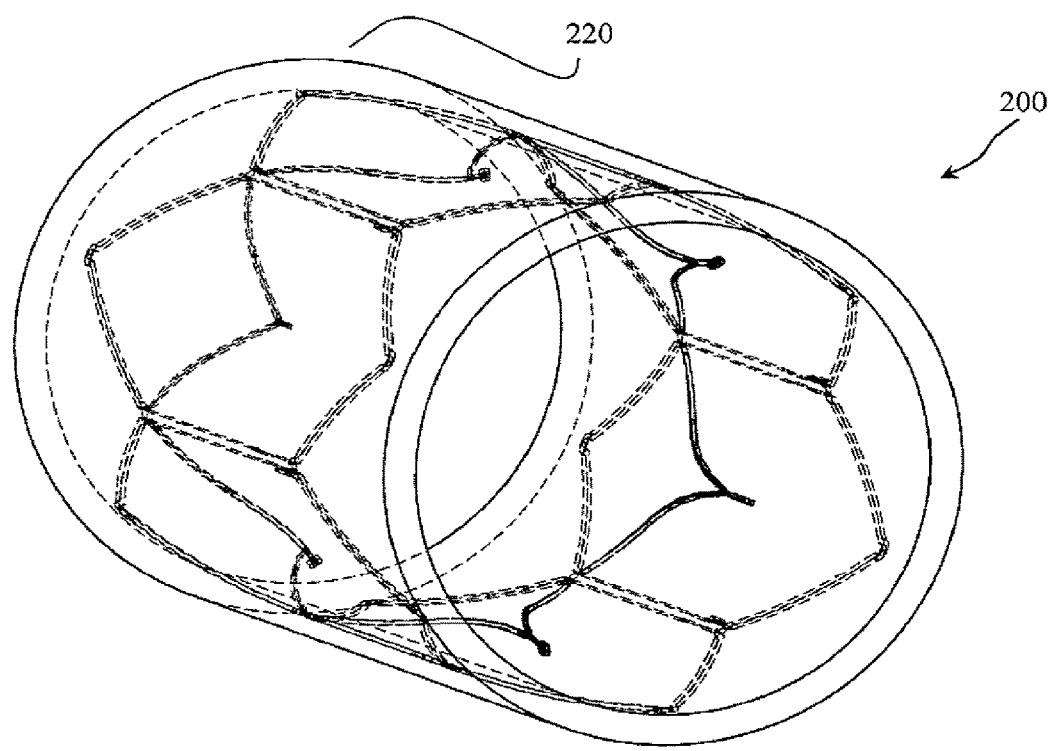
FIGS. 19 and 20 show the device after filter opening.
Figure 20:
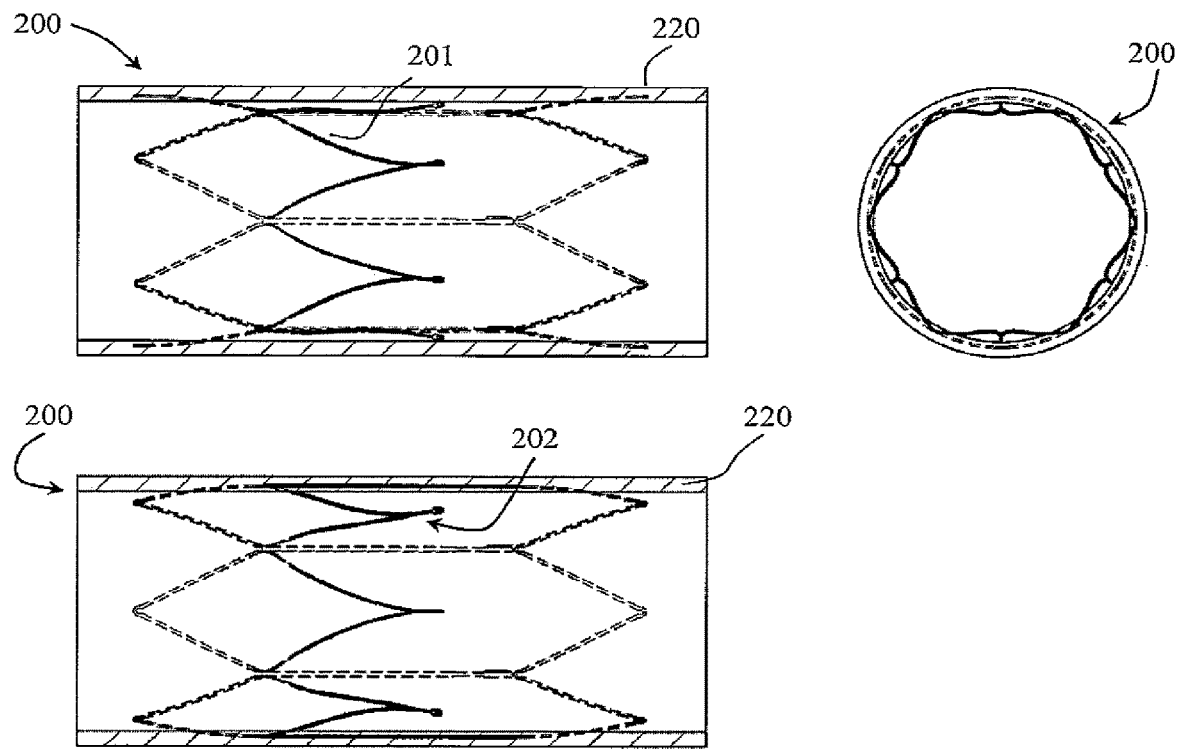

FIGS. 19 and 20 show the device after conversion and before further endothelial growth. The filter elements 201 retract with the eyelets 208 in contact with the vessel wall and the proximal section 206 accounts for endothelial growth 220 upon conversion. The distal section 207 protrudes slightly into the blood flow as the initial endothelial layer formed up to the point of conversion is normal and not excessive. Note that as the distance between the vessel wall and the distal section 207 is small, disturbance to the blood flow is minimal and endothelial covering is promoted. Preferably, this distance is less than 4 mm, even more preferably less than 2 mm.

Figure 21:
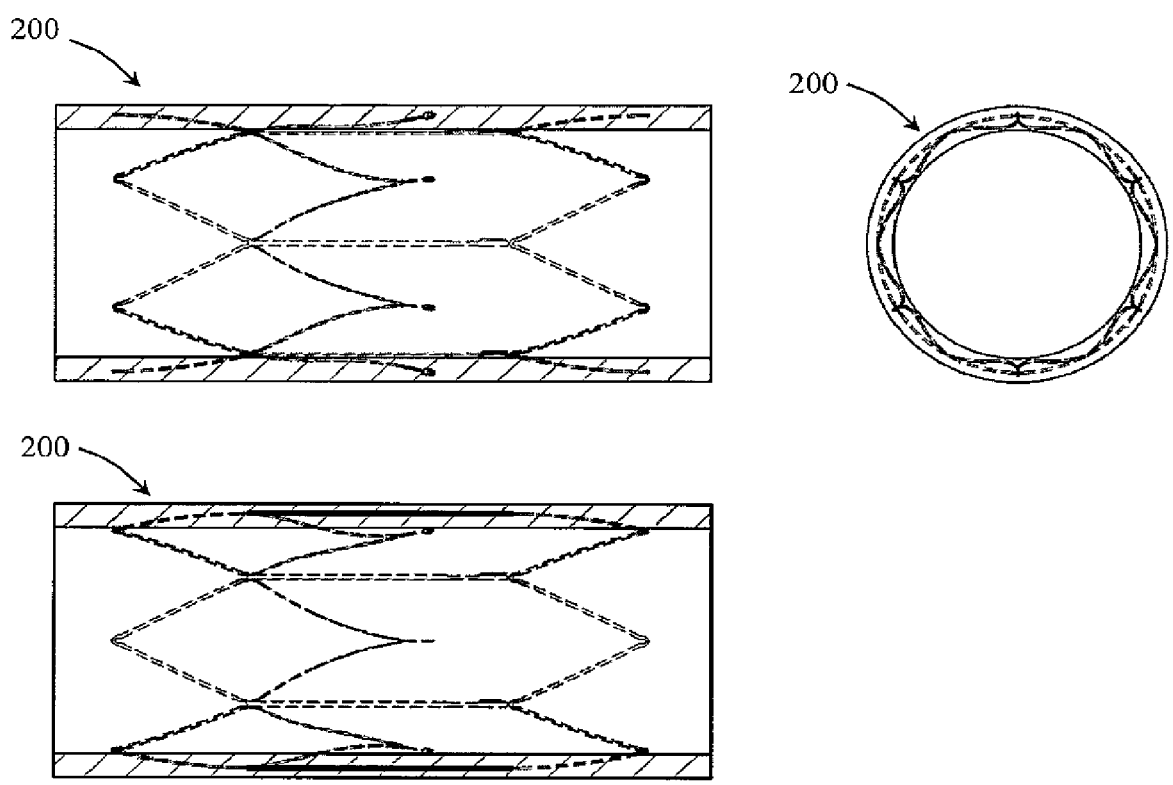
FIG. 21 shows the device after further endothelial growth.

FIG. 21 shows the device 200 after further endothelial growth post conversion. The filter arms continue to push outward against the vessel endothelium post conversion. This, in combination with continued endothelial growth will cover the filter arms fully for unobstructed blood flow.

Figure 22:
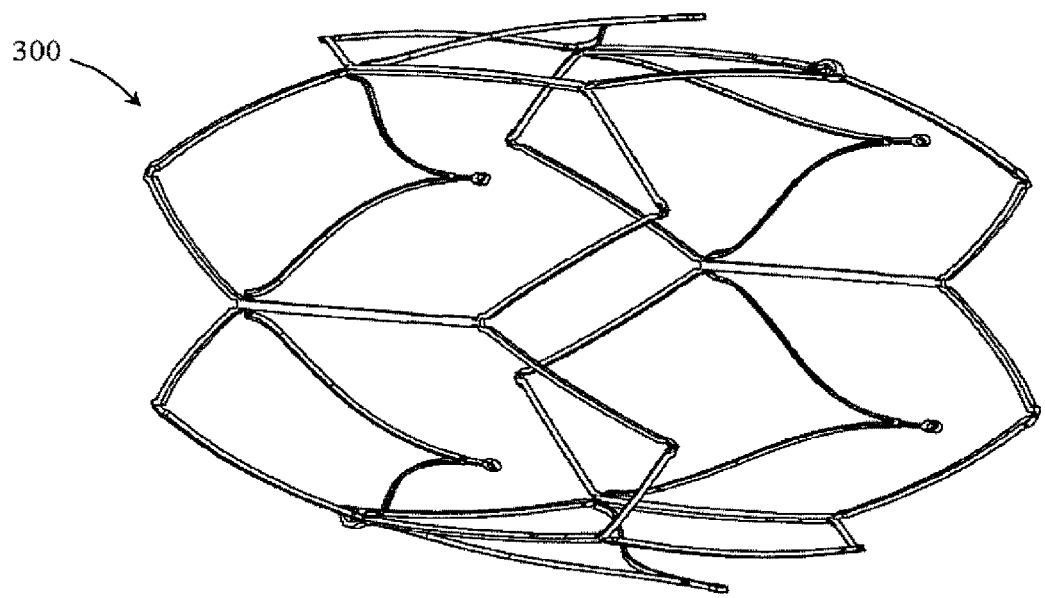
FIGS. 22 to 26 are views of a prior art device.
Figure 23:
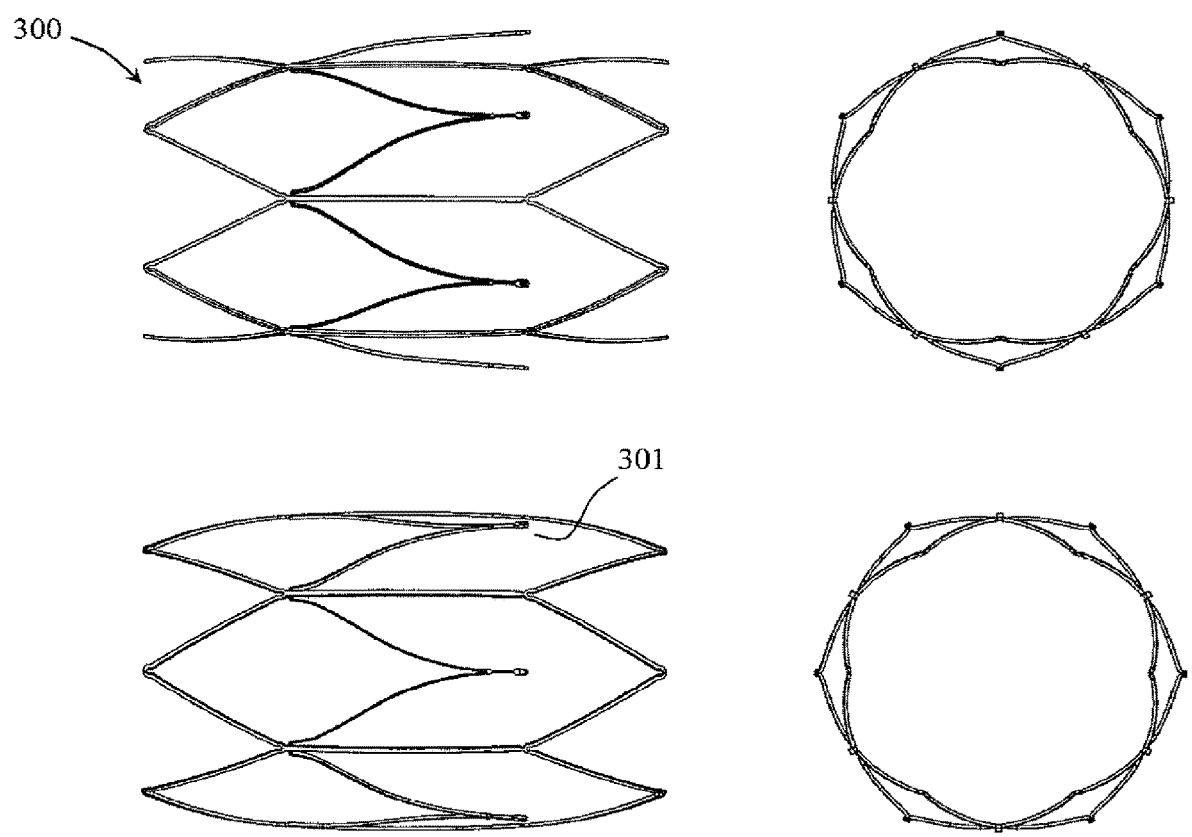
Figure 24:
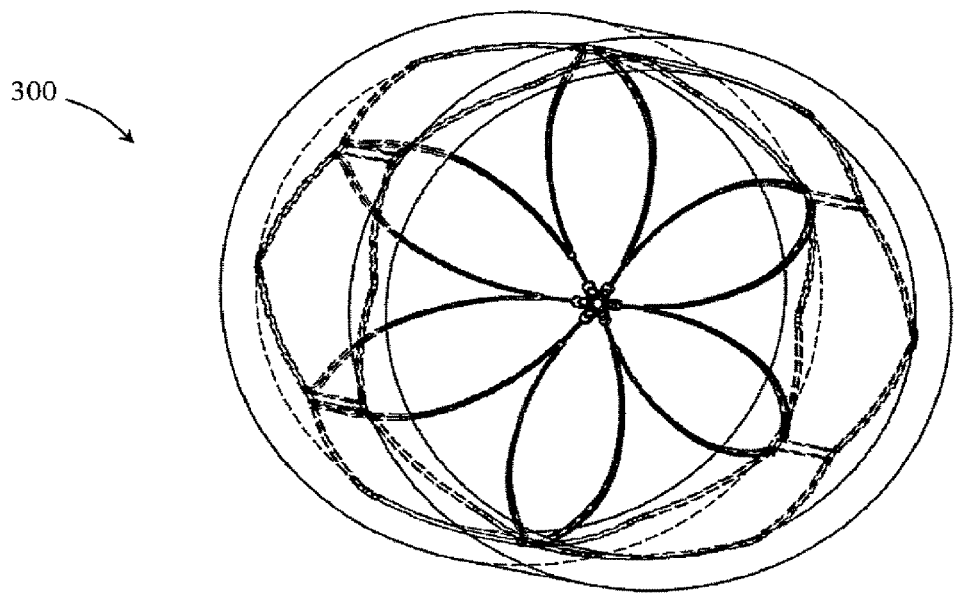
Figure 25:
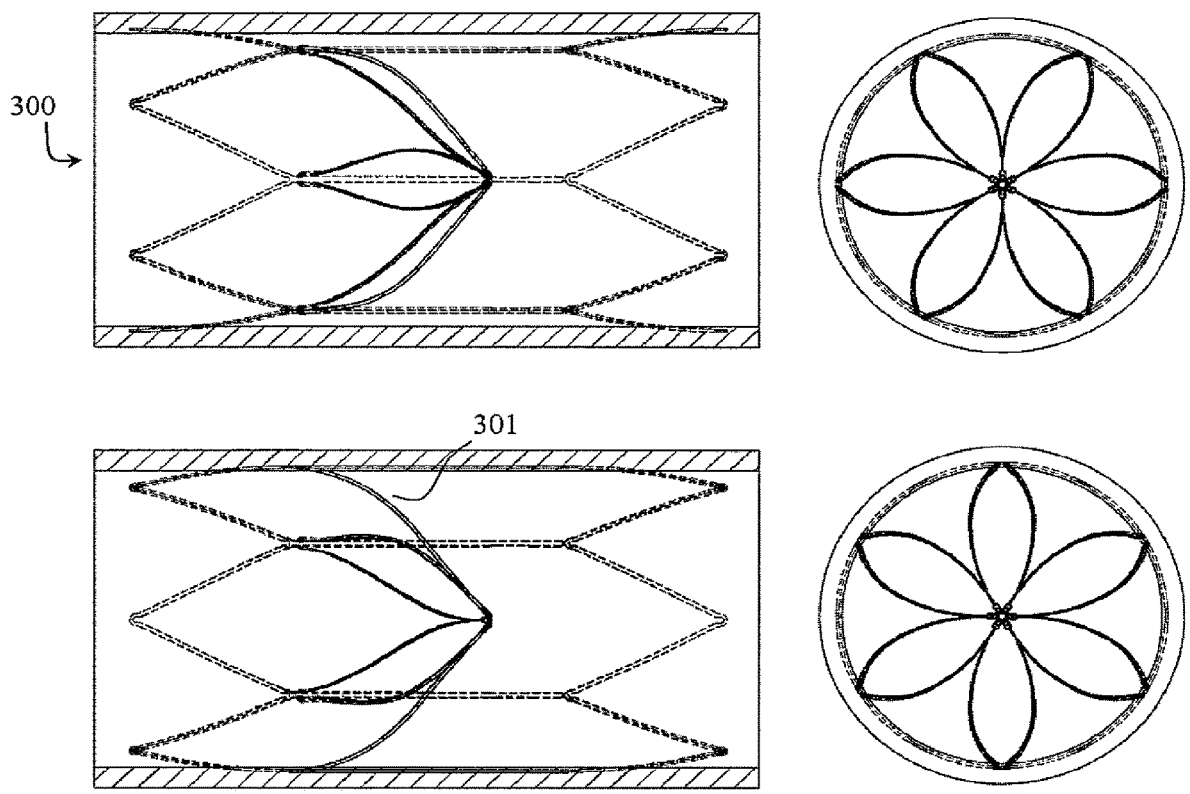
Figure 26:
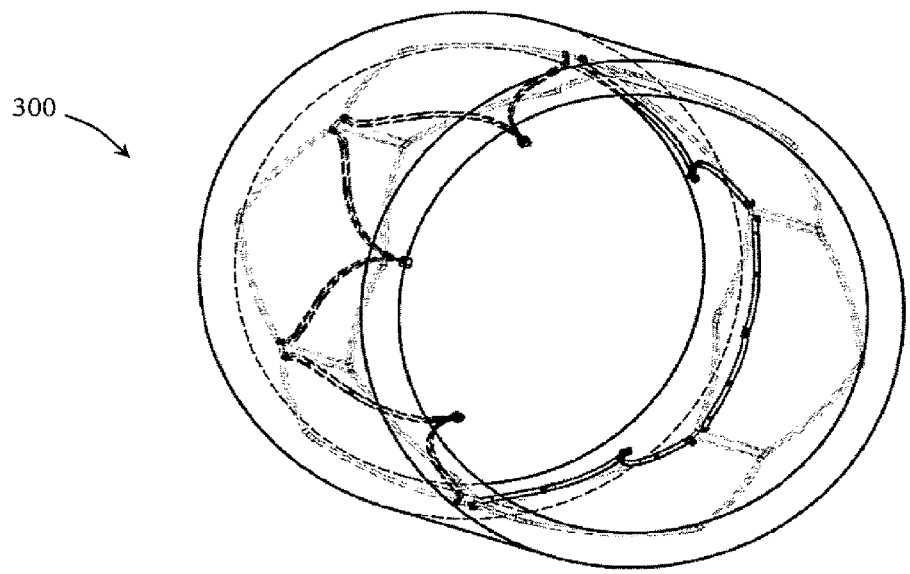
Figure 27:
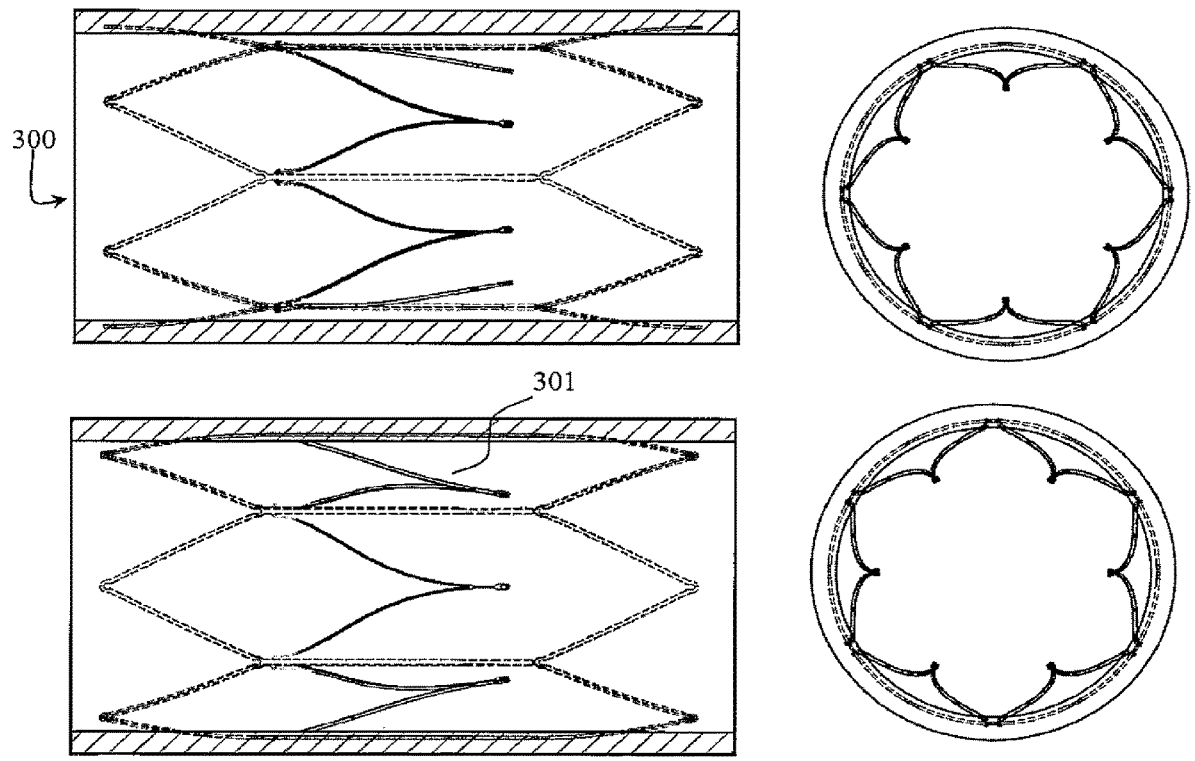

FIG. 22 to FIG. 27 depict the prior art device 300 with filter elements 301 in various stages of use (previously filed in U.S. Pat. No. 8,057,507). FIG. 22 and FIG. 23 show the device unconstrained with the support frame forming an overall barrel shape and with filter elements 301 flared slightly at their distal end, the proximal end following the barrel shape of the support frame. FIG. 24 and FIG. 25 show the device filtering with an initial endothelial layer. FIG. 26 and FIG. 27 show the device post conversion with the distal ends of the filter elements extending into the blood flow. The proximal end of the filter elements 301 has been fixed in position by the endothelial covering and the convex filter element flare facing radially outwardly does not allow the distal end of the filter element to extend outwardly towards the vessel wall.

Figure 28:
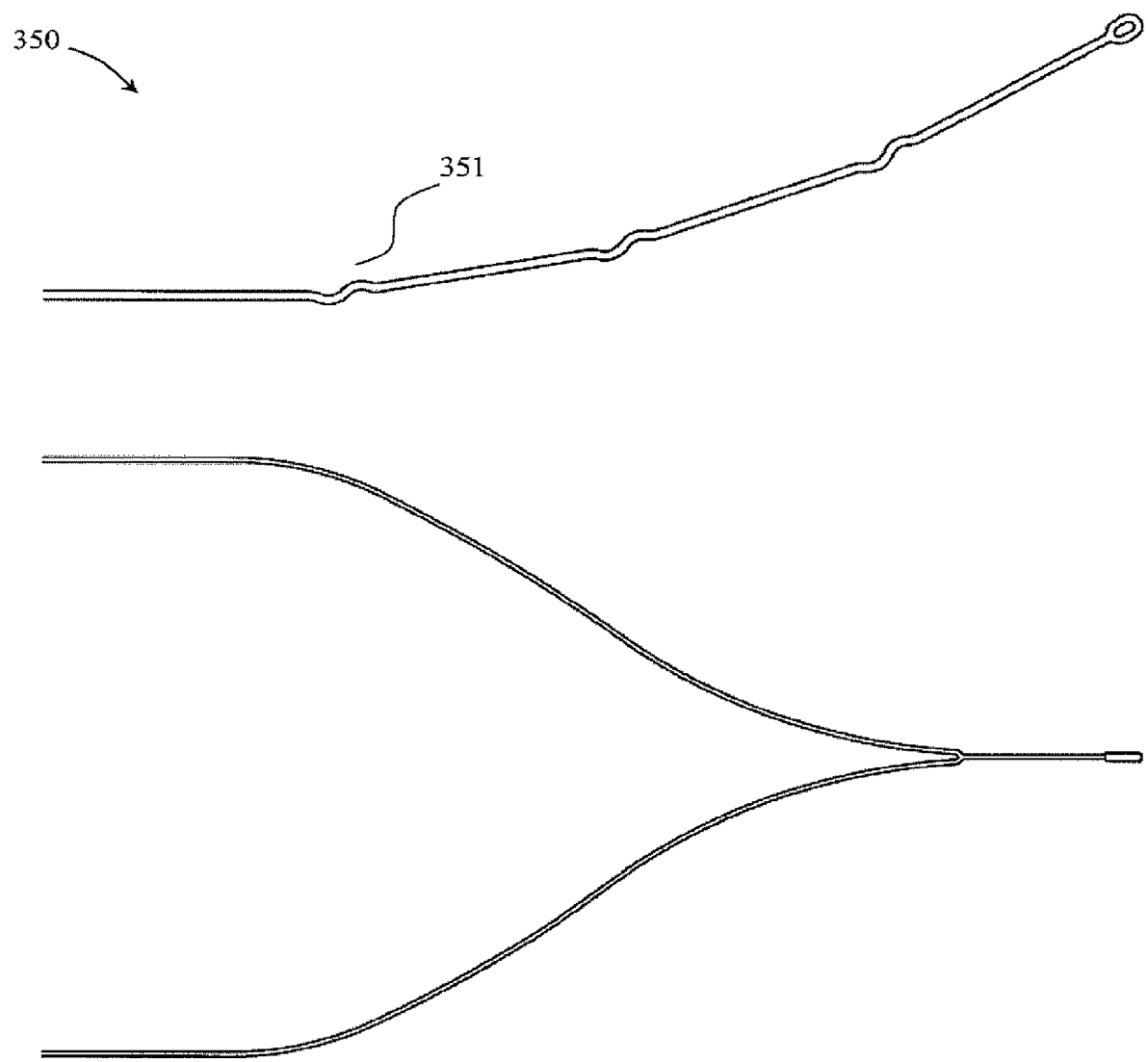
FIGS. 28 to 30 show various filter arm articulations to aid conformability to the vessel wall.
Figure 29:
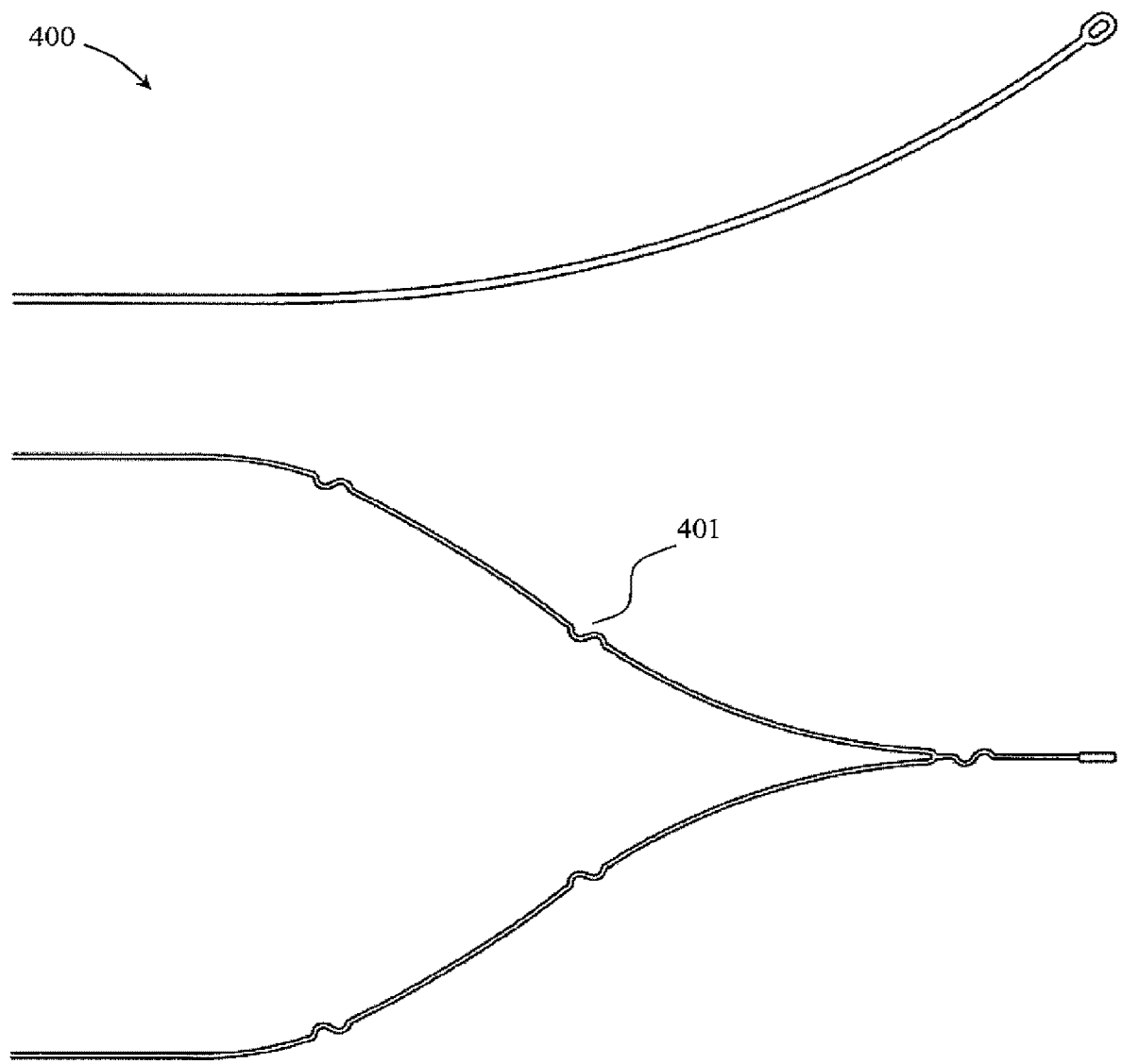
Figure 30:
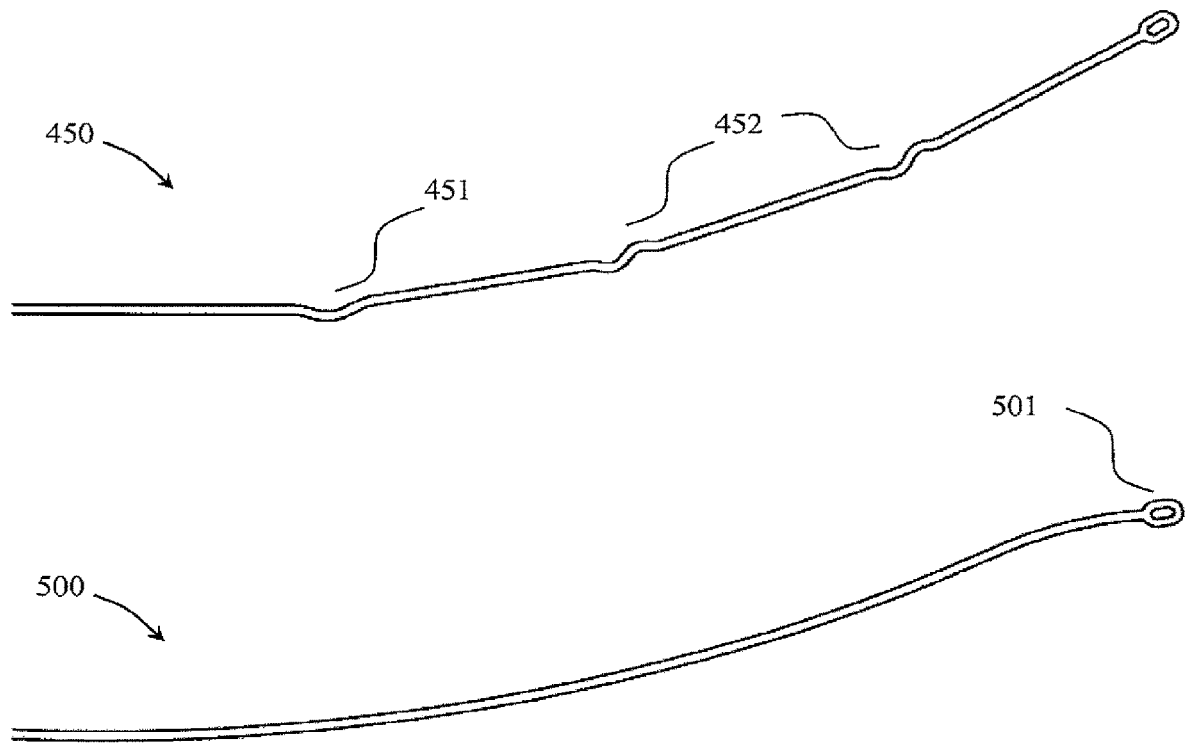

FIG. 28 depicts a further embodiment of the invention where the filter element 350 is formed with articulations 351 at different locations along the length of the filter element. The elevation view shows the articulations 351 at the top of the image. Articulations 351 are intended to provide flexibility for the filter element along its length so that the filter element can conform to irregular vessel shapes and so that if minimal endothelial growth has occurred, the distal end will bend radially inwardly in order to reduce the risk of perforation of the vessel wall with the distal tip of the filter element. FIG. 29 shows a filter element 400 with articulations that are laser cut into the filter element profile when cutting the device from raw tubing (before expanding and heat setting using the forming tool). Alternatively, these articulations may be formed using the heat setting method as with device 350. FIG. 30 depicts a filter element 450 with articulations 451 and 452 in the top image. Articulation 451 imparts less longitudinal flexibility than articulation 452 to provide a filter element with more stiffness proximally (in order to overcome endothelial growth) and less stiffness distally (in order to enhance conformability to the vessel wall). It is appreciated that the articulations may be provided in different forms such as U-shapes and S-shapes shown in articulations 451 and 452 respectively and that other shapes may also be used. For example, reducing strut width and/or thickness over a short distance would also provide stiffness variations at different locations where required. In another embodiment, the strut width and/or thickness can be tapered along the length of the filter element in order to provide a stiff proximal section with a flexible distal section. The bottom image of FIG. 30 shows a filter element 500 with a radially inward bend 501 at the distal end that ensures the distal end does not poke into the vessel wall post conversion in order to reduce the risk of perforation.

Figure 31:
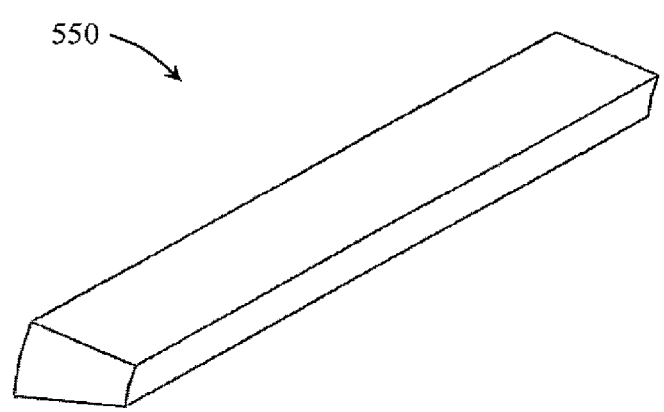
FIGS. 31 to 32 are perspective views of filter element cross sectional profiles.

Filter elements that are cut from a cylindrical tube will have a wedge shaped cross section as shown in FIG. 31. The widest part of the wedge shape is formed from the OD of the raw tube and is in contact with the vessel wall post conversion.

Figure 32:
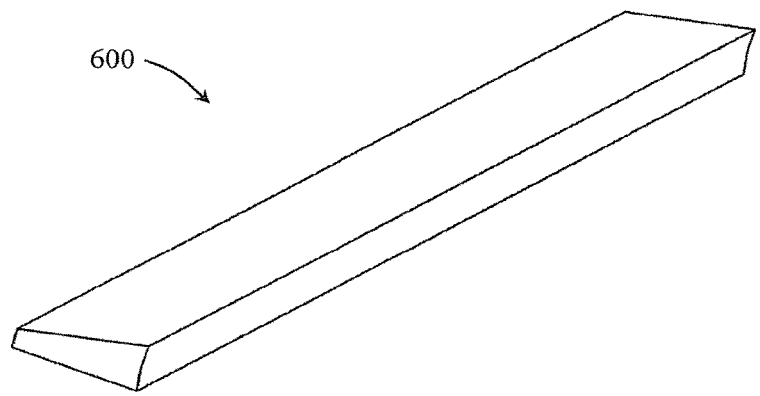

FIG. 32 shows that a grinding process could remove material from the outside of the filter element to reduce the surface area of the filter element in contact with the vessel wall. This would increase the pressure on the vessel wall and encourage movement of the filter arm through the new endothelial tissue. If this grinding process was applied to the proximal end of the filter arms where most of the resistance is seen, it would increase filter arm apposition to the vessel wall post conversion.

In addition to overcome the 'wedging' effect of endothelial growth, a further aspect of the present invention includes overcoming growth (biological matter, i.e. fibrin). Growth at the apex, if present, may restrict conversion from filtering to non-filtering as it may act like a holder member if it has formed in sufficient quantity and/or stiffness. Factors that promote growth at the apex include poor flow dynamics, hypercoagulability (increased tendency of patient's blood to clot), and material mediated foreign body response. To overcome this problem, the filter elements must have sufficient radial force to break apart. A number of measures can be implemented to increase the stiffness of the filter element which in turn increases the radial force at the eyelet. Also the inherent design feature of a V-shaped filter element doubles the radial force at each filter element eyelet at the filter apex. These measures include having a short filter element length, increasing wall thickness (radial direction) of filter element, increasing filter element strut width (circumferential direction), and/or increasing the OD of the raw tubing the filter is cut from (increases the angle of the wedge shaped cross section to form a more squarely shaped cross section with increased stiffness).

Figure 33:
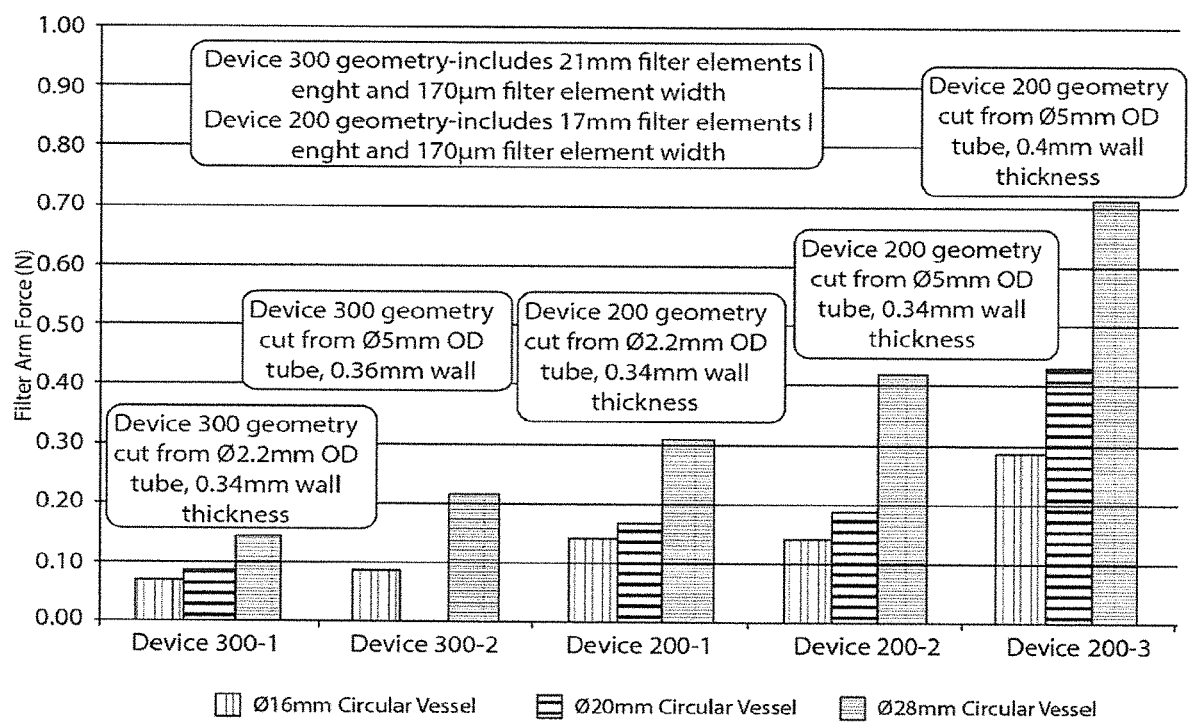
FIG. 33 is a bar chart showing filter element forces for various embodiments.

FIG. 33 illustrates the radial force at the filter element eyelet incorporating a number of these measures. The filter element preferably has a radial force at the eyelet ranging from 0.1 to 1.0 N in vessel sizes ranging from ID 16 mm to ID 28 mm. More preferably, the filter element has a radial force ranging from 0.1 to 0.4 N in vessel sizes ranging from ID 16 mm to ID 28 mm. In order to achieve this range of forces at the eyelet, the following filter element characteristics are preferred: [0194] Filter element length preferably ranges from 15 to 30 mm, more preferably from 17 to 23 mm [0195] Raw tube diameter preferably ranges from OD 2 mm to OD 10 mm, more preferably from OD 2.2 mm to OD 6 mm [0196] Wall thickness preferably ranges from 0.2 mm to 0.6 mm, more preferably from 0.3 mm to 0.4 mm [0197] Filter element arm width preferably ranges from 100 .mu.m to 400 .mu.m, more preferably from 150 .mu.m to 250 .mu.m.

Another embodiment of the invention relates to features that reduce the risk of growth at the apex. Y-shaped filter elements may be provided to provide a more streamlined profile to minimise obstruction to the blood flow. This will reduce irregular flow patterns and shear blood flow forces to in turn reduce fibrin and/or clot formation. Further enhancements are disclosed in this patent application. The apex region of the filter including filter elements and holder member may be coated with an anti-thombogenic material to prevent fibrin and/or thombin growth. Preferred materials include hydrophobics, hydrophillics, materials impregnated with biological agents, or a combination of these.

A further embodiment includes a filter frame and filter elements manufactured using a first degradable material and a holder member manufactured using a second degradable material, wherein, the frame manufactured from the first material degrades at a slower rate than the holder member manufactured from the second material. The holder member degrades first allowing the filter elements to convert and become encapsulated in the vessel wall. The filter frame and filter elements degrade at a point in time after conversion and preferably after endothelial encapsulation to prevent the frame from embolisation. Preferably, the frame is manufactured from a metal alloy such as magnesium and the holder is manufactured from a polymer such as polydioxanone. It is appreciated that other metallic, polymeric and composite materials may be used in place of magnesium and polydioxanone.

Figure 34:
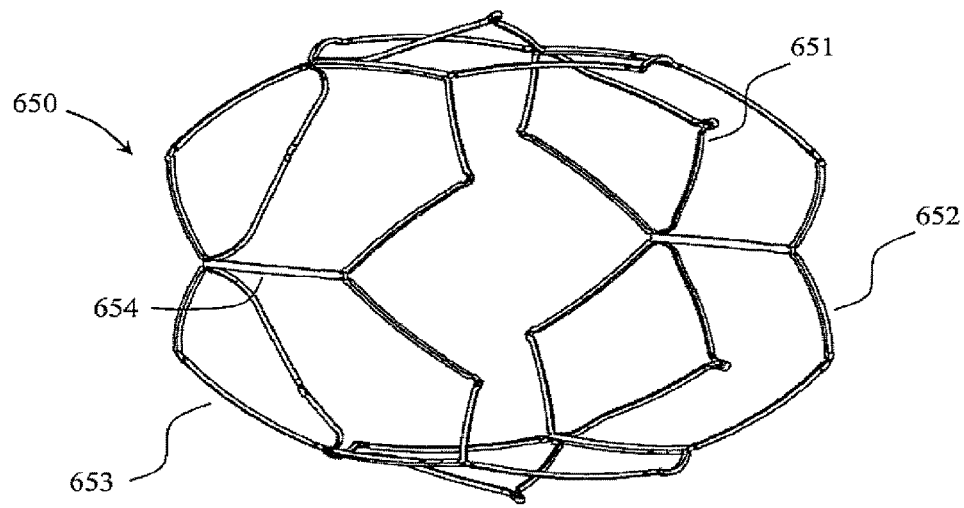
FIG. 34 is a perspective view of an alternative filter device in which filter elements are V-shaped and directed radially outwardly when relaxed.
Figure 35:
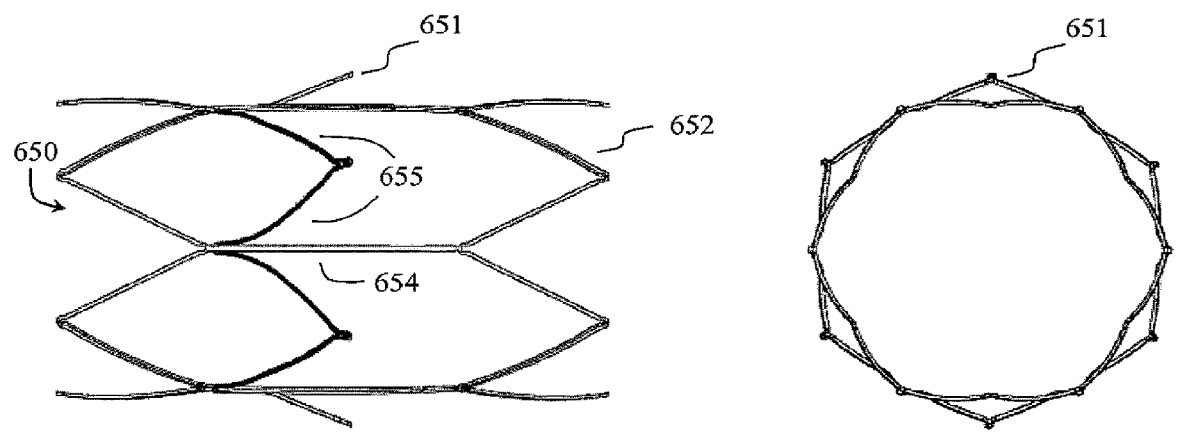
FIG. 35 is a set of side and end views of this device with its filter in the open position.
Figure 35:
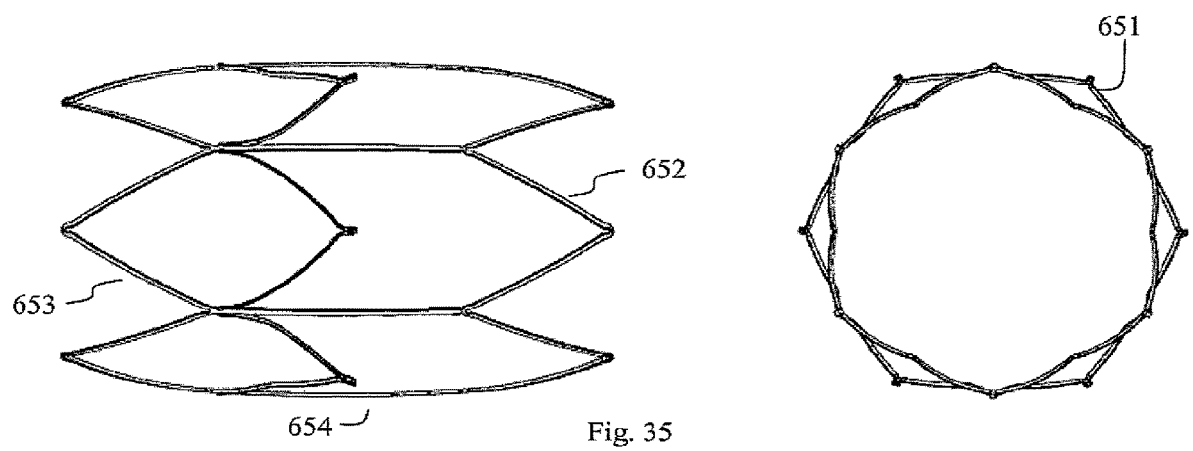
Figure 36:
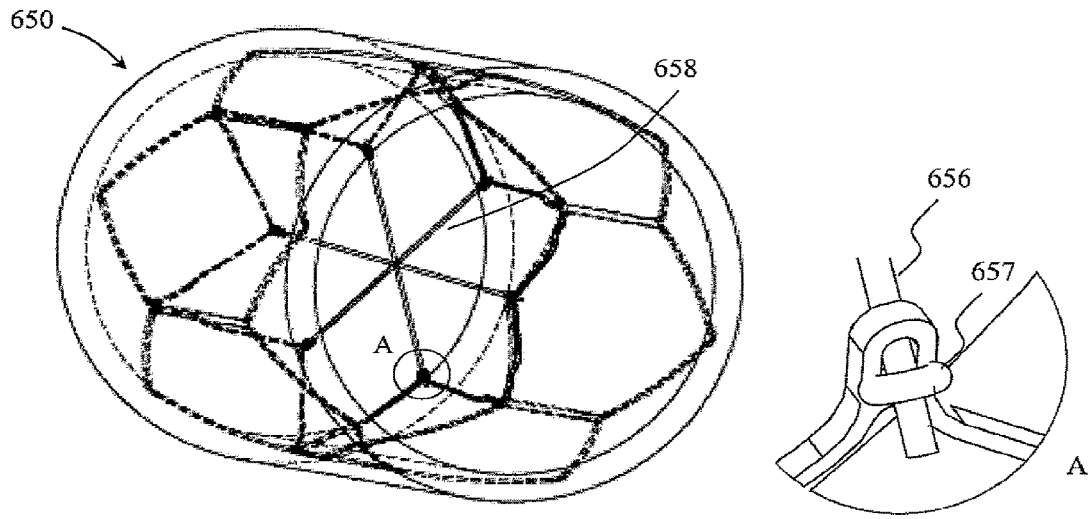
FIG. 36 shows a detail of connection of a holder acting as a primary filter element to a support member acting as a secondary filter element for the filter closed position in which the filter elements do not inter-engage at an apex.
Figure 37:
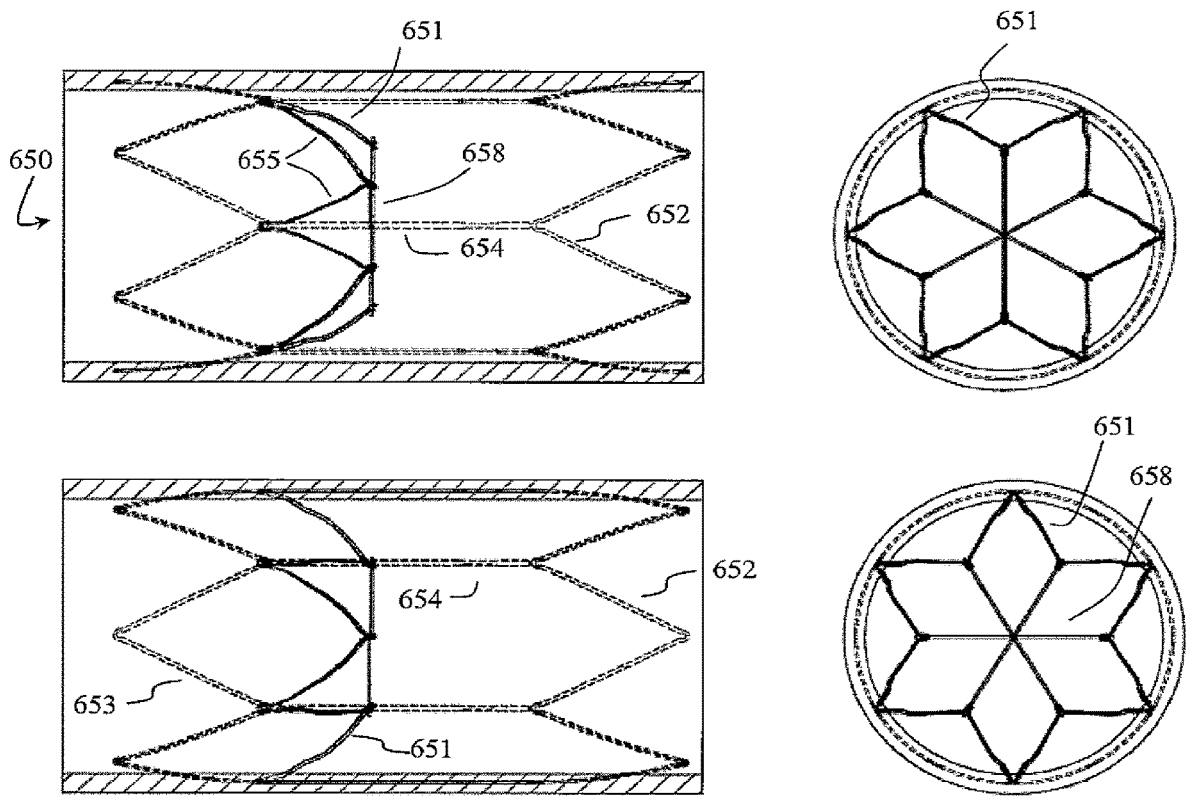
FIG. 37 is a set of views with the filter closed.
Figure 38:
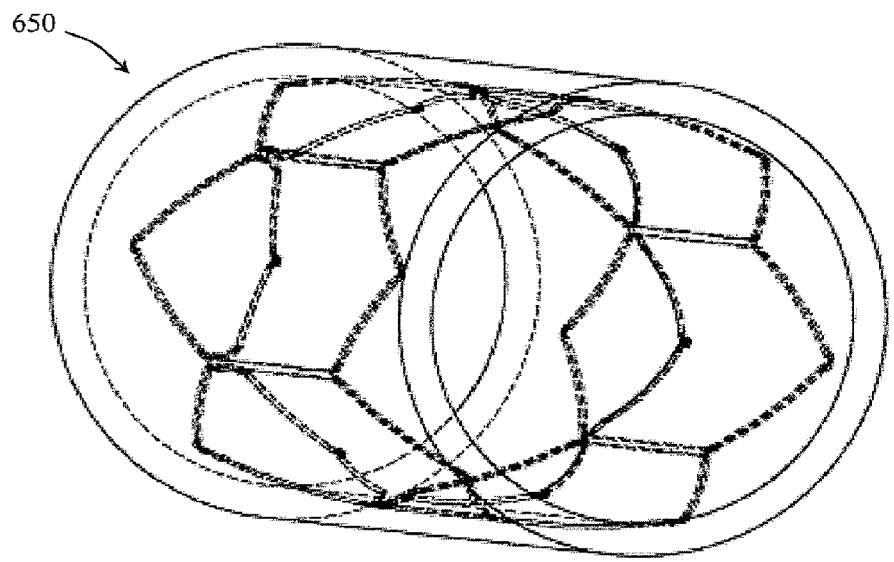
FIGS. 38 and 39 show the device when the filter is open and it is located in a vessel.
Figure 39:
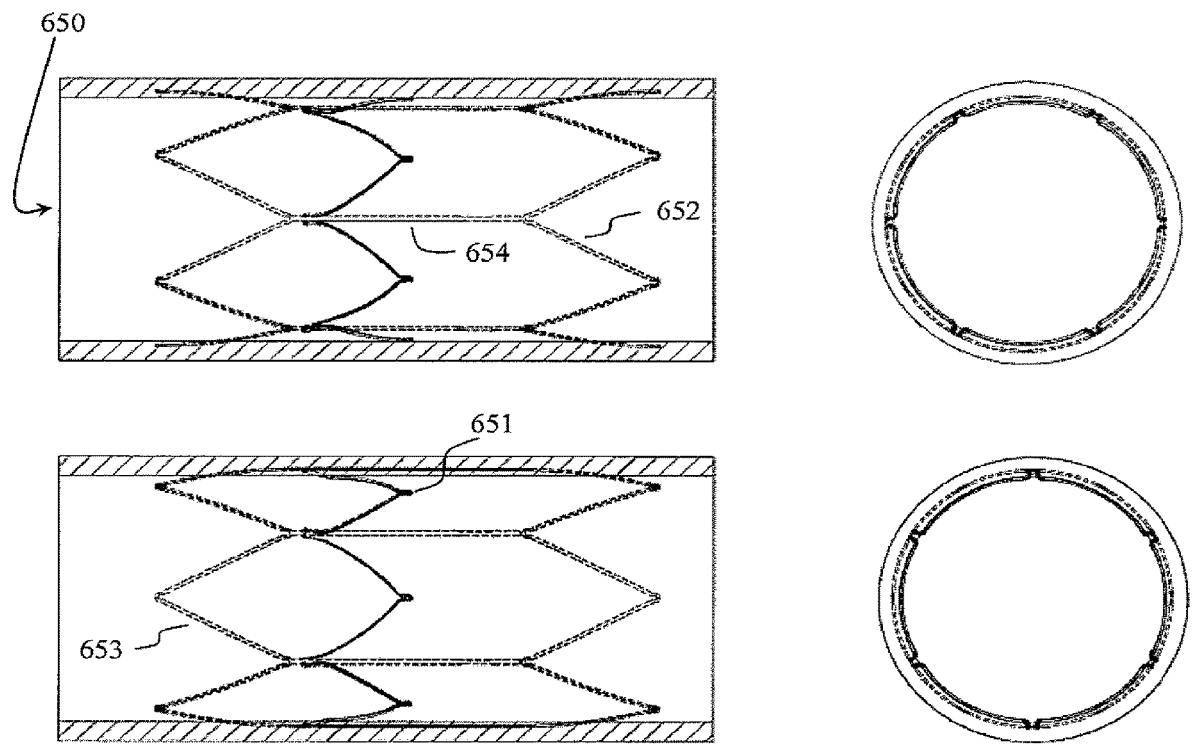
Figure 40:
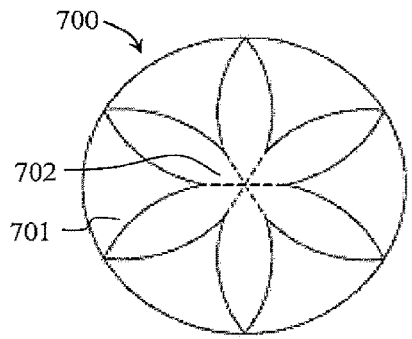
FIGS. 40 to 51 are end views of alternative devices in which the holder acts as primary filter elements and where members integral with the support frame act as secondary filter elements with their filters closed.

In another embodiment, a truncated filter body is adopted where a biodegradable holder member is held in tension by filter elements biased to extend radially outwardly relative to a stent-like support frame after the holder member has degraded. FIG. 34 to FIG. 39 show such a device with a proximal support hoop 653, a distal support hoop 652, connector struts 654 extending between the proximal and distal hoops 652 and 653, filter elements 655, and a holder member 658. The filter elements 655 are held radially inwardly of the vessel wall by the holder member 658, the holder being slack when in a delivery configuration and taut when in use through application of a radial force imparted by the filter elements 655 which are biased to flare radially outwardly. The holder member 658 may comprise a plurality of flexible threads or sutures 656 extending between opposing filter elements 655. The filter elements 655 preferably are of v-shaped construction and may have eyelets 651 at the apex of the V-shape. However, the filter elements 655 may also be y-shaped. The filter elements preferably include measures discussed in previous embodiments of the application to counteract the effects of endothelial growth such as a proximal straight section and flared distal section. Threads 656 extend through the eyelets 651 if supplied or may be wrapped around the apex of the v-shaped filter elements 655 before tying a knot to secure in place. Alternatively, a secondary component or feature may be used to secure the thread in place such as the stop feature 657 which may be crimped, over-moulded, or ultrasonically welded in place. Alternatively, the stop feature is formed integrally with the thread by applying heat after assembling the device—a low heat is preferred to ensure the integrity of the biodegradable thread is maintained and to prevent the stop feature from degrading prematurely. Compression and/or torsion may be employed during the heat moulding step to extend the degradation time of the stopper relative to the thread—this would ensure that the filter elements bring the plurality of broken threads to the vessel wall after the device has opened so that the threads do not become an embolus. During assembly, the threads may be intertwined at a central apex to provide uniformity. The distance between the eyelets 651 will remain the same irrespective of the vessel diameter as the length of each of the threads 656 will not change. The length of each thread or diameter of the taut planar holder member should be sized between 1 and 16 mm, preferably between 3 and 6 mm—the preferred range will prevent the filter elements eyelets from being attached to each other by fibrin and or thrombin formation at a central apex by being sufficiently spaced apart in order to allow successful retraction of the filter elements to the vessel wall. FIGS. 34 and 35 show the device in an unconstrained configuration before assembly with a holder member, FIG. 36 shows the assembled device in a vessel with a detailed view of one of the eyelets 651 to the right and FIG. 37 shows plan elevation and end views of the device in use. FIGS. 38 and 39 show the device open with unrestricted blood flow after the holder member has degraded.

Figure 41:
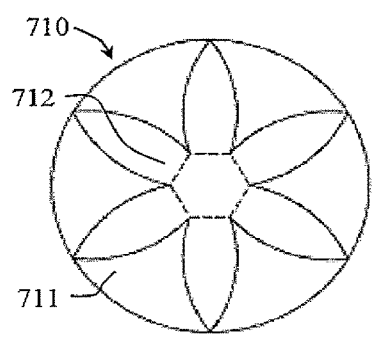
Figure 42:
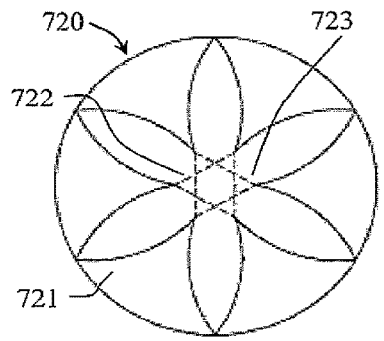
Figure 43:
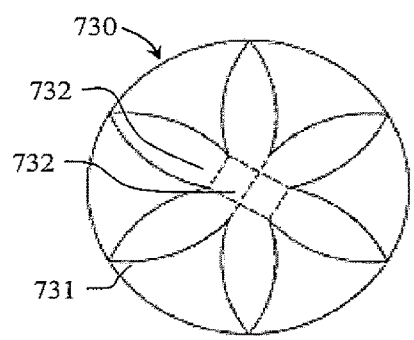
Figure 44:
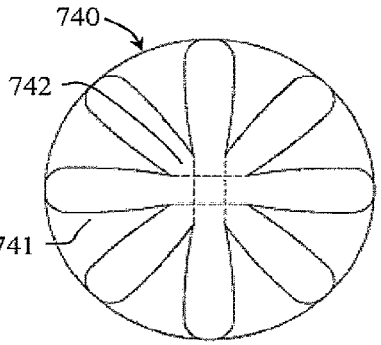
Figure 45:
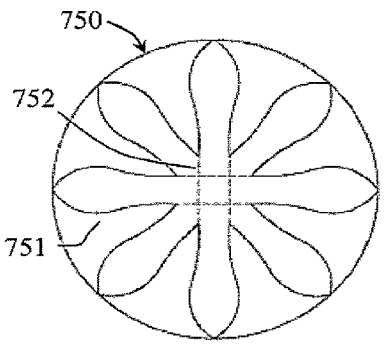
Figure 46:
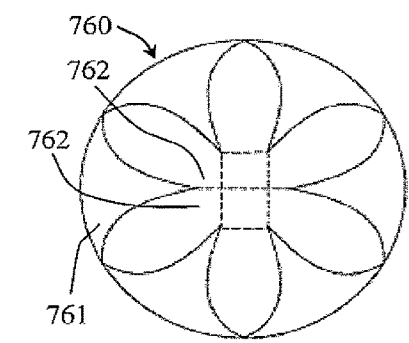
Figure 47:
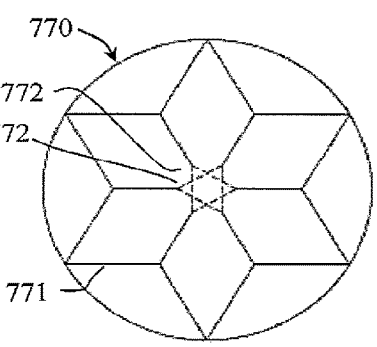
Figure 48:
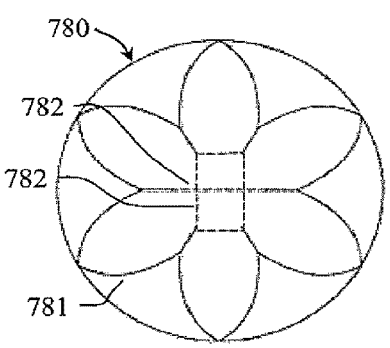
Figure 49:
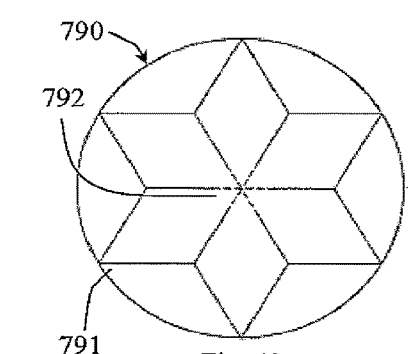
Figure 50:
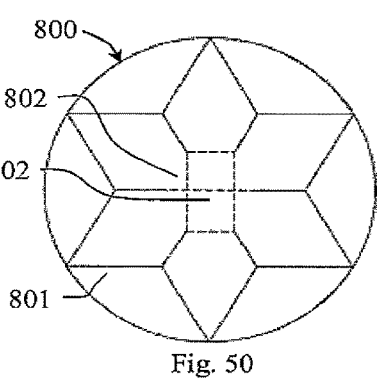
Figure 51:
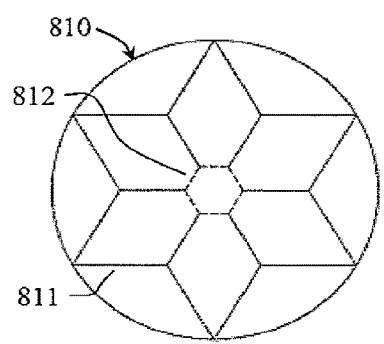

FIGS. 40 to 51 show alternative configurations for the holder member 658 of device 650 including some variations in filter element shape and the number of filter elements. It is possible to use the device with anywhere between 1 and 30 filter elements, preferably, the device is supplied with between 4 and 8 V-shaped filter elements. FIGS. 40 to 43 show the device with filter elements 701, 711, 721, and 731 extending towards an apex in curves that have convex portions facing each other and with varying holder member arrangements 702, 712, 722/723, and 732 respectively. FIG. 41 shows the device with a flexible thread extending through each of the filter elements to form a hexagonal shaped holder 712 where the ends of the thread are tied to one of the eyelets to secure in place. FIG. 42 shows a holder member consisting of one or two threads extending through eyelets to form two triangular shapes 722 and 723 overlapped. FIG. 43 shows a holder member 732 one or two threads extending through eyelets to form two rectangular or square shapes, for instance—one thread extends through 4 eyelets to form a rectangular shape while a second thread extends between two eyelets. FIG. 44 shows a device with eight v-shaped filter elements 741 and with every third filter element connected together by a plurality of four biodegradable threads to form a single square shaped holder member 742. FIG. 45 shows the device 740 with filter elements 751 that have segments extending in multiple curves towards their v-shaped apex—this design maximises space between the filter element struts at the v-shaped apex and between the proximal segment of the filter element struts and the straight connector struts in order to reduce the likelihood of growth that may restrict retraction to the vessel wall. FIG. 46 shows a device 760 with filter elements 761 similar to that of the device 730 with exaggerated curves at the proximal segment—this provides more space between filter elements at their connection to the plurality of connector struts in order to reduce the degree of endothelial growth at this location and to reduce resistance to the filter elements retracting to the vessel wall. FIG. 47 to FIG. 51 show various embodiments of y-shaped filter elements incorporating the truncated conical design where FIG. 47 uses a star shaped holder consisting of two triangles 772 and FIG. 48 shows y-shaped filter elements with curved proximal segments, a convex portion of a first segment facing a convex portion of a second segment, and with a split rectangular shaped flexible planar holder member held taut in the filtering configuration by the cantilever filter elements 781. FIGS. 49, 50 and 51 show the device 770 with an asterix, split rectangle, and hexagonal shaped flexible planar holder members held taut by the straight y-shaped filter elements. It is appreciated that the holder members may be of a rigid design and that they may be non planar—in this case a collapsible holder is preferred to reduce the delivery profile of the device.

Figure 52:
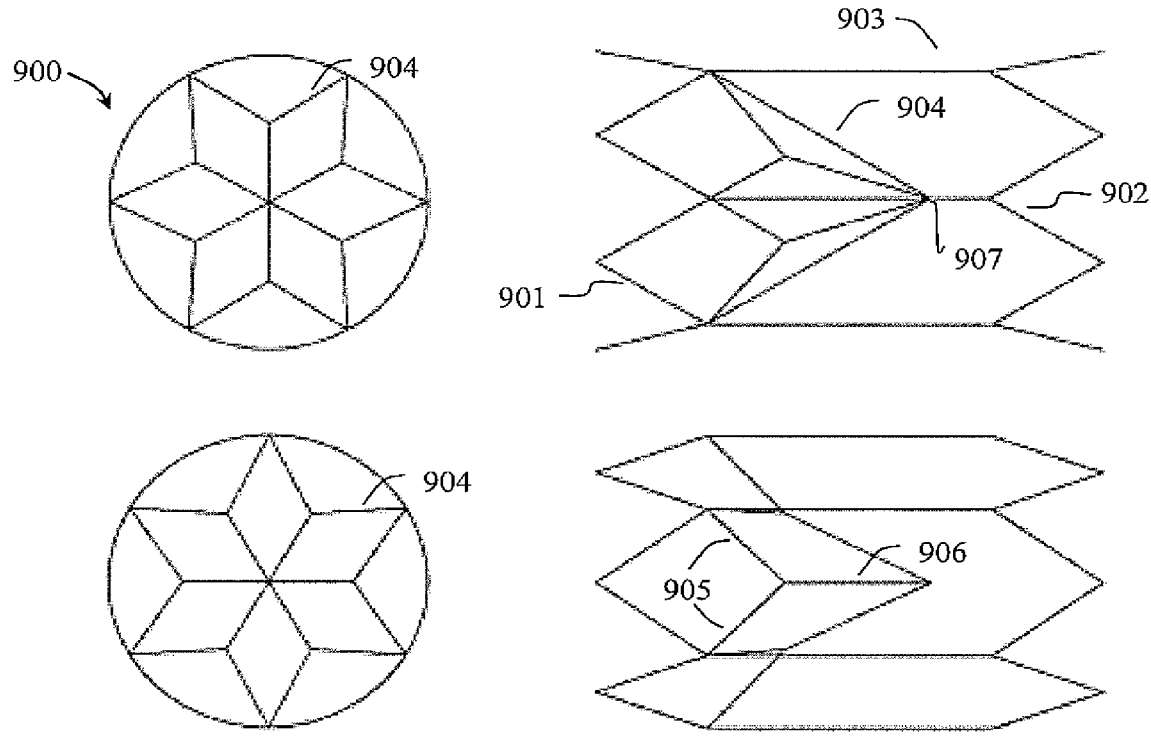
FIGS. 52 to 55 are sets of views showing an alternative filter with straight filter elements in end view.
Figure 53:
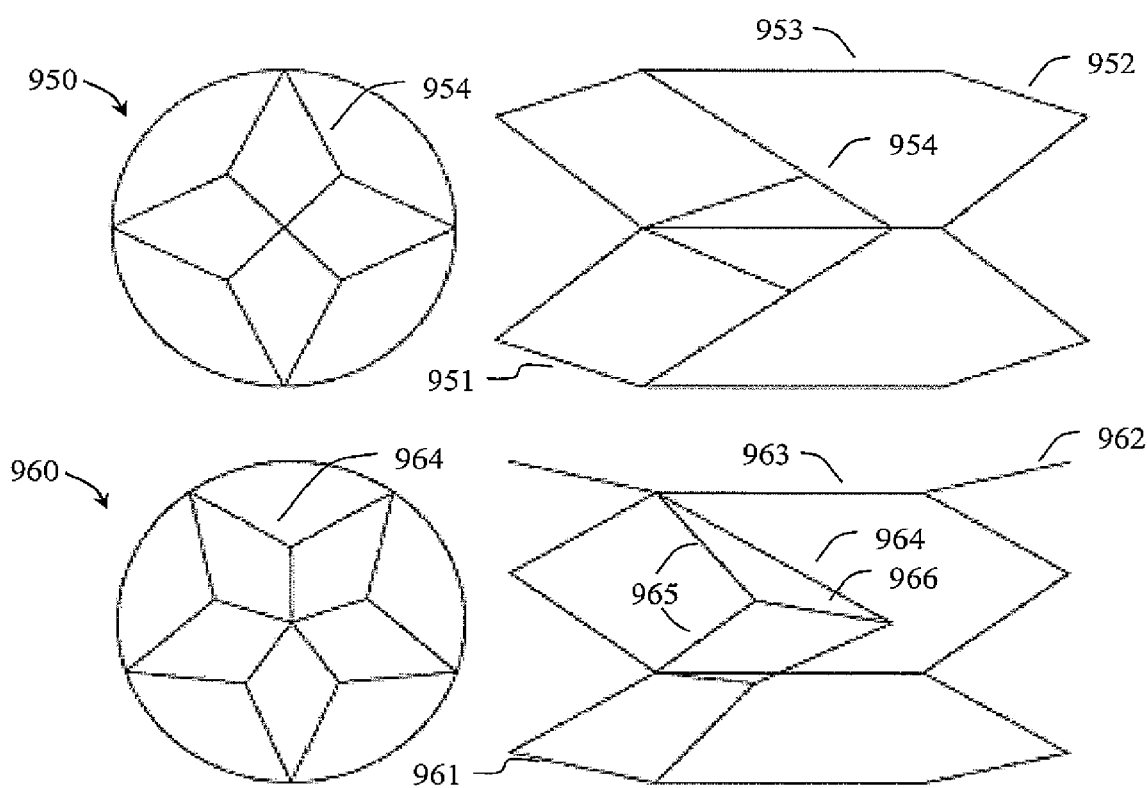

FIG. 52 shows a further embodiment 900 where six Y-shaped filter elements form diamond shaped pores for filtration in combination with a support frame comprising a proximal hoop 901, a distal hoop 902 and a plurality of connector struts 903 extending between 901 and 902. A holder member 907 prevents the filter elements 904 (comprising two proximal segments 905 and one distal segment 906) from retracting to a radially outwardly biased position forming a substantially tubular shape when in the non-filtering configuration. This embodiment is advantageous in that it provides uniform filtration pores. Two further embodiments 950 and 960 are shown in the top and bottom images of FIG. 53 respectively. Device 950 has a plurality of four y-shaped filter elements and four connector struts 953. Shown in the image are four proximal and distal peaks for each of the proximal and distal supports. However, device 950 may be provided with more than four proximal and distal peaks. This filter design reduces the number of filtration struts and increases filtration pore size in order not to provide excessive filtration. Device 960 is similar to device 900 and device 950 in that five y-shaped filtration elements are provided. It is appreciated that less or more filtration elements may be provided with any device presented in this application.

Figure 54:
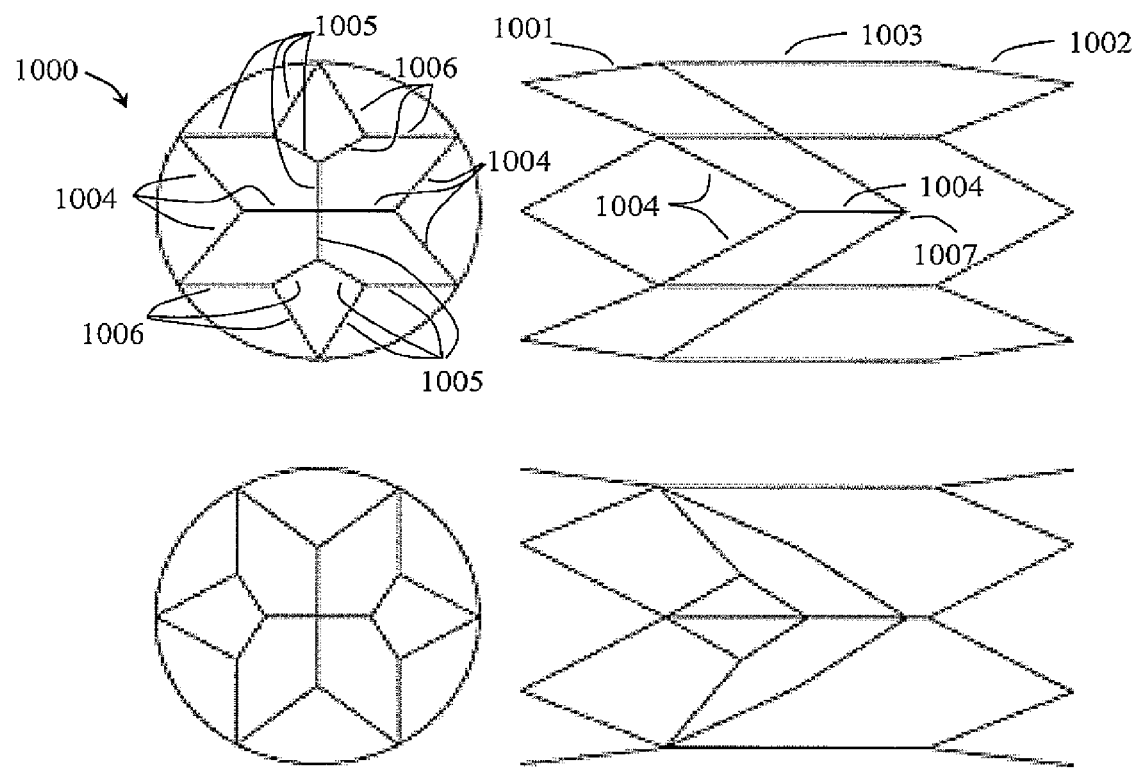

Device 1000 is shown in FIG. 54 where two sets of three differentially shaped filter elements 1004, 1005, and 1006 in combination with a support frame comprising a proximal hoop 1001, a distal hoop 1002 and a plurality of connector struts 1003 extending between 1001 and 1002. The six filter elements extend towards a central apex 1007 that has only four filtration struts connected to it. This reduces obstruction to blood flow at the apex and helps to prevent the formation of thrombus formation and/or fibrin growth. Filter elements 1004 and 1005 are connected at the apex 1007 using a biodegradable holder member while filter elements 1006 are connected to filter elements 1005 at a point proximal to the apex 1007.

Figure 55:
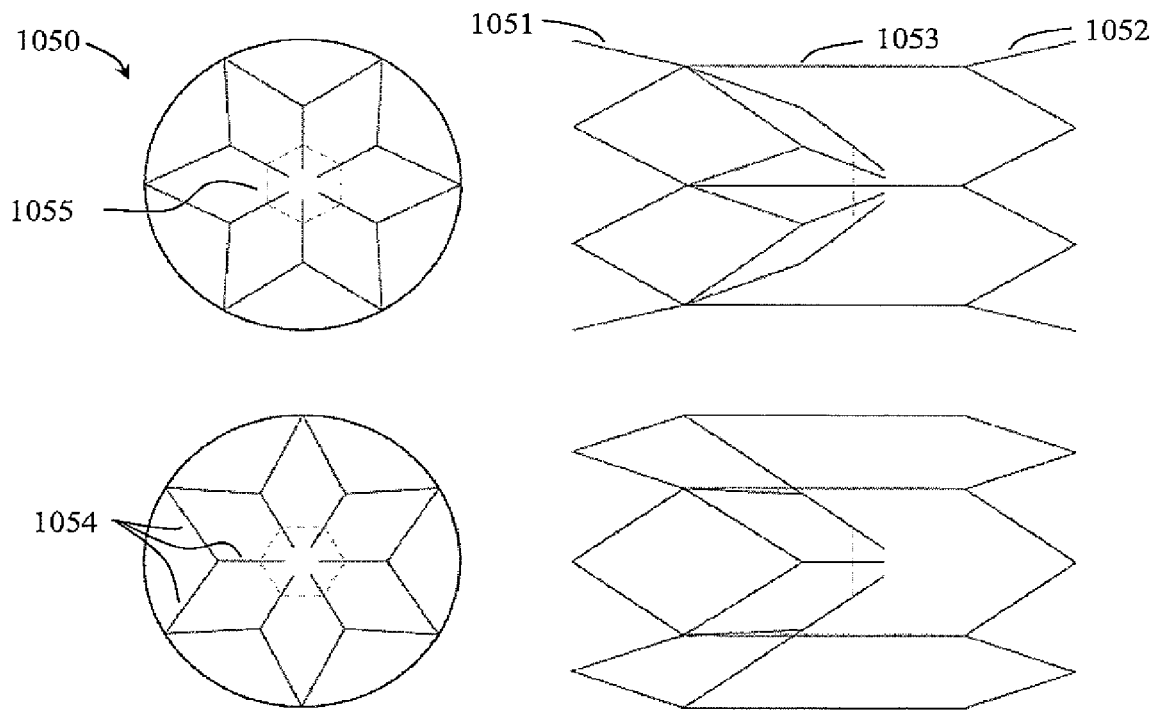

A further embodiment 1050 is shown in FIG. 55 where a plurality of six y-shaped filter elements 1054 are provided with eyelets positioned at a point proximal to their distal end. A biodegradable holder member 1055 is threaded through the eyelets and is configured such that the distal ends of the filter element 1054 do not form a central apex leaving a central opening with filter element protrusions extending centrally from the position of the holder member 1055. The filter elements are provided in combination with a support frame comprising a proximal hoop 1051, a distal hoop 1052 and a plurality of connector struts 1053 extending between 1051 and 1052. This design provided minimal obstruction to the blood flow at the apex thereby preventing the build up of fibrin growth and thrombus at the apex and offers further benefits in that the filter elements do not make contact with one another in the vicinity of the apex. At the time of conversion, the biodegradable holder 1055 will break apart and the likelihood of the filter elements being connected together by fibrin and/or thrombus growth is greatly reduced by having sufficient distance between them in the filtering configuration.

Figure 56:
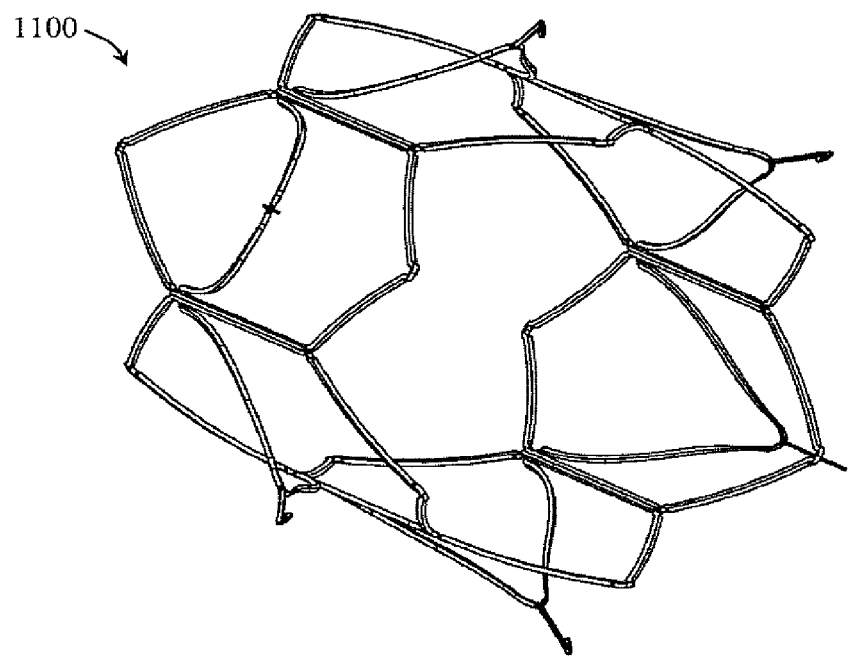
FIG. 56 is a perspective view showing a further device.
Figure 57:
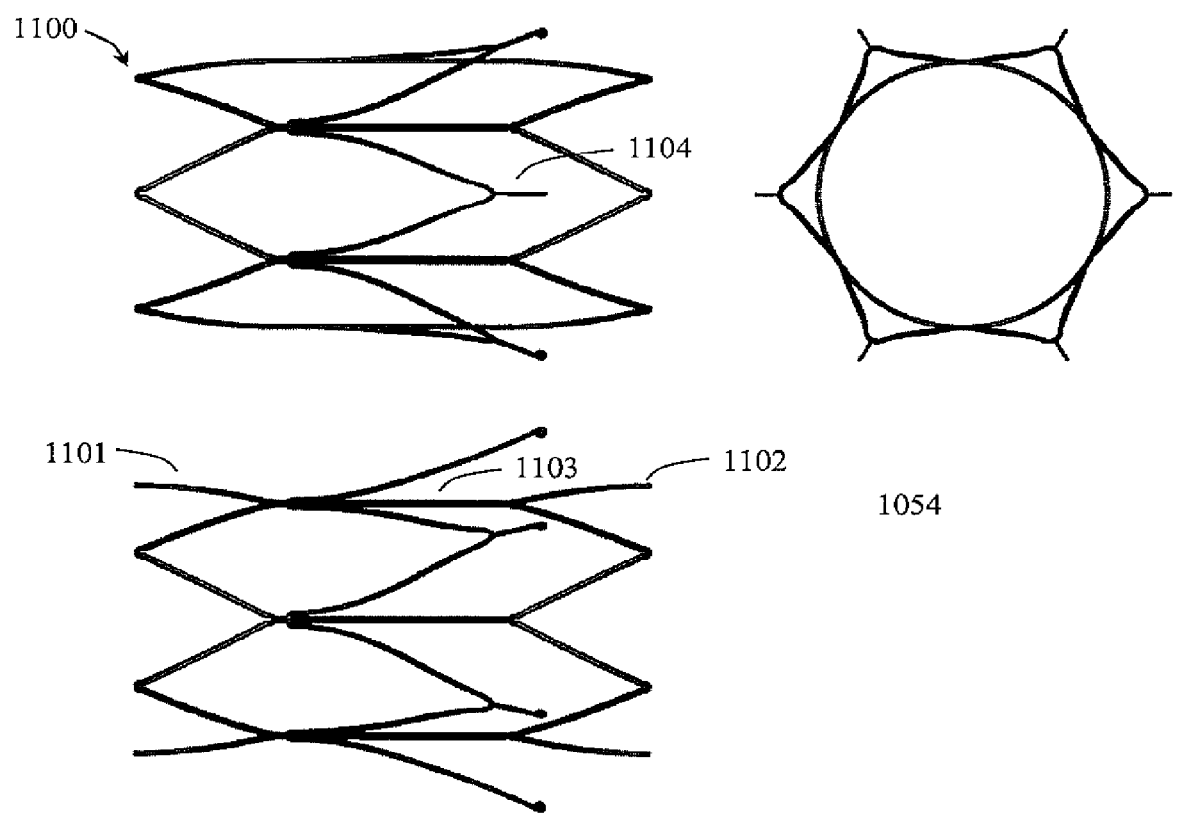
FIG. 57 shows a splayed-out position of its filter elements.
Figure 58:
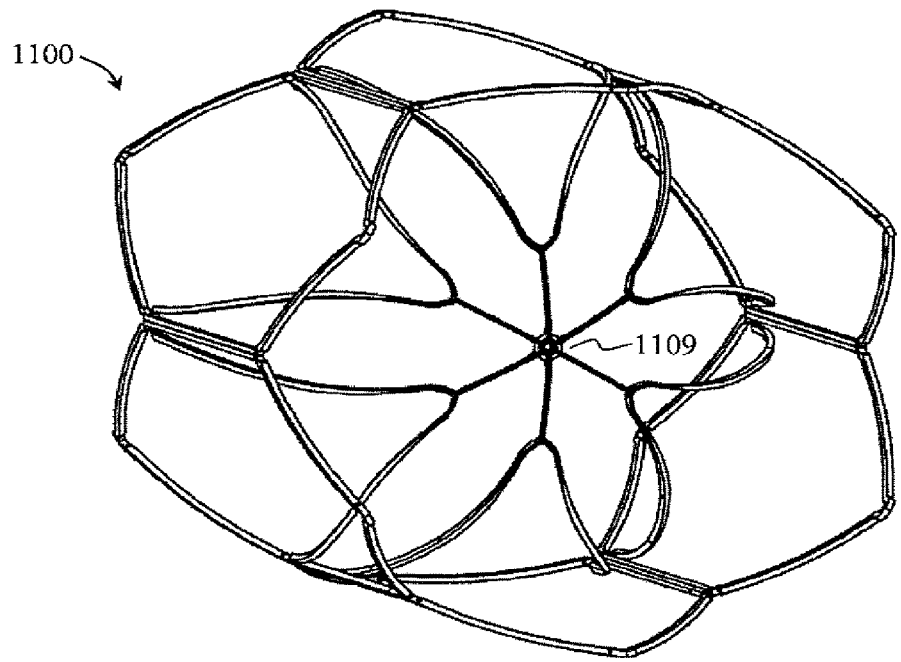
FIG. 58 is a perspective view of the device with its filter closed.
Figure 59:
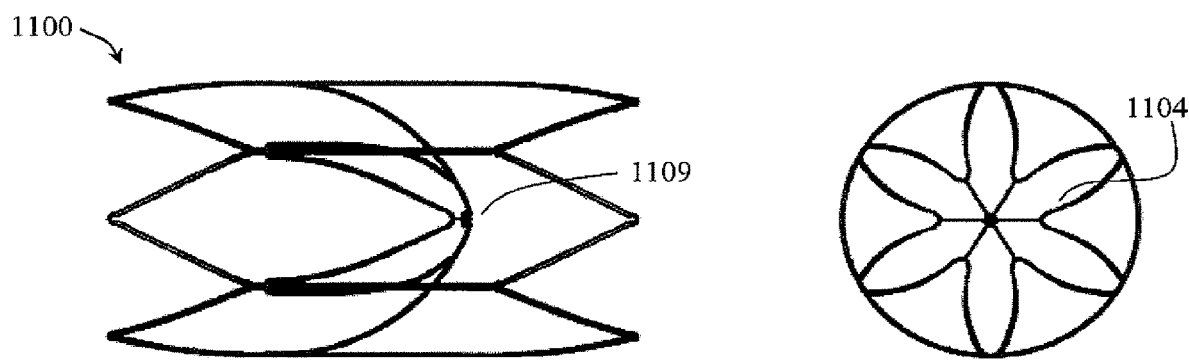
FIG. 59 is a set of side views and an end view also showing the device with the filter closed.
Figure 59:
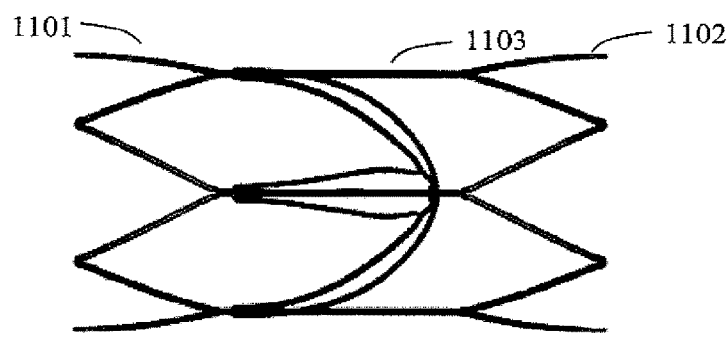
Figure 60:
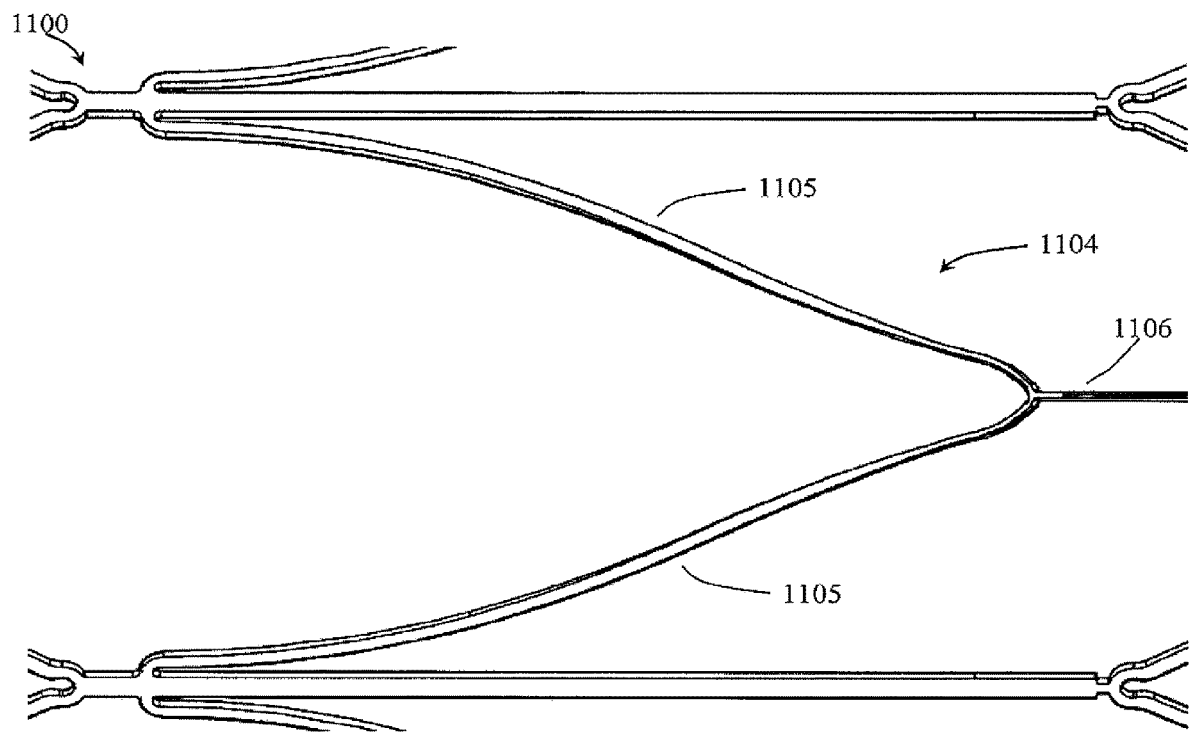
FIGS. 60 and 61 show in more detail connection of a filter element to the support and a filter element at its apex.
Figure 61:
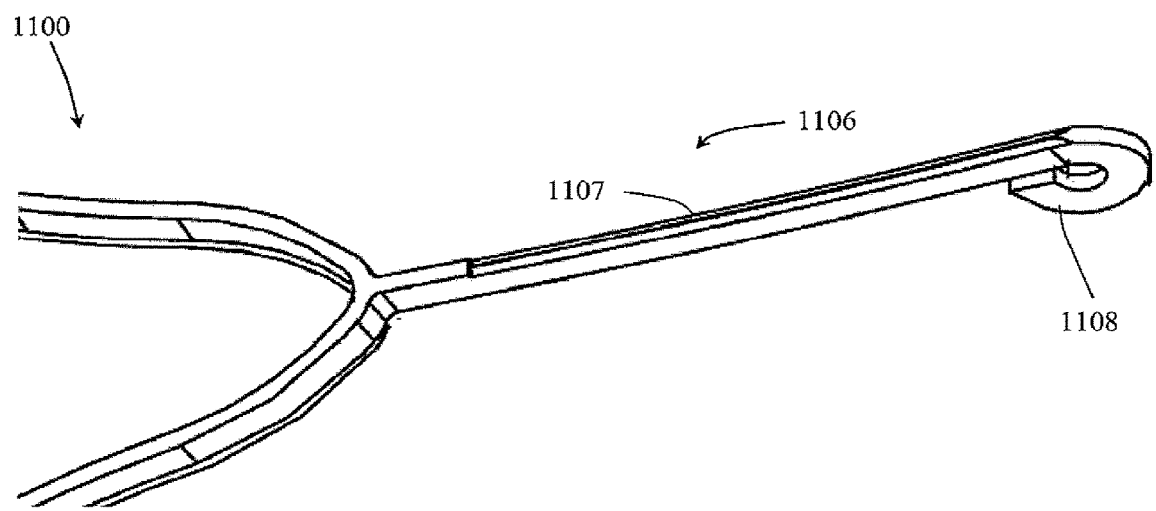
Figure 62A:
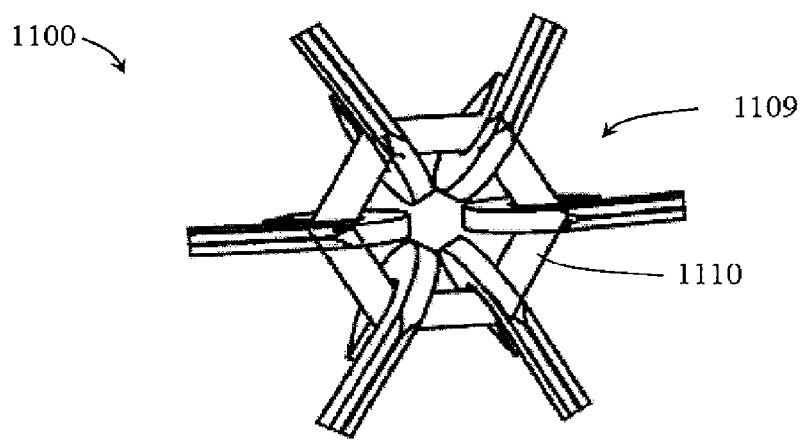
FIG. 62 shows the apex.
Figure 62B:
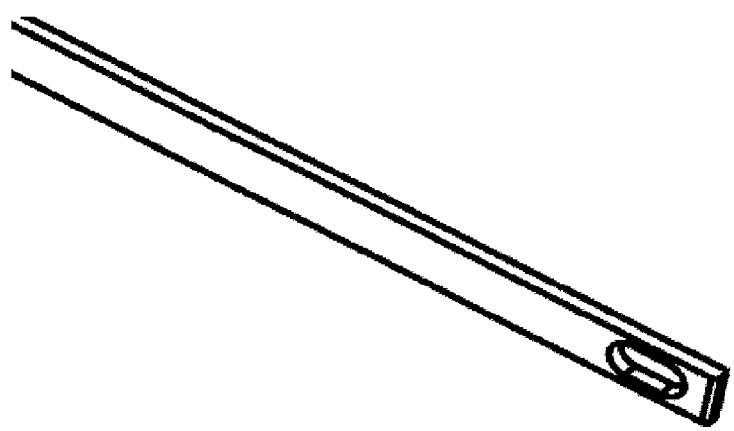
Figure 62C:
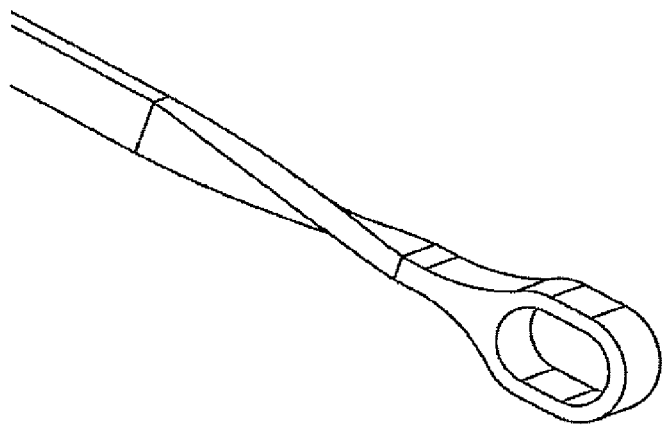
Figure 63:
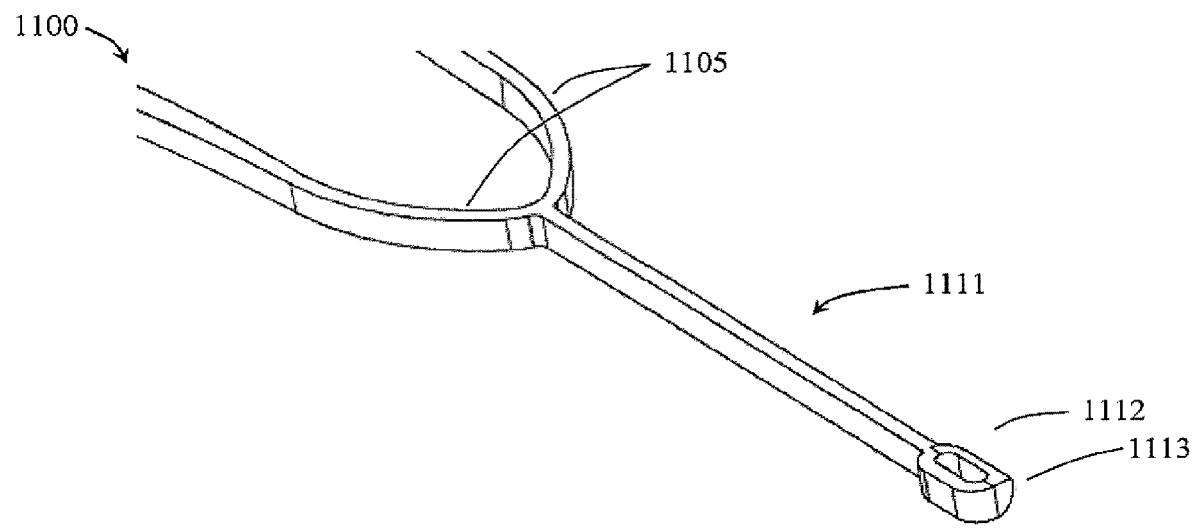
FIG. 63 is a perspective view of the distal end of a filter element and FIG. 64 shows it when twisted.
Figure 64:
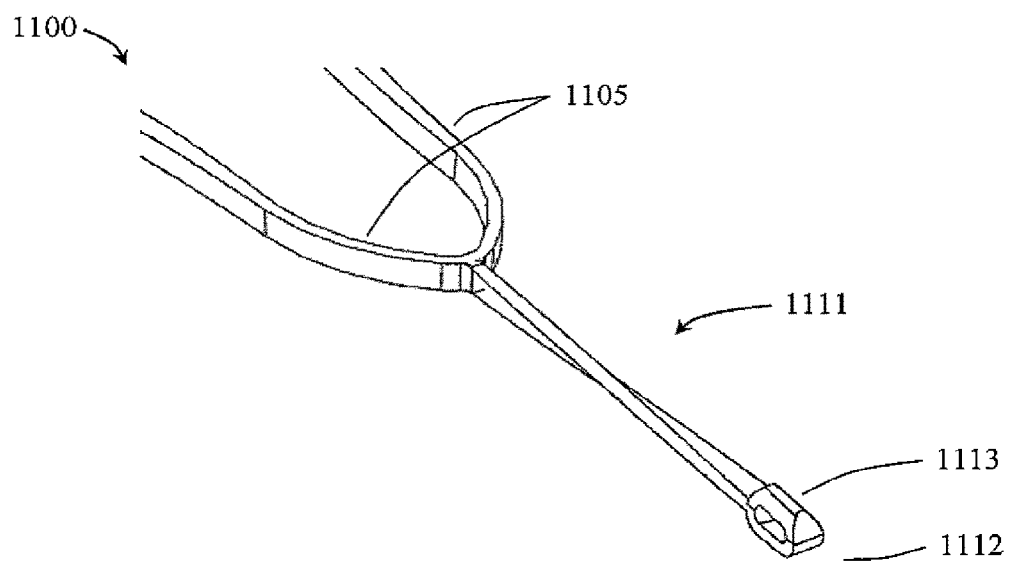
Figure 65:
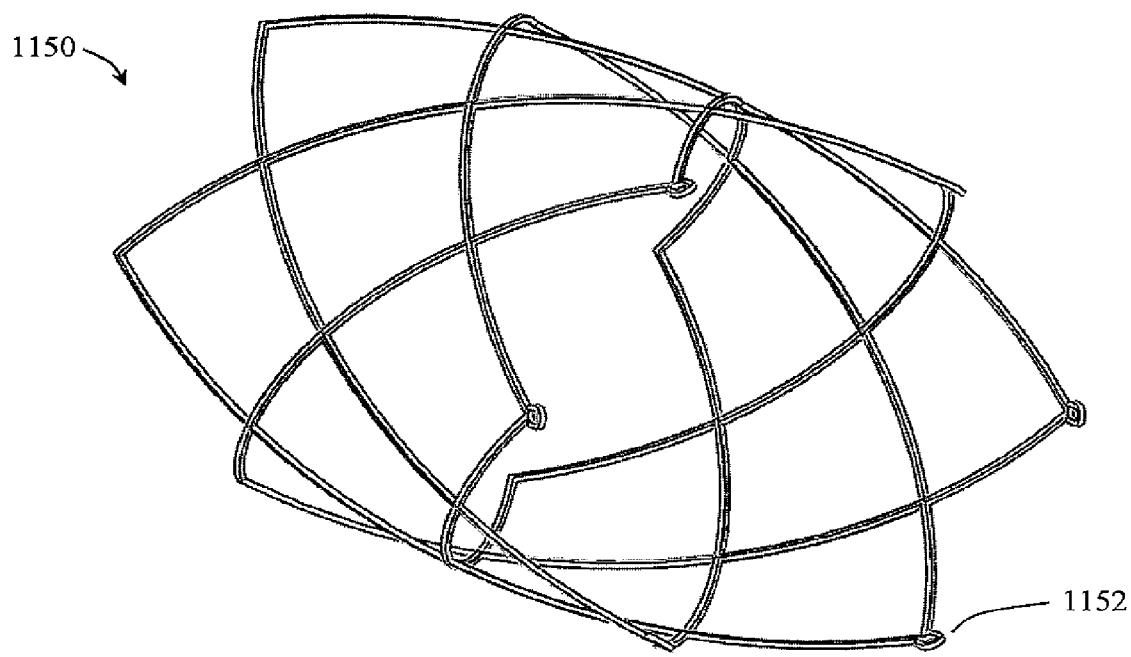
FIG. 65 is a perspective view of an alternative filter device.
Figure 66:
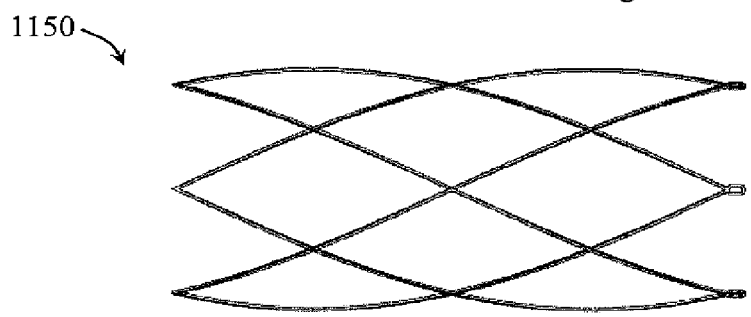
FIG. 66 is a pair of side views and an end view of the device with the filter open.
Figure 66:
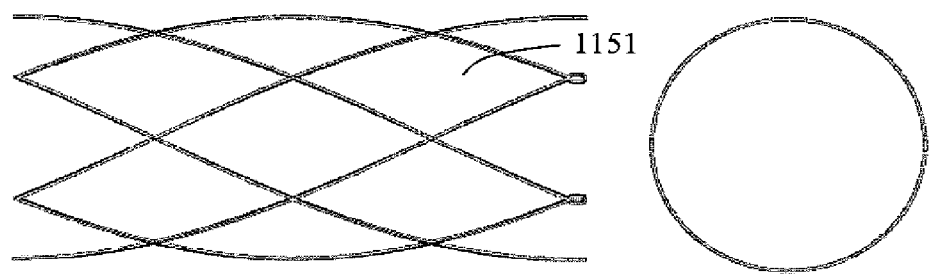
Figure 67:
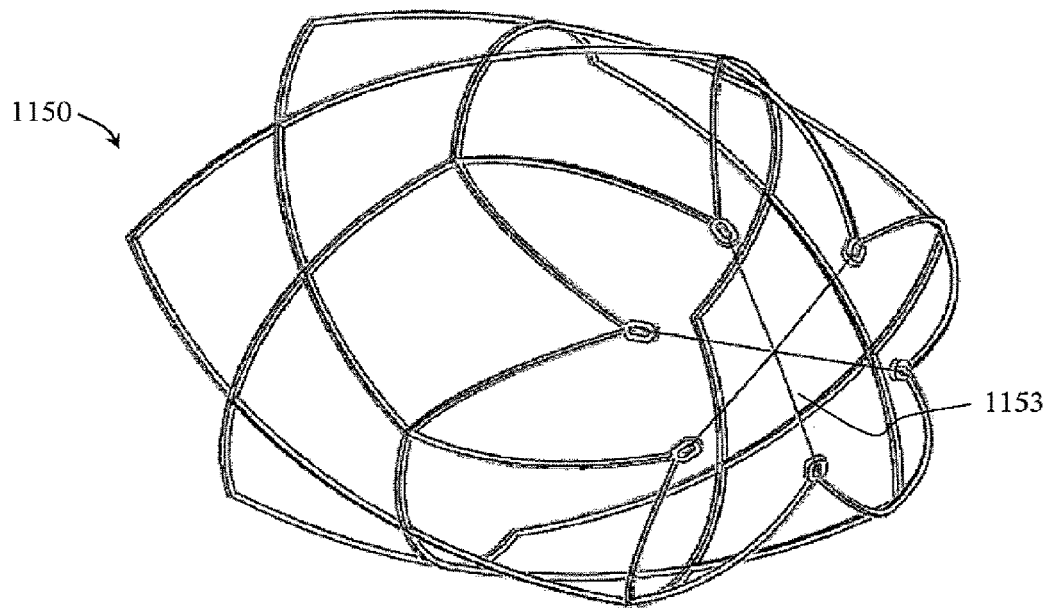
FIG. 67 is a perspective view showing it with the filter closed.
Figure 68:
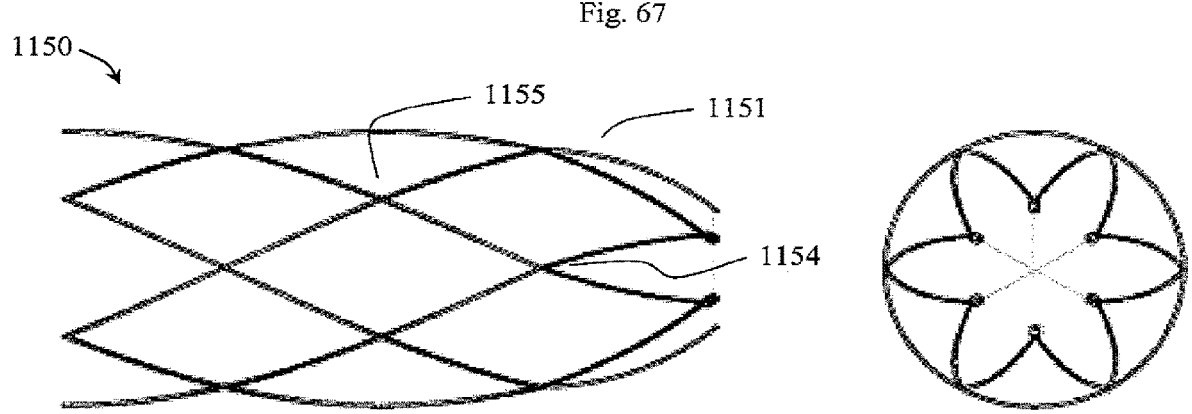
FIG. 68 is a set of views also showing it with the filter closed.
Figure 68:
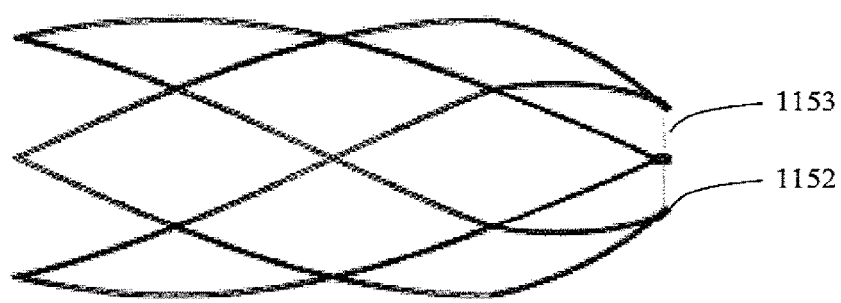

Shown in FIGS. 56 to 64 is a preferred embodiment 1100. Device 1100 comprises a proximal support 1101, and distal support 1102 and a plurality of connector struts 1103 extending between the supports 1101 and 1102. Filter elements 1104 are flared radially outwardly in the open configuration as shown in FIGS. 56 and 57 and extend radially inwardly towards a central apex 1109 where they are held together using a biodegradable holder member 1110 as shown in FIGS. 58, 59 and 62. Filter elements 1104 are constructed with a wider strut thickness at their proximal ends where they are connected at or near the distal peaks of the proximal support hoop 1101. The circumferential thickness of the proximal segments 1105 of the filter elements 1104 may taper down to a reduced thickness as the two segments converge into the distal segment 1106 forming a y-shaped filter element. It is appreciated that the thickness may be constant for a length before tapering or that it may be constant for the full length of the proximal segments and that the thickness of the distal segment may be constant or taper. Alternatively the thickness of the proximal and distal segments may be equal or the thickness of the distal segment may be greater than that of the proximal segment. Preferably, the thickness of the proximal segment is greater such that it applies greater force to the distal segments during opening and that the distal segment springs or flips back from a radially inwardly extending position to a radially outwardly extending position—such a design aids the filter element to overcome endothelial growth at the vessel wall with tips that will break away from any thrombus and or fibrin formation at the apex. In the filtering configuration, the filter elements will form a parabolic shape, as shown in FIGS. 58 and 59, even though they are formed with a flare extending radially outwardly in the distal direction when in the unconstrained configuration as shown in FIGS. 56 and 57—this is due to the reduced bending stiffness of the filter arms at their distal ends and provides a clot reception space with greater volume when compared to devices 1, 100, and 200 and maintains a similar or greater volume than that of device 300 while maintaining the more successful filter arm retraction benefits of devices 1, 100, and 200. The reduced bending stiffness of the distal segments also allows a greater arm force to be applied to the proximal segments without increasing the risk of perforation in the unconstrained configuration due to excessive stiffness at the distal segment. A radius is provided where the proximal segments 1105 converge with the distal segments 1106 to ensure that the distal segments do not lie side by side during filtration to prevent obstruction to the blood thereby preventing the formation of thrombus or fibrin growth at the apex. The filter element construction is best shown in FIGS. 60 and 61. FIG. 61 show the distal segment 1106 that may be formed sufficiently thin in the circumferential direction such that less resistance is required to break through thrombus and/or fibrin formation at the apex. The radially outward portion of the distal segment may have a ground or sharpened section 1107 to reduce the resistance force to break through growth while maintaining bending stiffness of the distal segment if a greater circumferential thickness was desired. The distal segment 1106 may be wound in a nearly closed hook shape to form an eyelet 1108 for reception of a holder member 1110. During manufacturing the eyelet could be bent backwards before placing a continuous band, ring, or flexible holder member 1110. After release of the eyelets, the holder would be secure in place. In another embodiment, an opening is machined/laser cut/etched into the sidewall of the filter element strut as shown in FIG. 62a, this most preferred embodiment offers an even lower profile to the device shown in FIG. 61 thereby providing less obstruction to blood flow while maintaining the thin width in the circumferential direction to aid in breaking through fibrin and/or thrombin formation if present. Alternatively, an eyelet may be formed with the reception space facing in the radial direction as shown in FIG. 62b where the eyelets are twisted 90 degrees before being tied together in a central apex. In another embodiment, an eyelet 1112 with the reception space formed in the radial direction is twisted during assembly and supplied with a ground or sharpened portion 1113 facing radially outwardly in the filtering configuration and circumferentially in the unconstrained configuration. This provides an additional torsional force to aid in breaking away for thrombus and/or fibrin growth at the apex while positioning the sharpened edged of the eyelet 1112 away from the vessel wall in the unconstrained configuration to prevent contact with the vessel wall which may cause vessel trauma or even perforation—however this is considered unlikely provided the sharpened edge is sufficiently blunt.

FIGS. 65 to 68 show a further embodiment 1150 defined by diamond shaped hoops with eyelets 1152 at the distal peaks of the diamond hoops 1151. An array of filaments 1153 extend between opposing eyelets to hold the distal peaks of the distal diamond hoop more centrally in the lumen, thereby acting as filtration elements. The mid peaks 1154 of the distal diamond hoop (same as the distal peaks of the central diamond hoop) will also extend slightly radially inwardly or at least apply less radial force to the vessel wall than the proximal diamond hoop—this will prevent excessive endothelial growth at the vessel wall thereby allowing the distal diamond hoop to retract fully to the vessel wall upon degradation of the filaments 1153.

Figure 69:
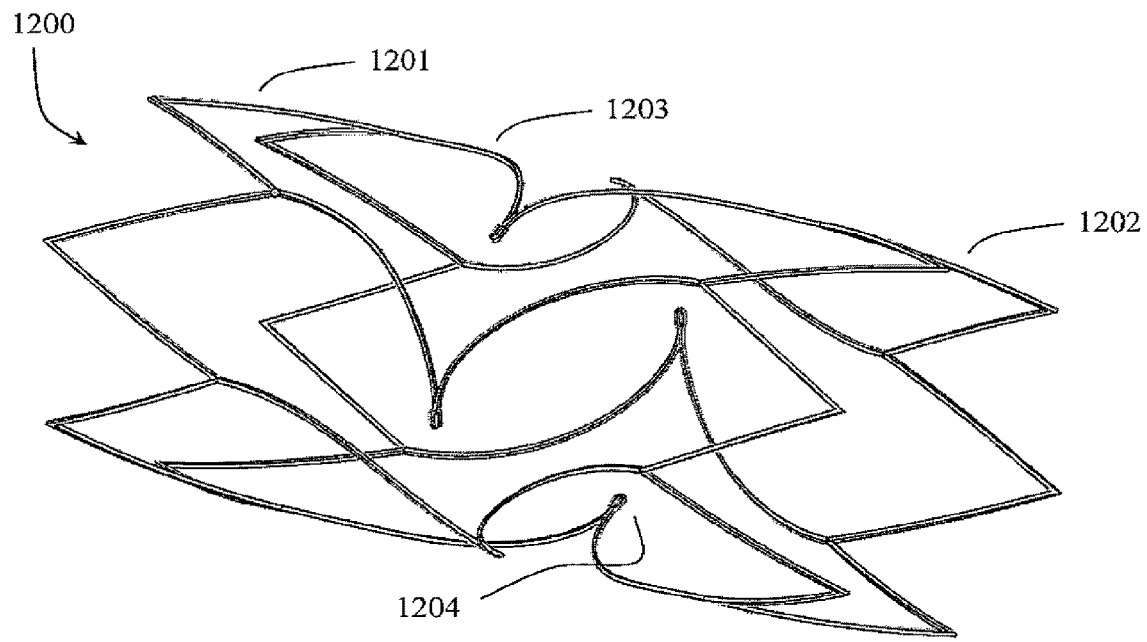
FIG. 69 is a perspective view of a further device, in which filter elements have a twisted configuration when closed.
Figure 70:
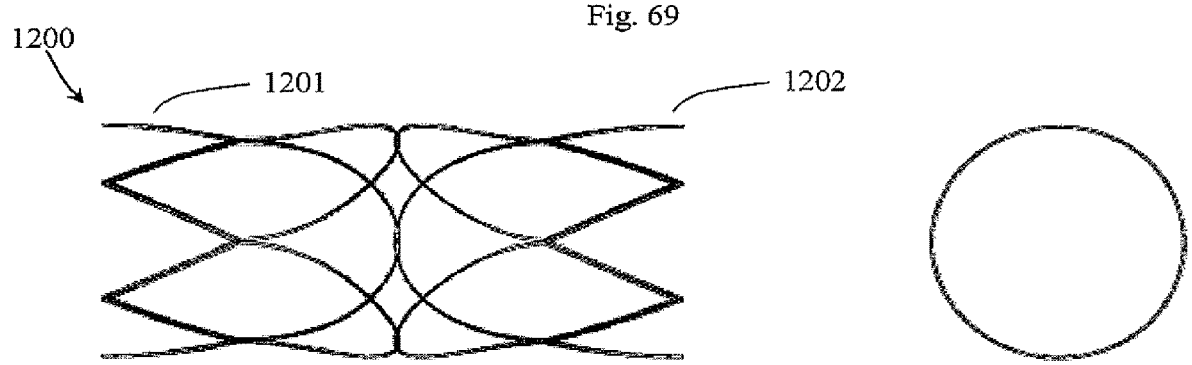
FIG. 70 is a pair of side views and an end view with the filter open.
Figure 70:
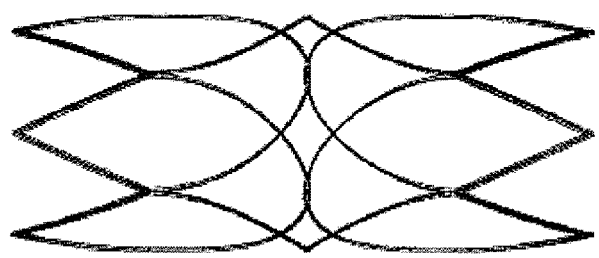
Figure 71:
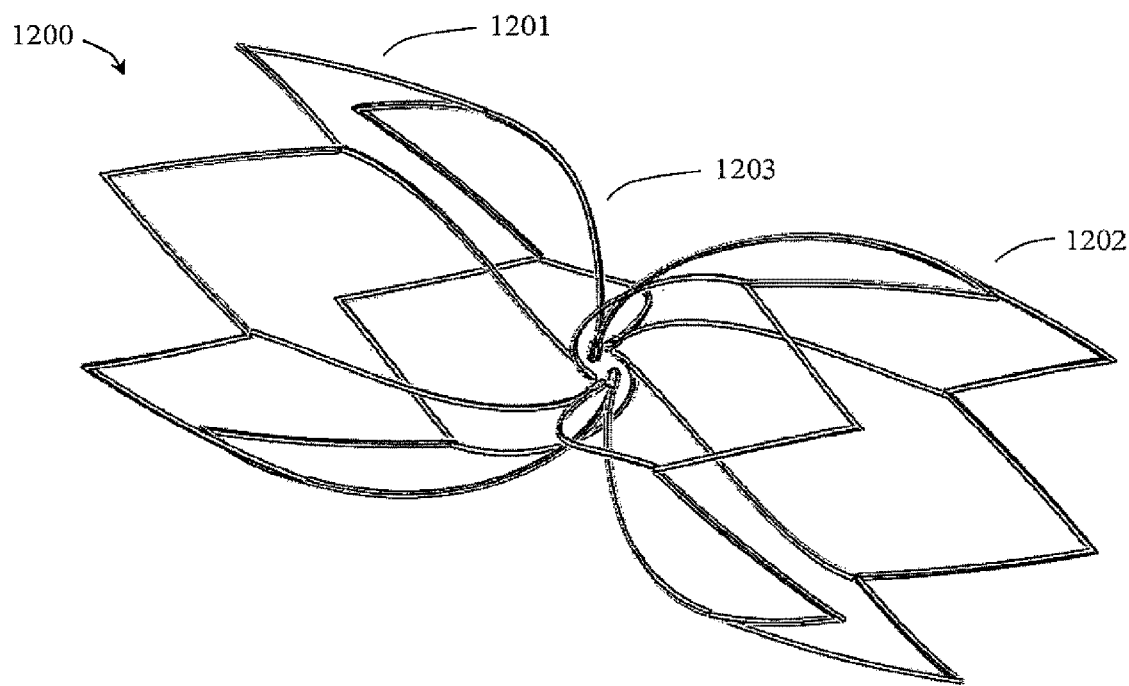
FIG. 71 is a perspective view showing the filter closed.
Figure 72:
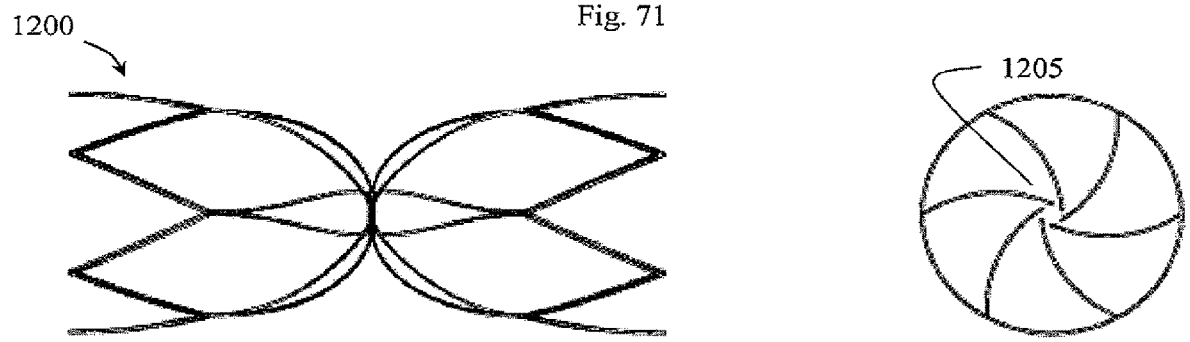
FIG. 72 is a set of views showing the filter closed.
Figure 72:
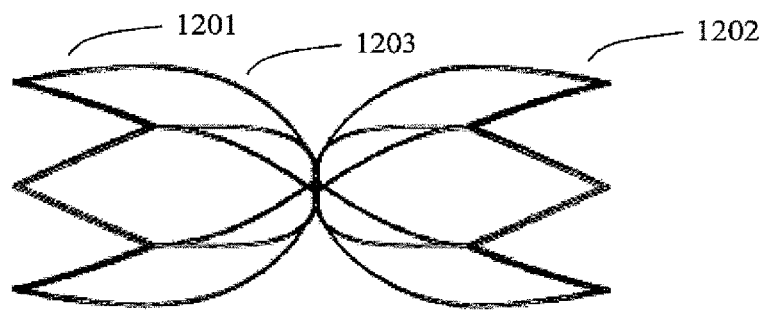
Figure 73:
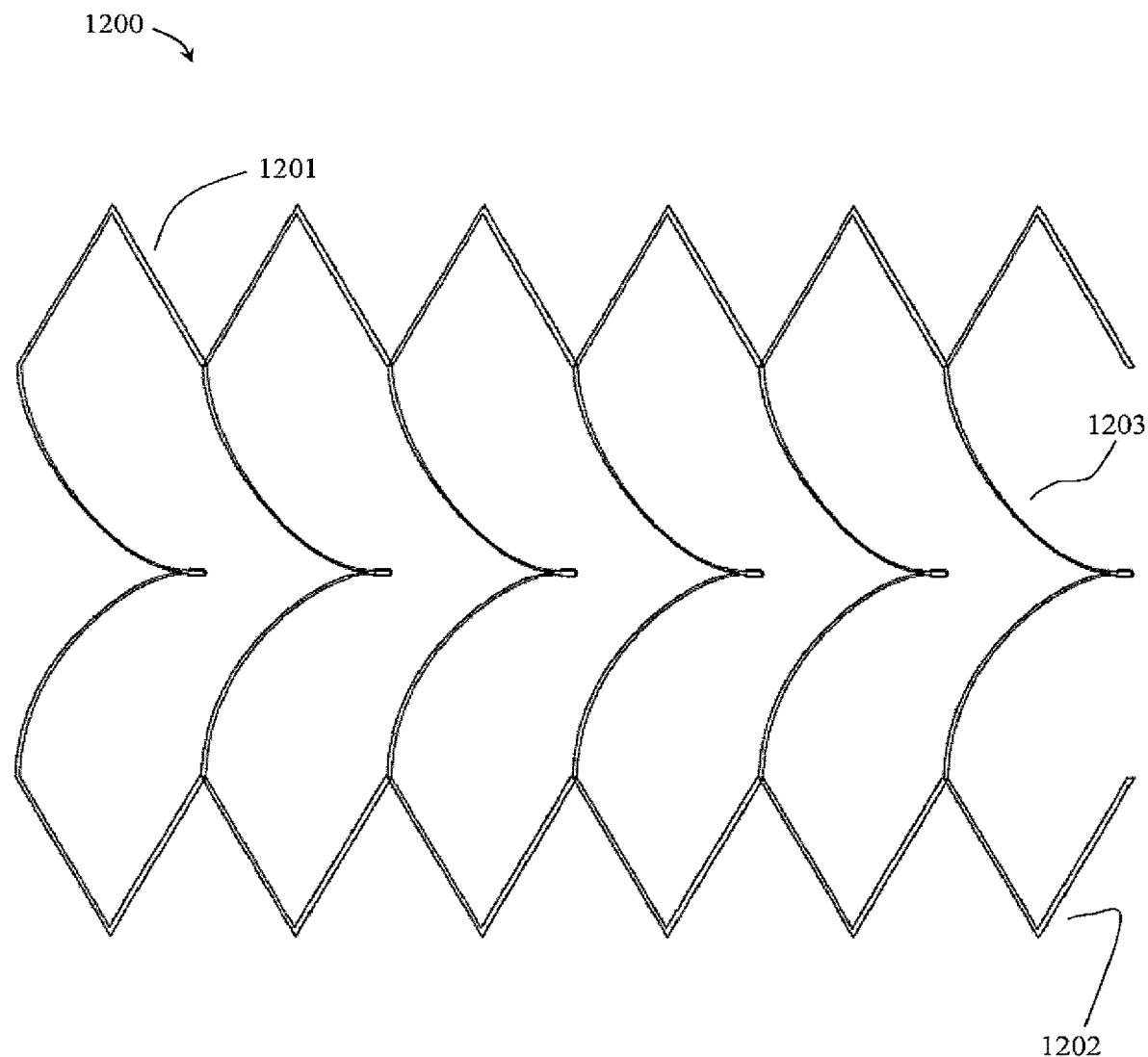
FIG. 73 is a plan view of a cut pattern for manufacturing this device.
Figure 74:
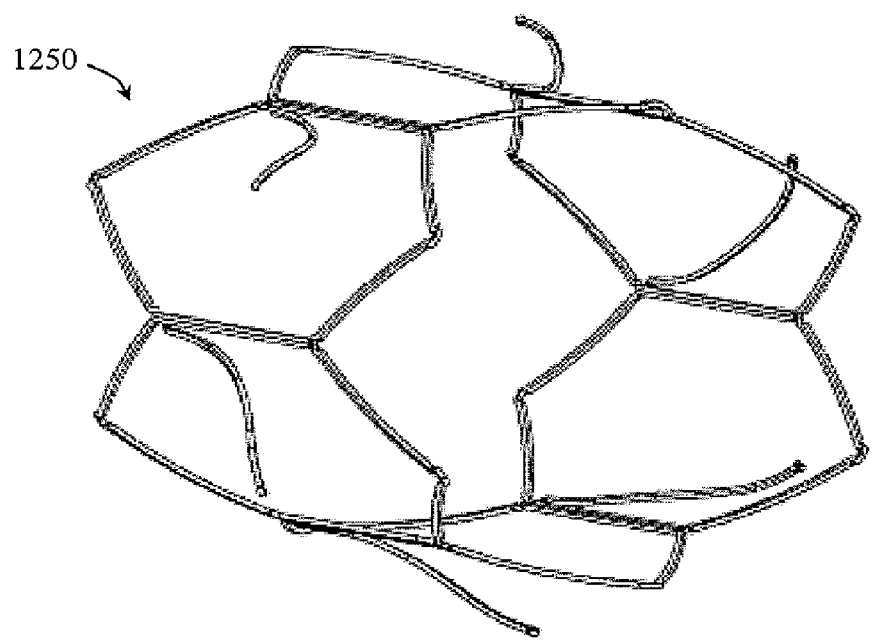
FIG. 74 is a perspective view showing a further device, in this case having filter elements which are directed when relaxed radially outwardly and circumferentially.
Figure 75:
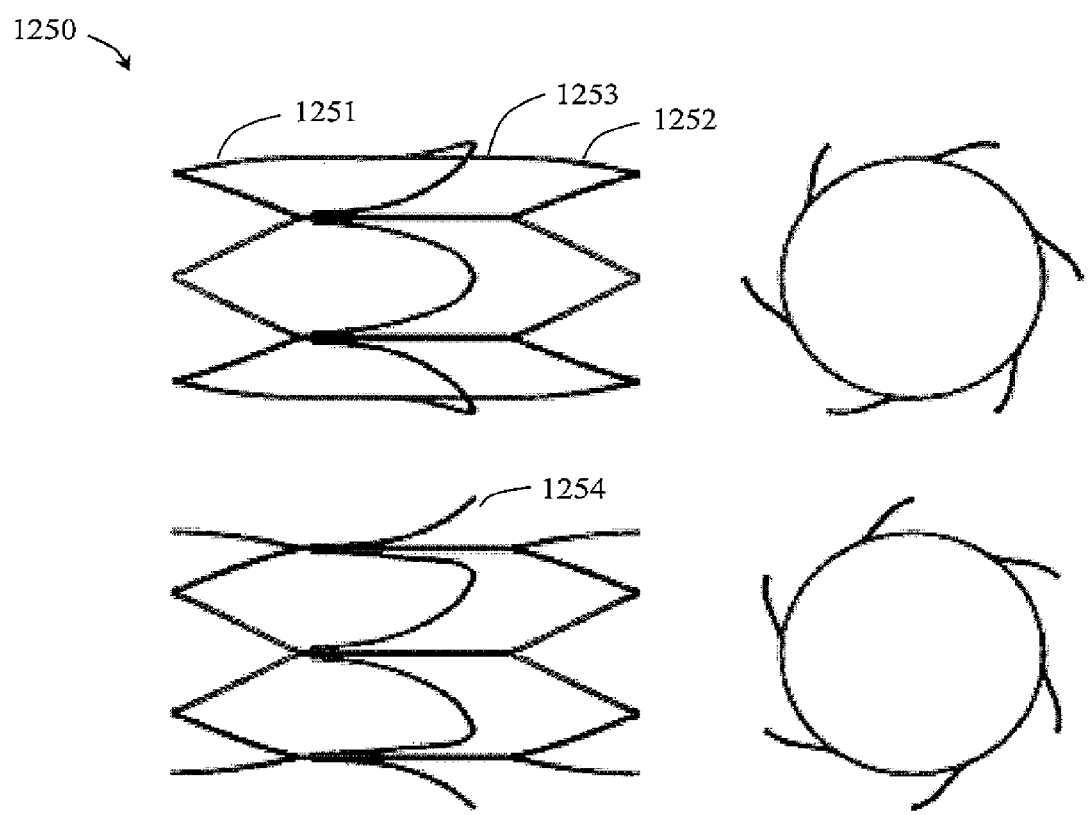
FIG. 75 is a pair of side views and a pair of end views.
Figure 76:
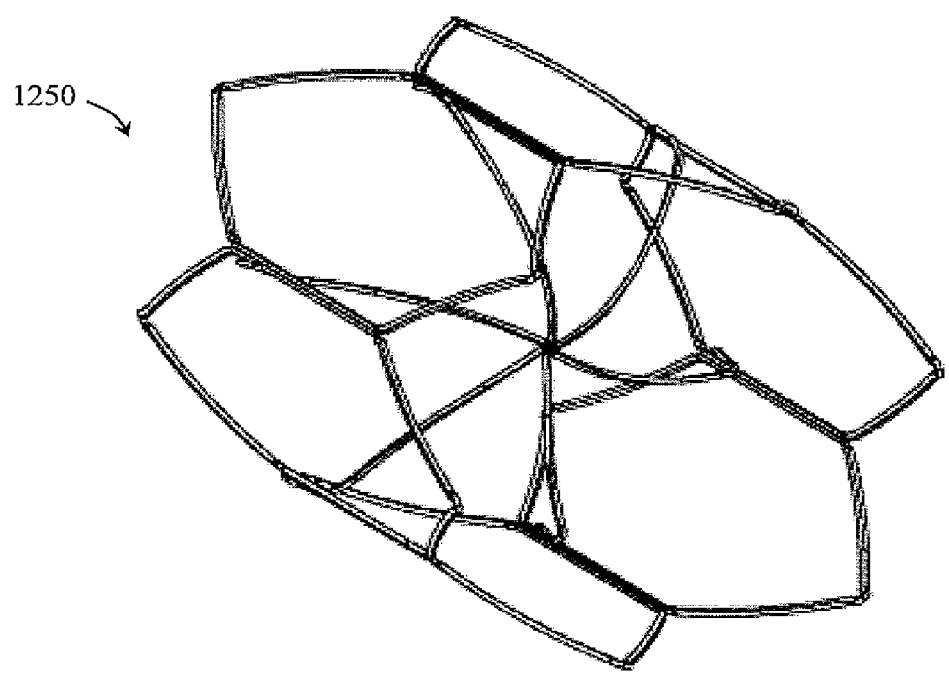
FIG. 76 is a perspective view showing the device with the filter closed.
Figure 77A:
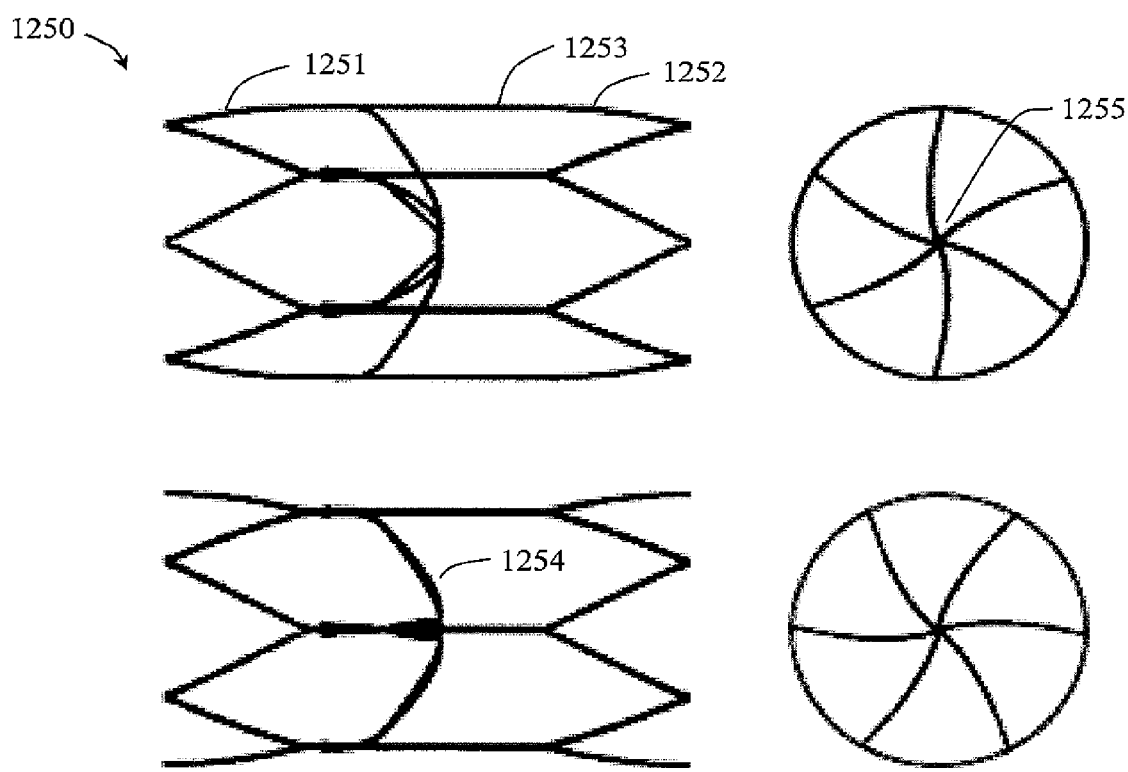
FIG. 77a is a pair of side views and a pair of end views also showing the device with the filter closed.
Figure 77B:
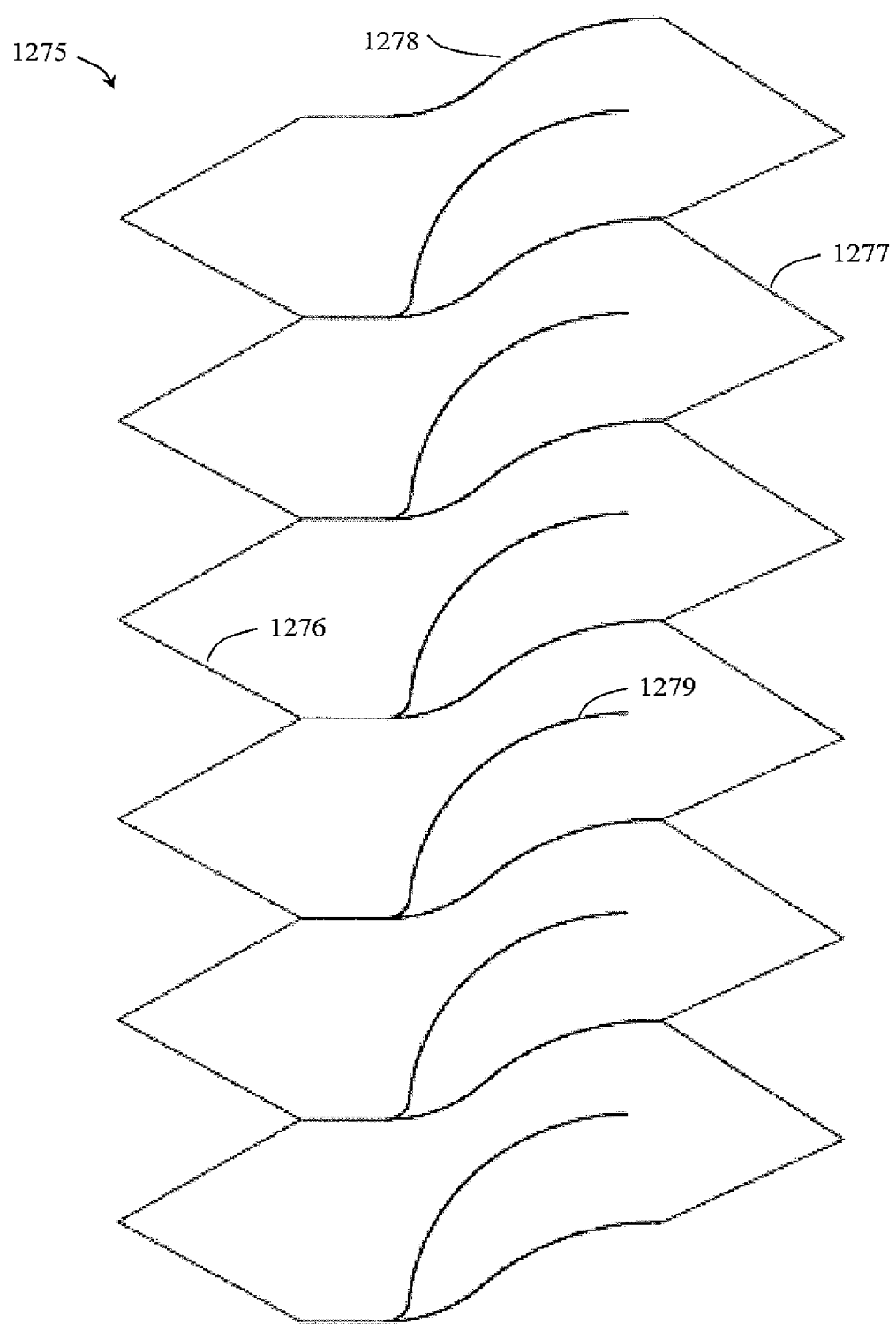
FIG. 77b is a plan view of a cut pattern for manufacturing an alternative embodiment of this device where the peaks of the proximal and distal support hoops are offset.
Figure 78:
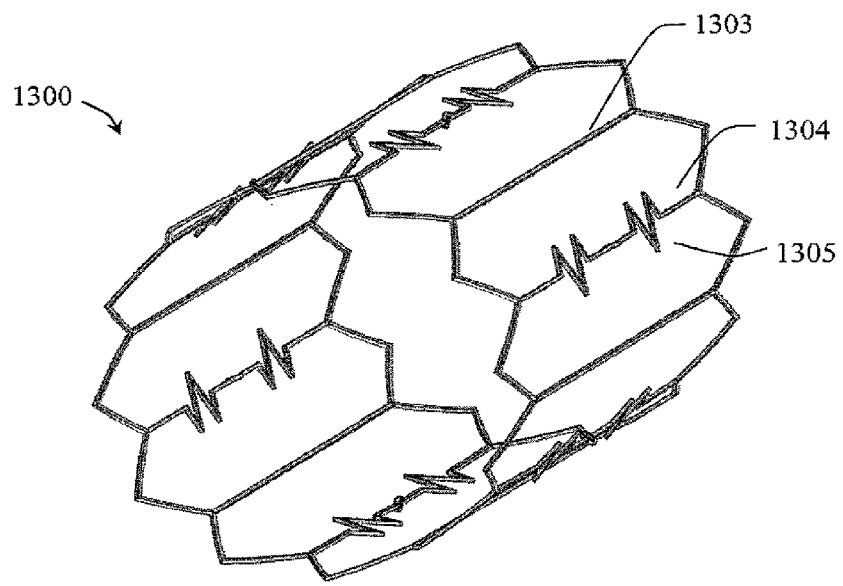
FIG. 78 is a perspective view of a further device of the invention, in this case having filter elements which form an integral part of a support.
Figure 79:
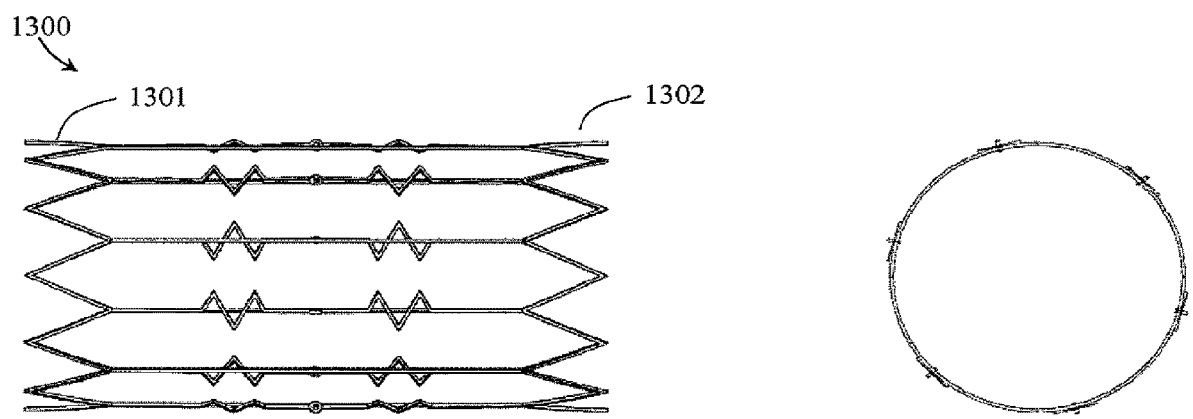
FIG. 79 is a pair of side views and an end view with the filter open.
Figure 79:
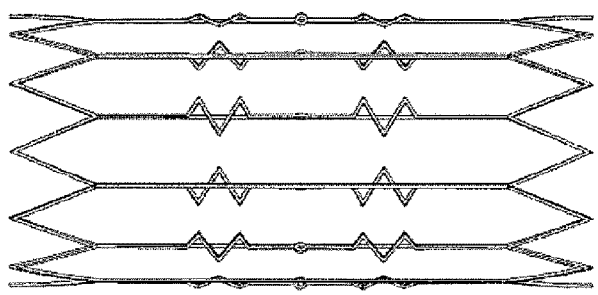
Figure 80:
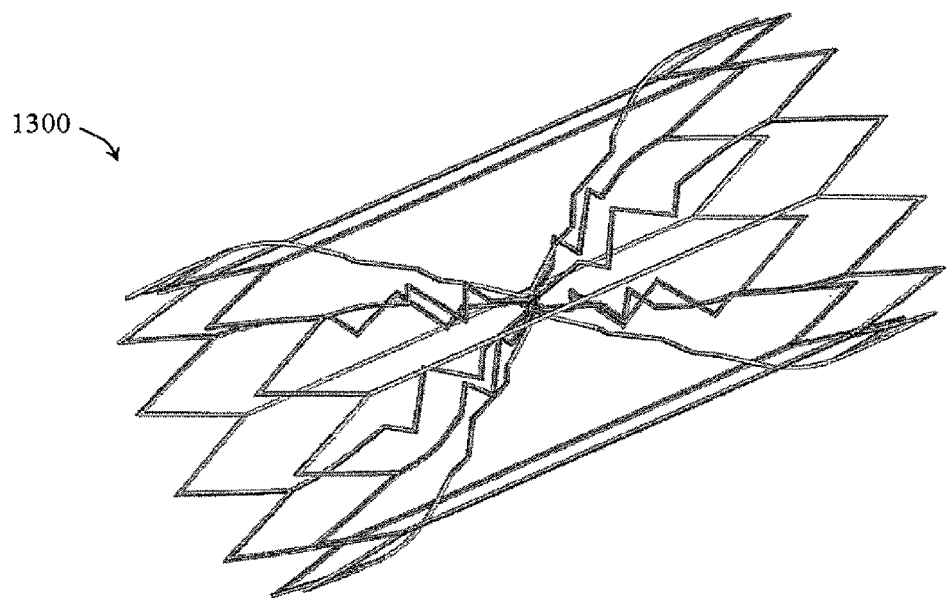
FIG. 80 is a perspective view of the device with the filter closed.
Figure 81:
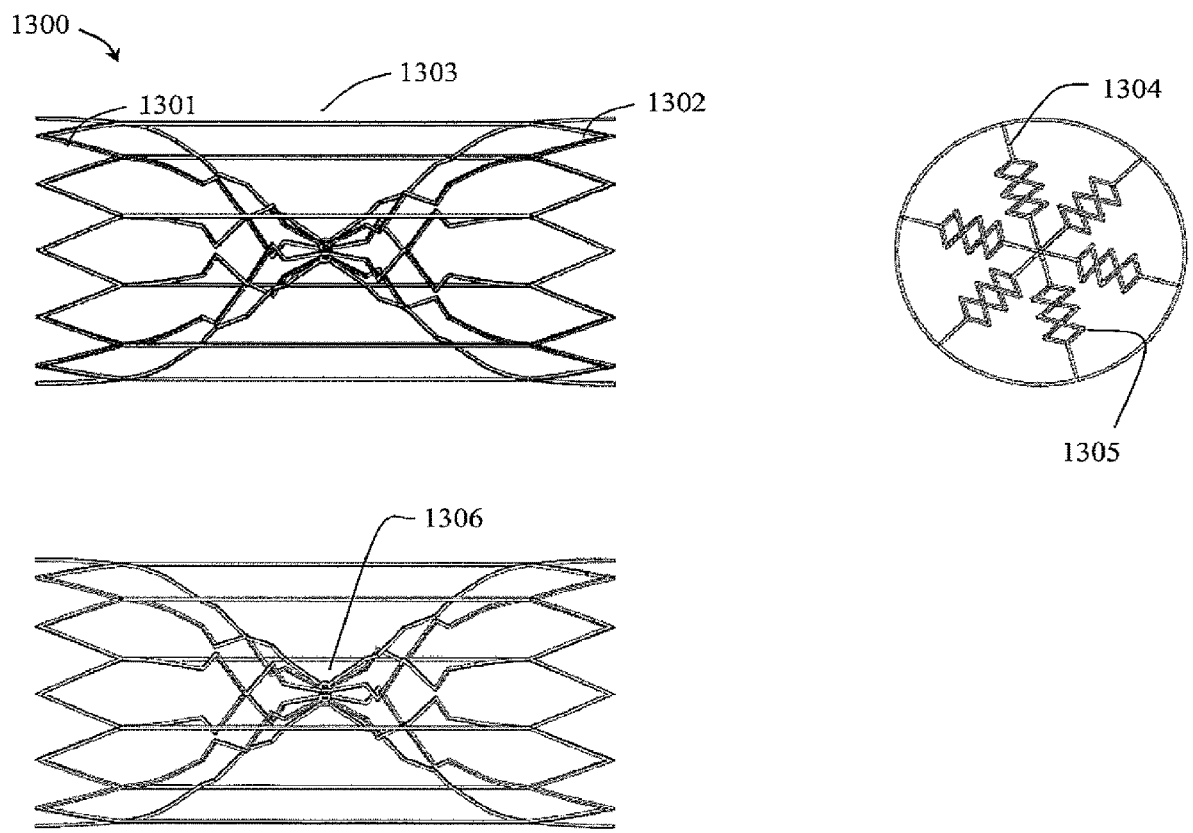
FIG. 81 is a pair of side views and an end view of the device with the filter closed.
Figure 82:
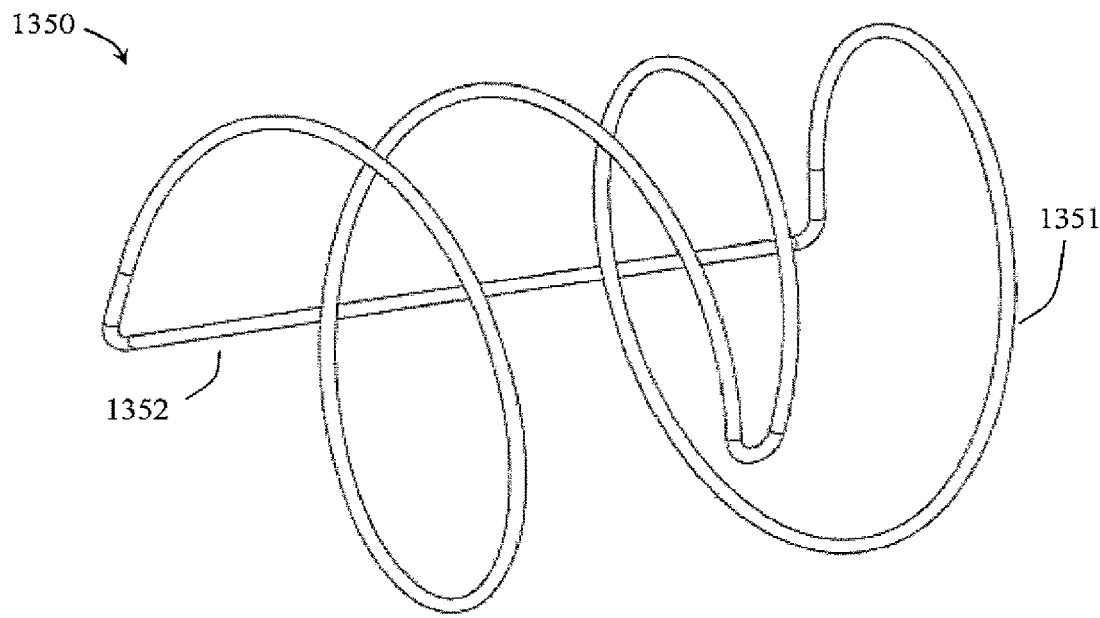
FIG. 82 is a perspective view showing a device of an alternative embodiment with an integral support and filter when the filter is open.
Figure 83:
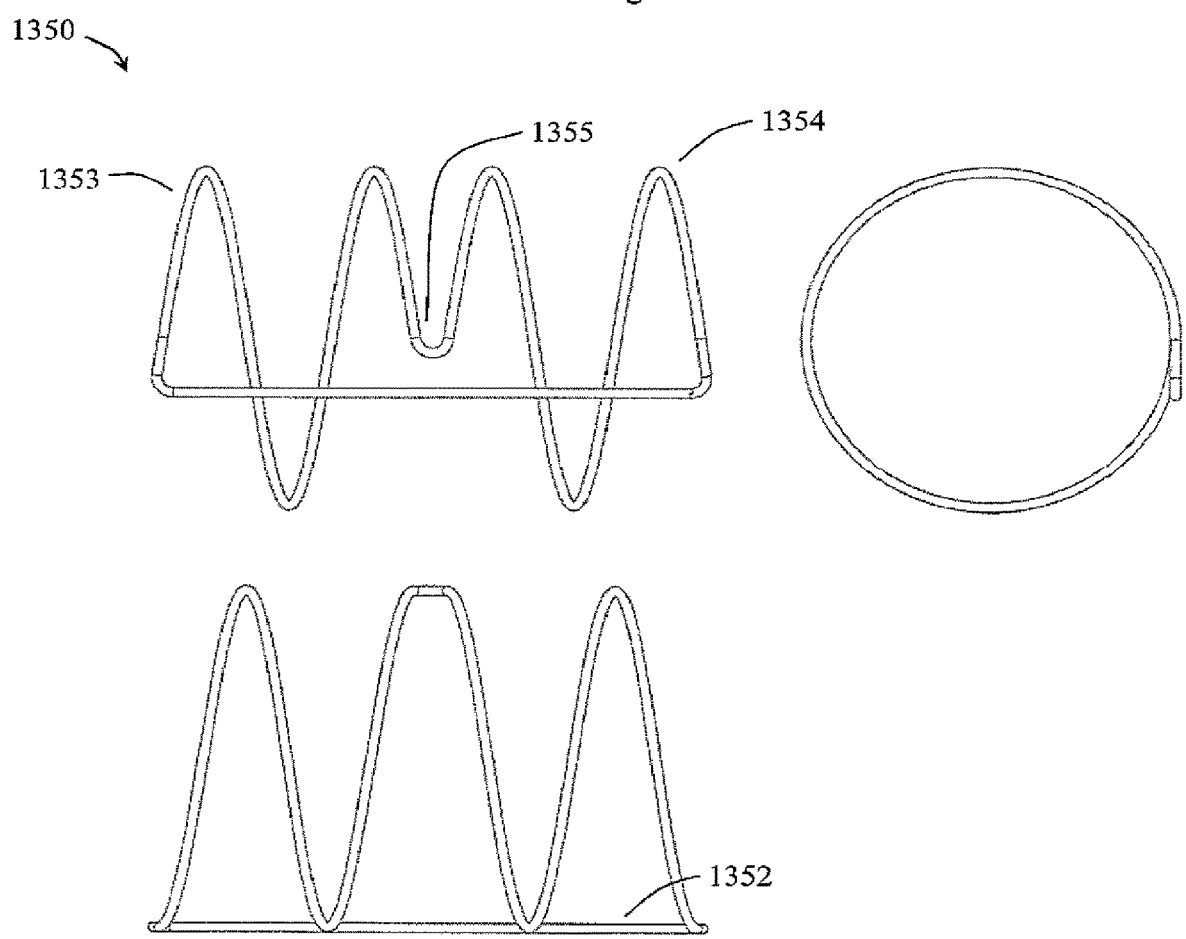
FIG. 83 is a pair of side views and an end view with the filter open.

FIGS. 69 to 73 depict an embodiment 1200 with a proximal support hoop 1201, a distal support hoop 1202 and v-shaped filter elements 1203 extending between the supports 1201 and 1202. The v-shaped filter elements are rotated radially inwardly so that the eyelets 1204 form an apex 1205 and the filter elements form a double filtering cone, the proximal cone pointing distally and the distal cone pointing proximally. This embodiment offers enhanced radial force to overcome endothelial growth at the vessel wall while also providing additional force to break away from growth at the apex as additional filter element strut width can be applied in the circumferential direction when compared to devices 1, 100, 200, and 300 for a similar raw tube outer diameter. This is due to the connector elements of these devices becoming the filter elements of 1200 thereby offering the thickness taken from the filter elements of devices 1, 100, 200, and 300. In addition, the torsional movement about the filter elements axis will further aid in the filter element eyelets breaking away from the apex. A flexible filament is threaded through the eyelets 1204 (not shown) and tied in place. During conversion of the filter elements that move radially outwardly in a plurality of cantilever movements such as that in devices 1, 100, 200, and 300, the eyelets can grip a portion of the filament remaining after the initial break of the degraded filament at a single or multiple location(s) thereby preventing the eyelets from fully separating—the torsional movement of the filter elements 1203 will prevent this from occurring as the eyelets will automatically unthread from the remaining segment of filament. The filtering configuration is shown in FIGS. 69 and 70, the unconstrained configuration in FIGS. 71 and 72, and a developed view (or rolled flat view of the tubular profile) of the laser cut profile is shown in FIG. 73 to show the laser cut pattern that is wrapped cylindrically to cut the device from a tube.

Device 1250 is shown in FIGS. 74 to 77 and is similar to device 1200 in that the filter elements 1254 rotate about the axis of the connecting elements 1253, extending between proximal support hoop 1251 and distal support hoop 1252, when moving from the filtering configuration to the open configuration post degradation of the holder member 1255 at a central apex of the filter cone. The single filter arm design provides a single filtration cone, the arms exerting a torsional force on any thrombus of fibrin growth at the apex if present allowing the filter arms to retract to the vessel wall. The filter elements are curved circumferentially and flared radially outwardly to aid successful retraction to the vessel wall in the presence of endothelial growth as described earlier in the specification. When viewed axially, the filter elements form a spiral shape that aids in reducing growth at the apex by inducing a swirling blood flow in the vicinity of the filter cone. FIG. 77b is a flat pattern view (i.e. rolled out view of the tubular profile) that depicts a further embodiment 1275 similar to 1250 except that the connector elements 1278 extend between distal peaks of the proximal support hoop 1276 and the proximal peaks of the distal support hoop 1277 that are offset from each other. This arrangement allows more space for the filter elements 1279 to extend circumferentially in the unconstrained configuration thereby affording additional torsional movement of the filter elements.

FIGS. 78 to 81 depict a further embodiment where a proximal support hoop 1301 and a distal support hoop 1302 are provided with a plurality of connector struts 1303 extending between every second distal peak of the proximal hoop 1301 and the opposing proximal peak of the distal hoop 1302, and a plurality of filter elements 1304 extending between every other distal peak of the proximal hoop and the opposing proximal peak of the distal support hoop 1302. Filter elements 1304 are supplied with articulations 1305 that allow the length of the filter elements to increase when the filter elements are translated centrally in the vessel to form a central apex, held in place by a biodegradable holder member 1306. This configuration forms a proximal cone pointing distally and a distal cone pointing proximally affording the filter two levels of filtration for enhanced capture efficiency. The articulations may be z, u, s or any other shape that allows the filter element length to increase when the filter element is translated centrally. A zigzag shape articulation is preferred as it would increase the radial force of the filter element during conversion to aid in overcoming endothelial growth and in breaking away from any growth at the apex if present. Articulations on the proximal and distal cone may be mirrored as shown in the end view of FIG. 81 such that the articulations on the distal cone will intercept a clot that has passed through the proximal distal cone. The connector members 1303 should be rigid to prevent bowing when the filter elements are translated centrally for the filtering configuration.

Figure 84:
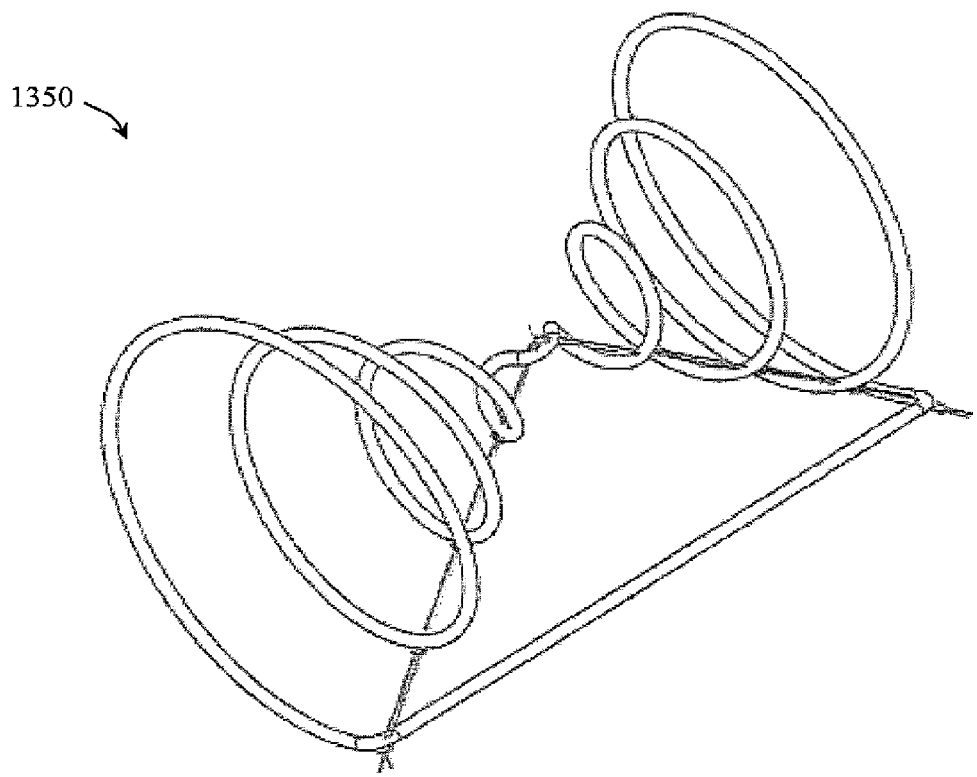
FIG. 84 is a perspective view of the device with the filter closed by winding the combined support and filter to form a double apex at the centre on-axis.
Figure 85:
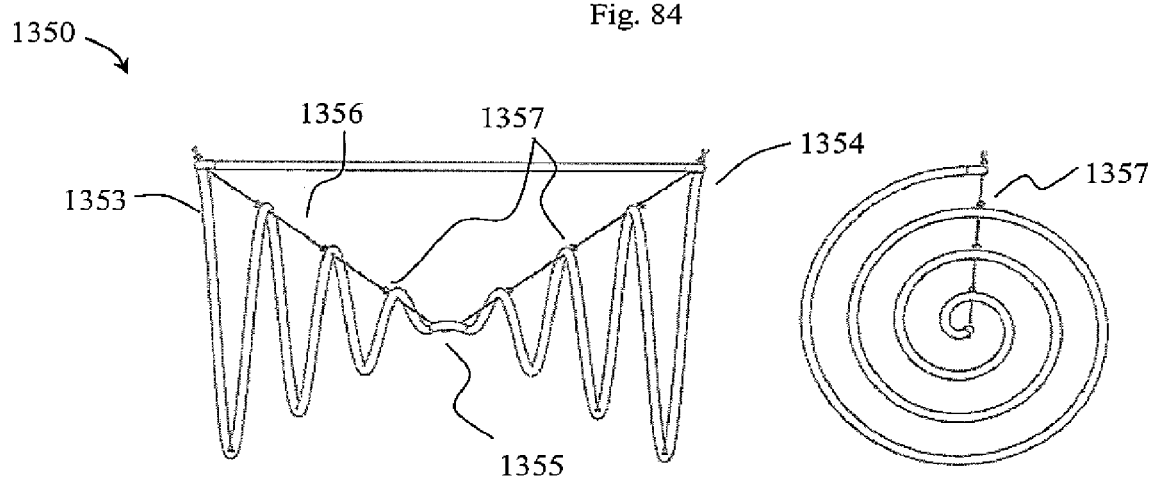
FIG. 85 is a pair of side views and an end view of the device when the filter is closed.
Figure 85:
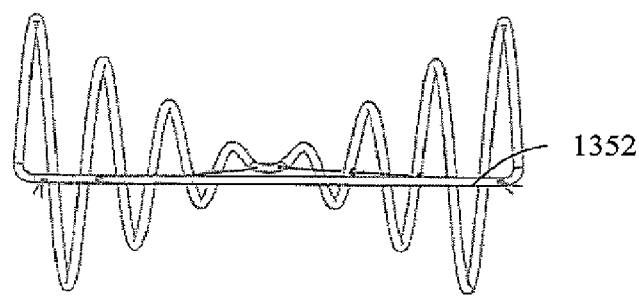
Figure 86:
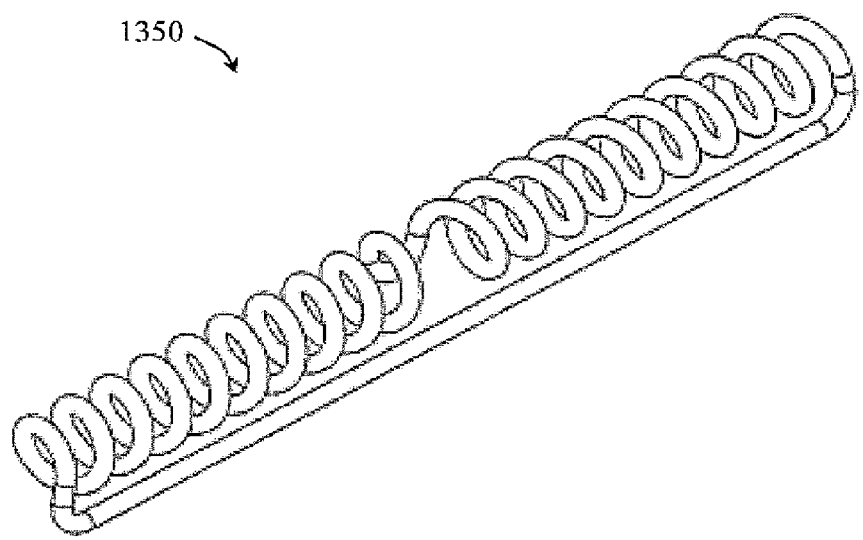
FIG. 86 is a perspective view of the device when wound further into a lower profile for delivery through a catheter.
Figure 87:
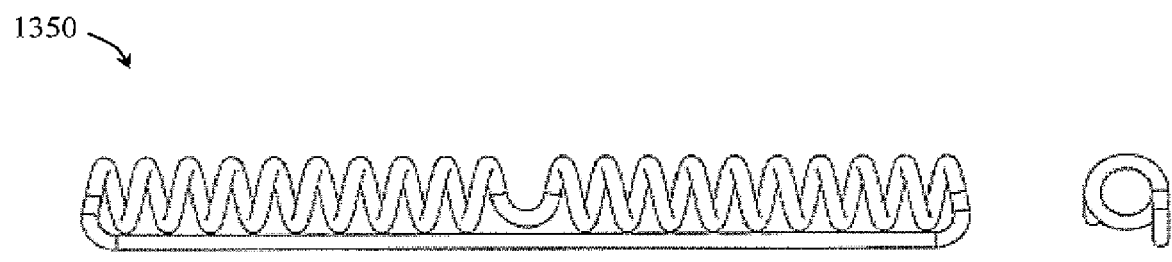
FIG. 87 shows the device in side and end views of the filter wound for delivery.
Figure 87:
Figure 88:
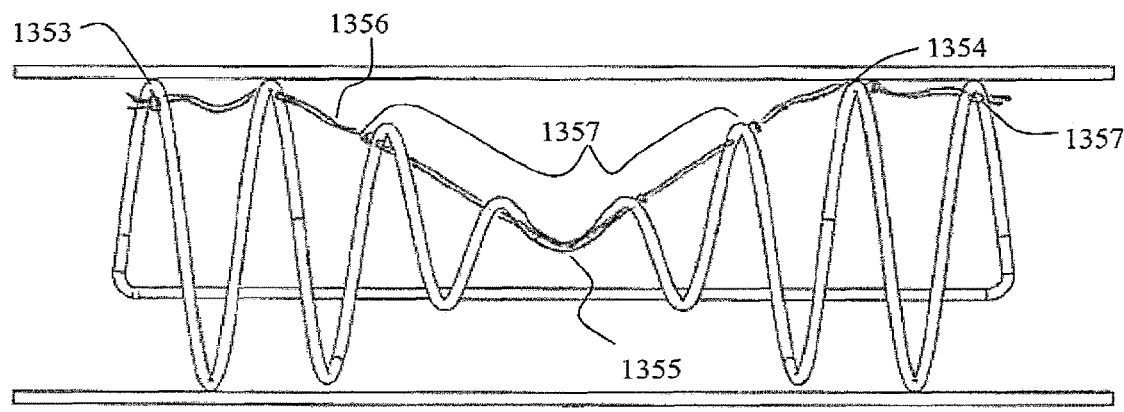
FIG. 88 shows how the filament slackens at the proximal and distal ends of the proximal and distal coils when deployed in a vessel smaller than the unconstrained diameter of the device.
Figure 89:
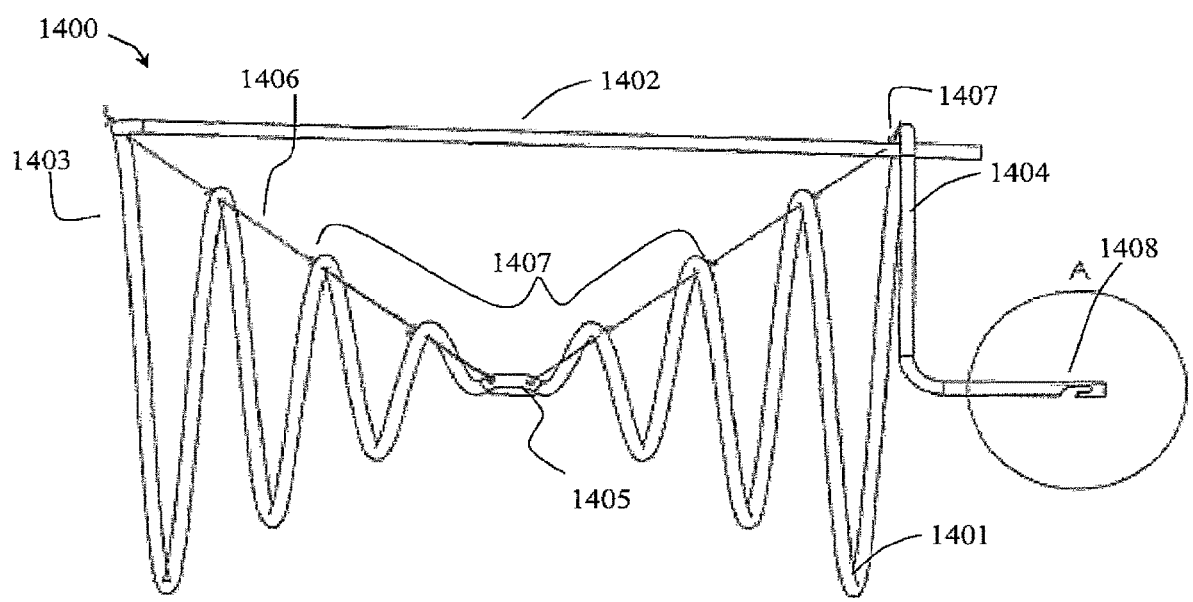
FIG. 89 shows a device which is a variant of the above device, having a hook to facilitate retrieval, a wire, a backbone, a proximal coil, a distal coil, a peak, a filament, knots or stopper features, and a retrieval hook.
Figure 90:
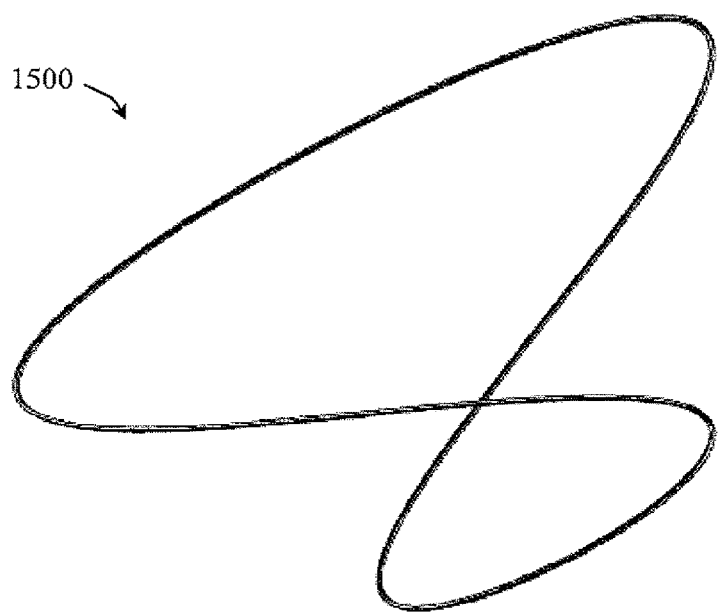
FIGS. 90 to 93 show a further variation, in which there is a parabolic spring support frame with two proximal peaks and two distal peaks in the open configuration, such that when viewed axially the support frame defines a circular shape to contact the vessel wall and is variable in size, through compression, to fit variable vessel sizes and where rigid compressible biodegradable filter elements extend across support struts.
Figure 91:
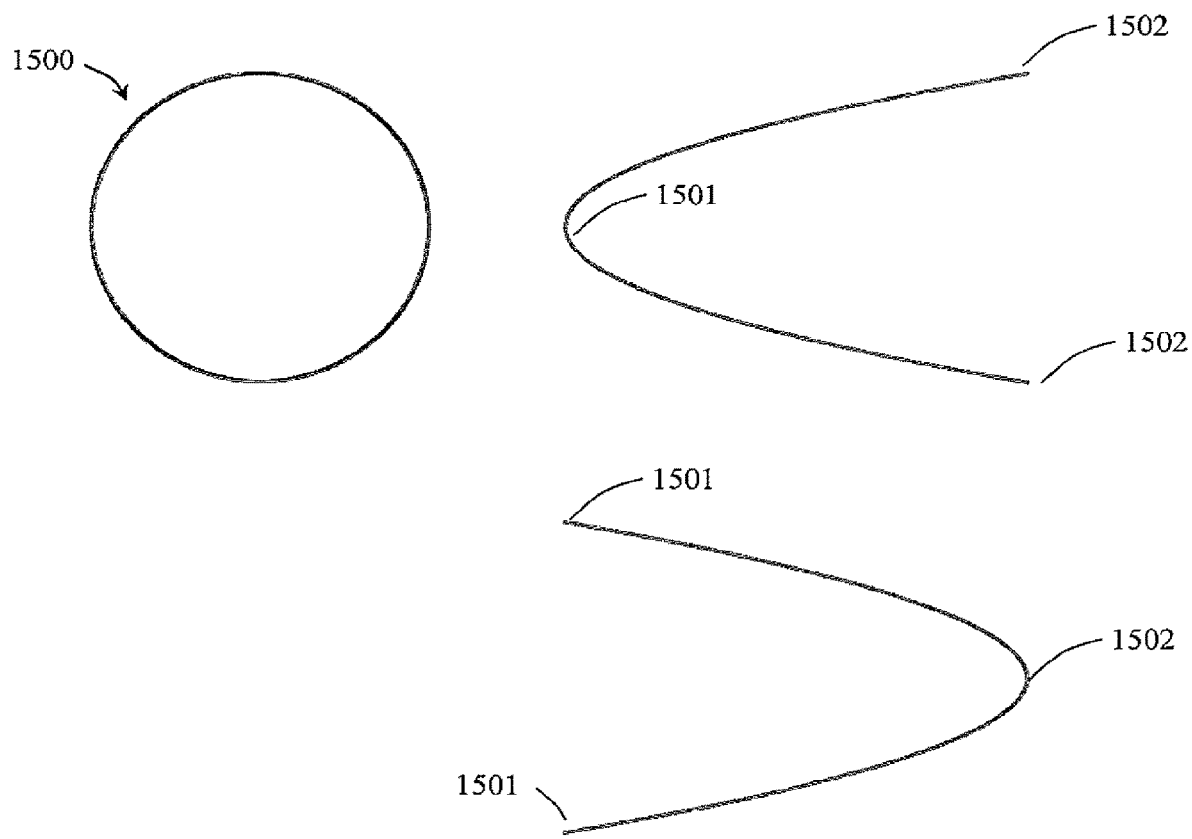
Figure 92:
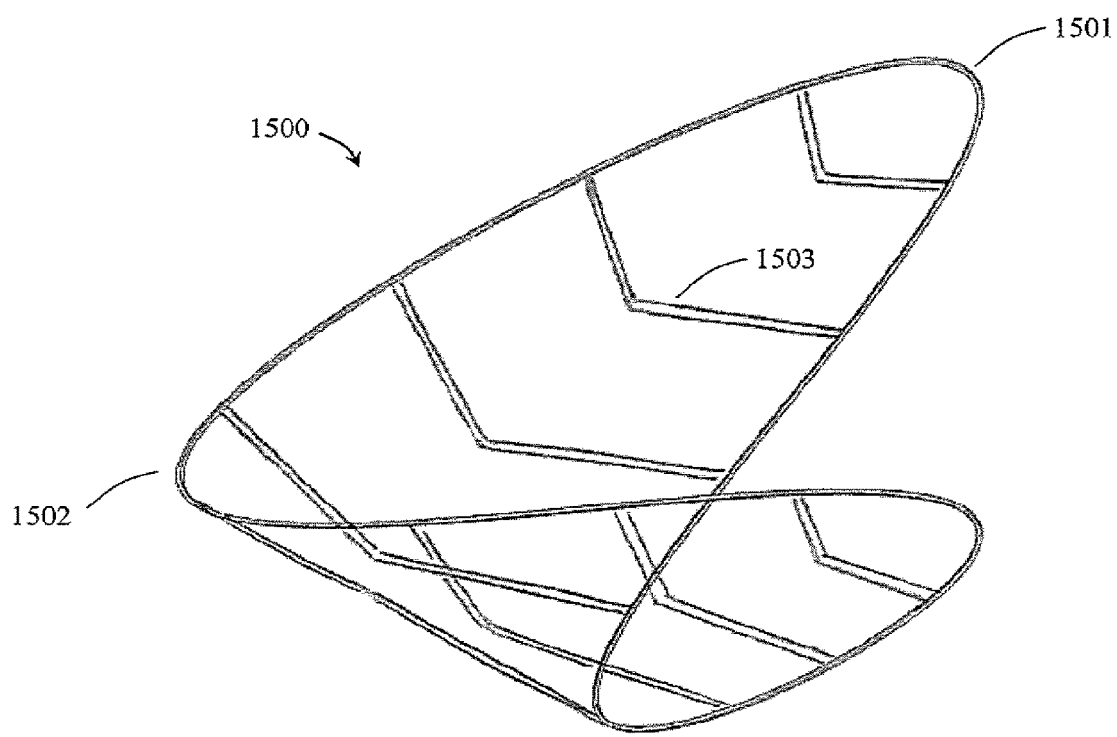
Figure 93:
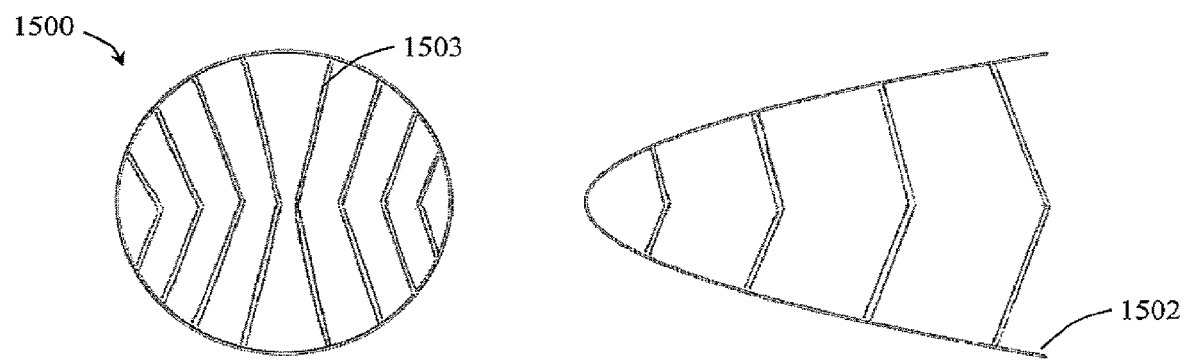
Figure 93:
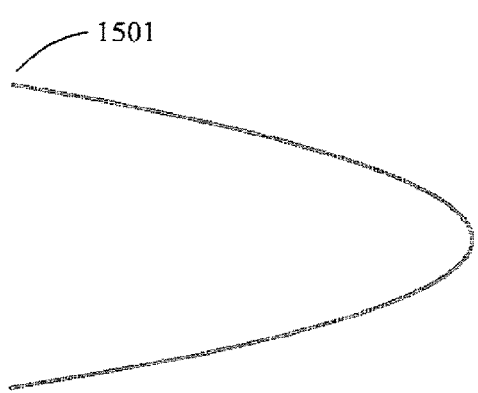

FIGS. 82 to 87 show a spring coil embodiment 1350 where a wire 1351 is wound in a spiral or spring like fashion forming a cylindrical profile in the unconstrained configuration and a spiral shaped filter when viewed axially in the filtering configuration. The wire device 1350 comprises a backbone 1352, a proximal coil 1353, u-shaped peak 1355, and a distal coil 1354. The angle between the distal end of the proximal coil 1353 and the proximal end of the distal coil 1354 is preferably in the range of 0-120.degree. at the peak 1355, even more preferably 15-45.degree. where the unconstrained filter forms an m-shape in the unconstrained elevation view and a w-shape in the unconstrained plan view. The proximal end of the distal coil 1354 is positioned preferably at a 180.degree. cylindrical revolution to the position of the proximal end of the proximal coil 1353. It is appreciated that the angles stated may be changed. To achieve the filtering configuration, the peak 1355 is rolled or wound radially inwardly relative to the backbone 1352 in a spiral fashion as shown in FIGS. 84 and 85. A biodegradable filament 1356 extends centrally through holes or eyelets in the wire 1351 from the proximal end of the backbone through each proximal coil revolution to the peak 1355 and through each distal coil revolution to the distal end of the backbone in a straight path forming a V-shape in the elevation view. The filament 1356 is knotted just proximal of each eyelet on the proximal coil and just distal of each eyelet on the distal coil to prevent the spiral filter from unwinding. The device is wound further radially inwardly to form a lower profile for delivery as shown in FIGS. 86 and 87. FIG. 88 shows how the filament slackens at the proximal and distal ends of the proximal and distal coils 1353 and 1354 respectively when deployed in a vessel smaller than the unconstrained diameter of the device. After the filament 1356 degrades, the device unwinds to a diameter the same size or slightly bigger than that of the vessel it is deployed in, restricted from over expanding the vessel, potentially causing vessel trauma and/or transmural migration, by designing the device to have sufficient rather than excessive radial force—this can be accomplished by varying the diameter of the wire 1351. Preferably, the wire is manufactured from Nitinol™ or some other shape memory material (metallic or polymeric); however, the wire may also be formed using spring steel, stainless steel, cobalt chromium or some other non-shape memory material (metallic or polymeric). The device forms a proximal cone pointing distally and a distal cone pointing proximally with coils acting as spiral shaped filter elements in the filtering configuration and vessel supporting coils in the open configuration after degradation of the filament. FIG. 89 depicts device 1400, a variant of the device 1350, with a hook 1408 to facilitate retrieval. Device 1400 comprises wire 1401, backbone 1402, proximal coil 1403, distal coil 1404, peak 1405, filament 1406, knots or stopper features 1407, and retrieval hook 1408. In another embodiment, the coils may be formed in an elliptical shape that is deployed in the vessel at an angle, thereby being adaptable to a large range of vessel sizes.

Device 1500, shown in FIGS. 90 to 93 is defined by a parabolic spring support frame with two proximal peaks 1501 and two distal peaks 1502 in the open configuration. When viewed axially, the support frame defines a circular shape to contact the vessel wall and is variable in size, through compression, to fit variable vessel sizes. Biodegradable v-shaped filter elements extend across the distal peaks and are collapsible due to the v-shaped pattern—it is appreciated that different pattern may also be chosen, for instance—articulations may be provided at the peaks of the v-shaped filter elements to reduce stress when collapsing the device into a catheter for delivery.

Figure 94:
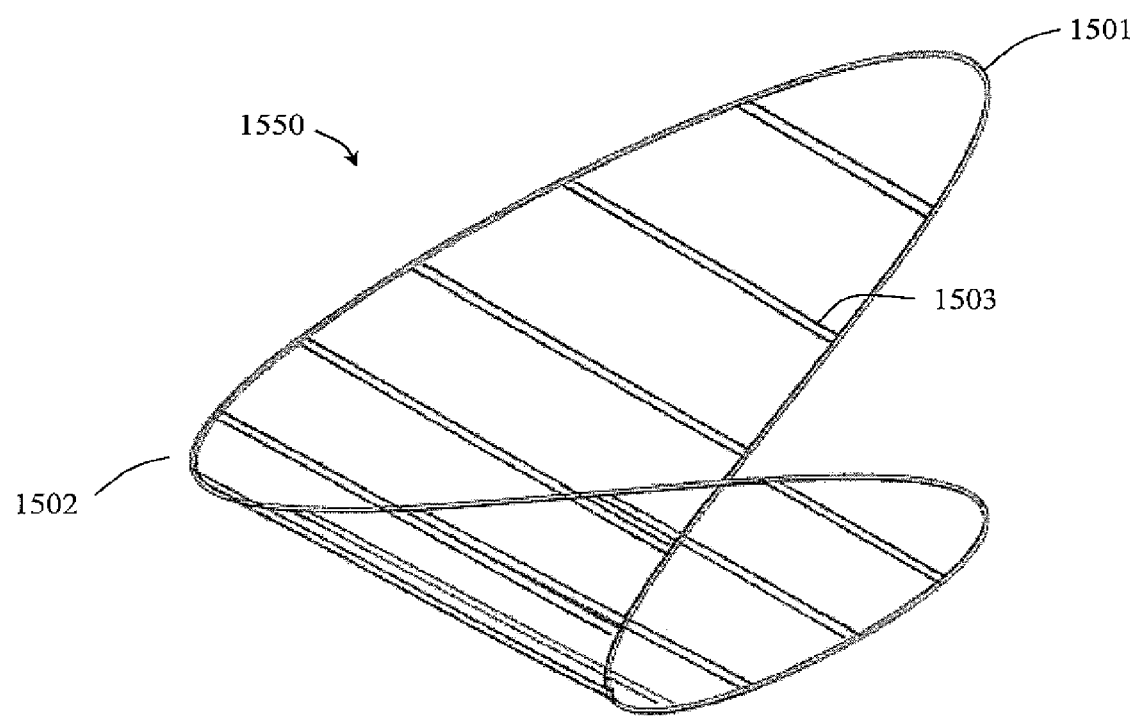
FIGS. 94 and 95 show a variation of the device above incorporating flexible filter elements, the support frame of both devices offering minimal obstruction to blood flow due to having very little interference with the vessel wall that reduces the likelihood of vessel trauma and facilitates placement of a second filter at a later stage without the need to overlap support frames, in which a filter holds a clot centrally for optimal lysis or if deployed in reverse orientation, will direct blood clots to the vessel wall to maintain central blood flow in order to keep the flow from becoming turbulent after capturing clot which may cause thrombosis.
Figure 95:
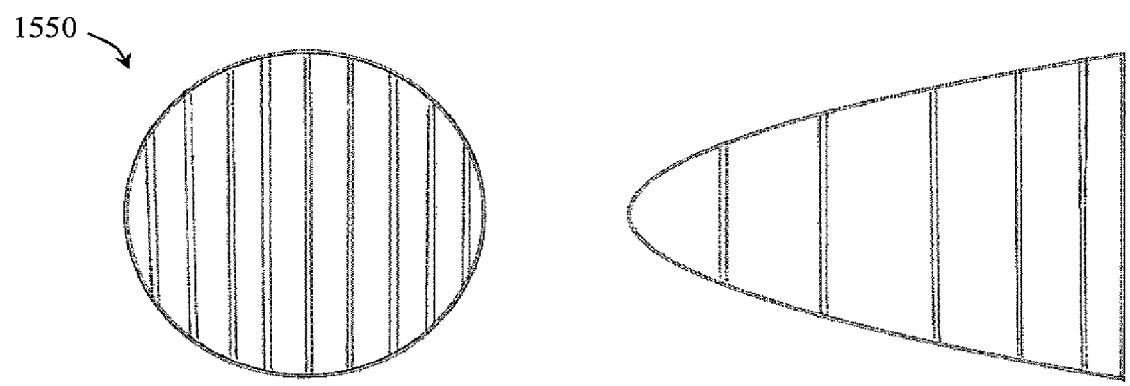
Figure 96:
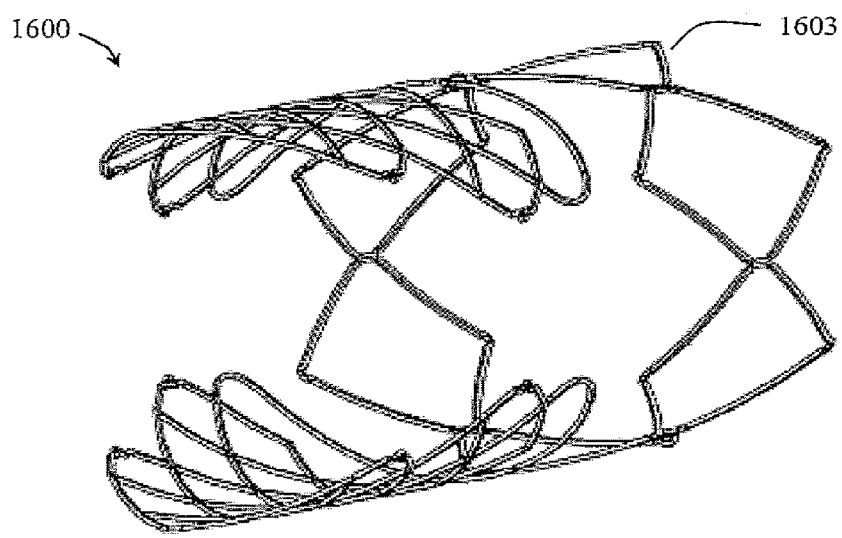
FIGS. 96 to 98b show a device with filter extensions extending proximally from two opposing proximal peaks of a distal support hoop with filter springs that extend between the filter extensions and filter elements which are collapsible.
Figure 97:
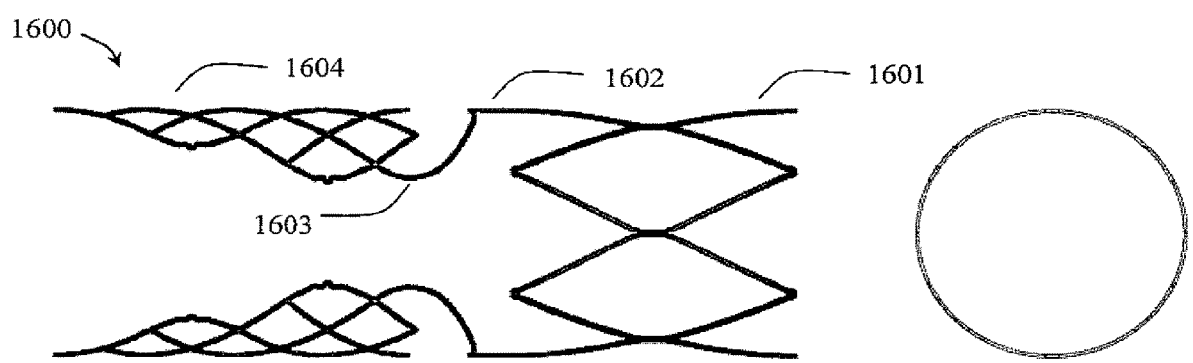
Figure 97:
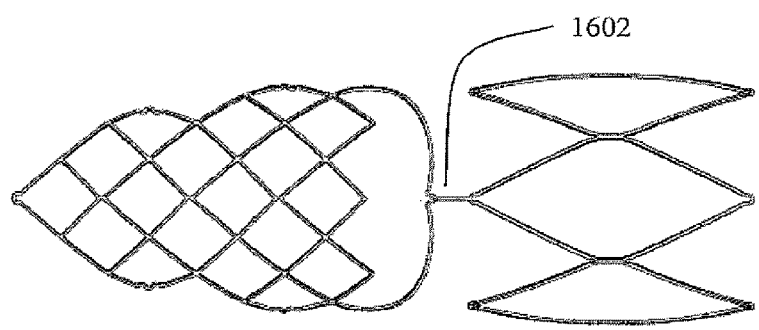
Figure 98A:
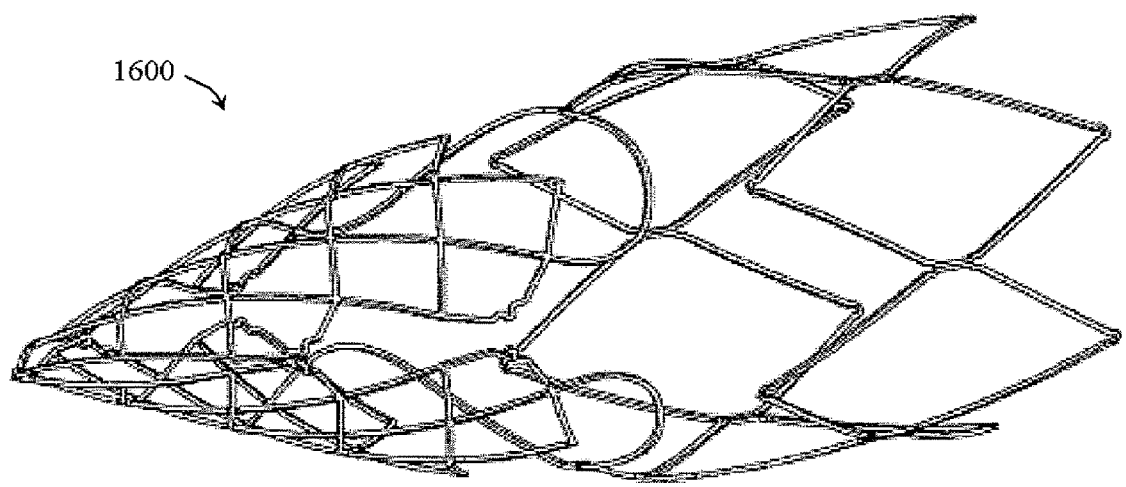
Figure 98B:
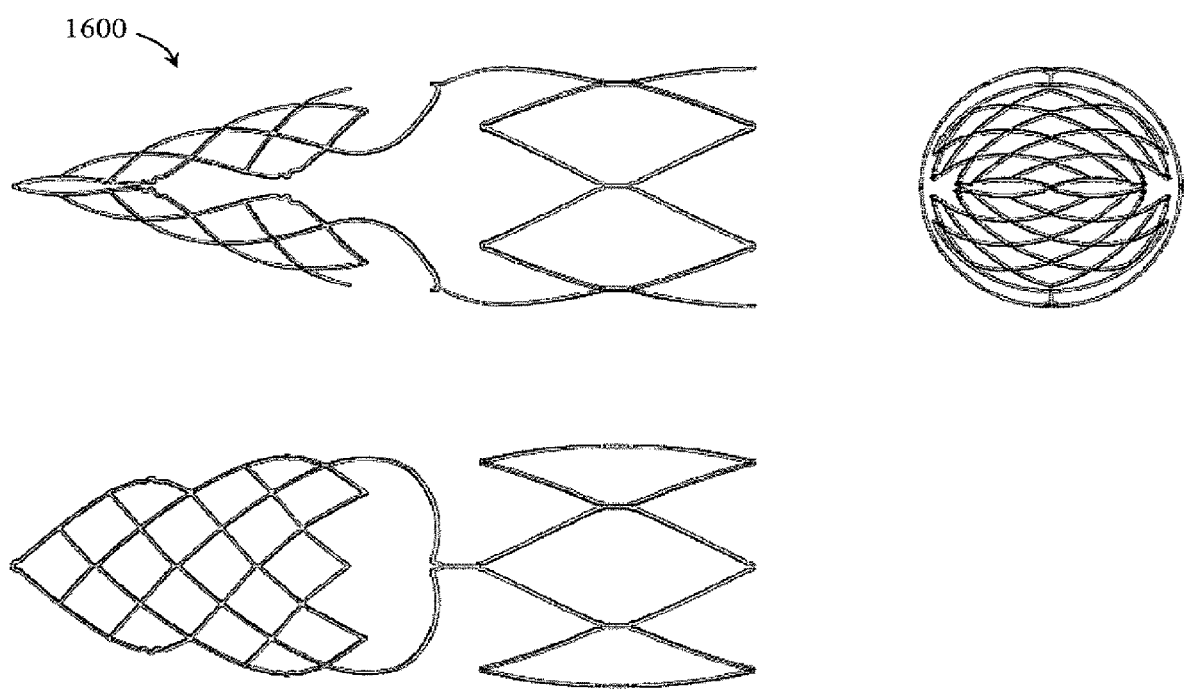
Figure 99A:
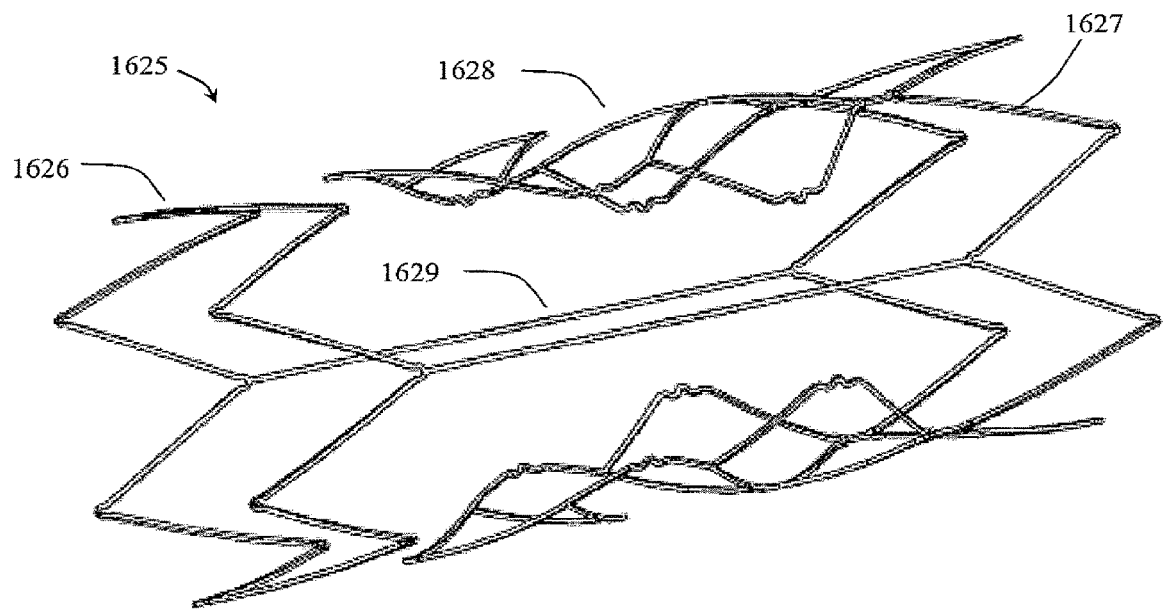
FIGS. 99a to 99d show a variant in which the above embodiment is supplied with proximal and distal support hoops.
Figure 99B:
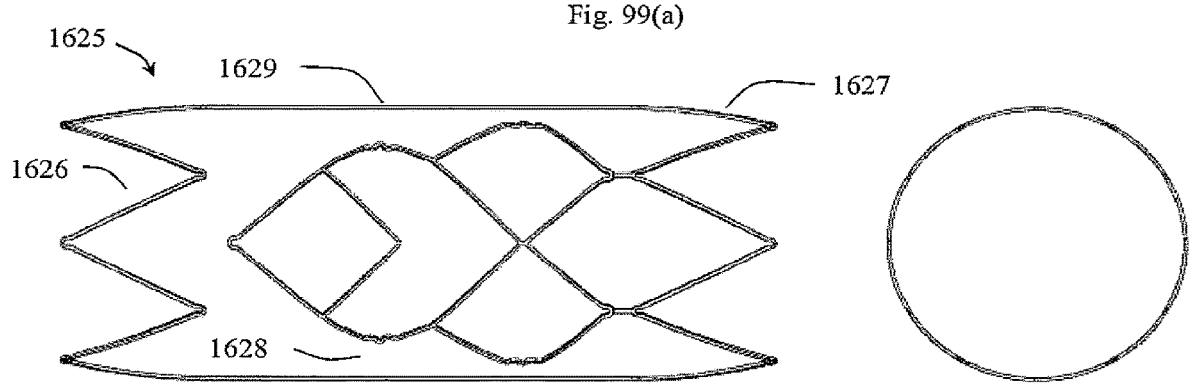
Figure 99B:
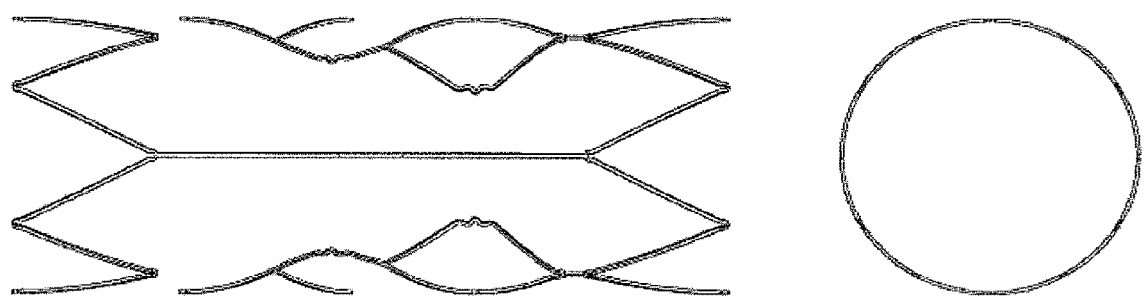
Figure 99C:
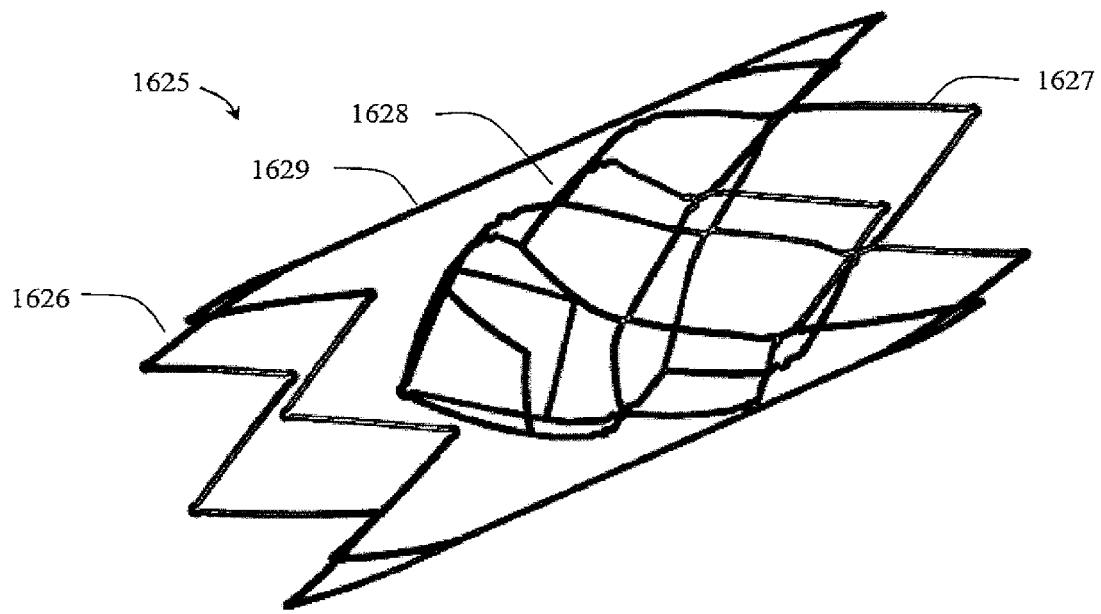
Figure 99D:
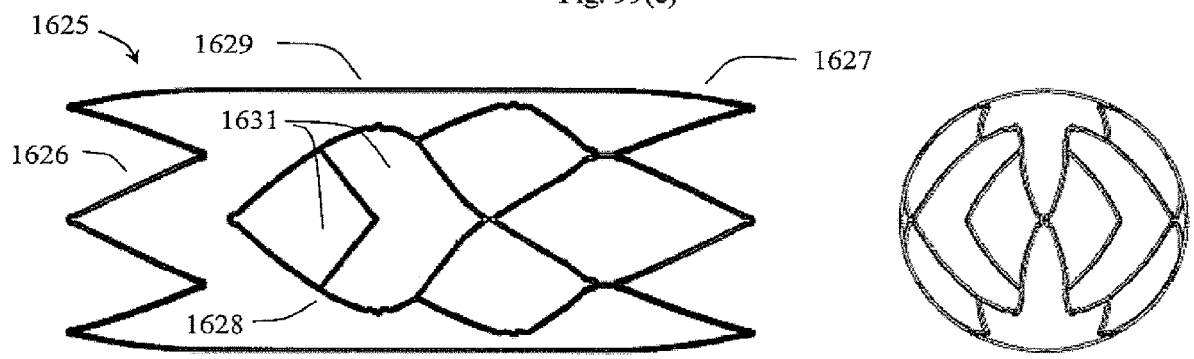
Figure 99D:
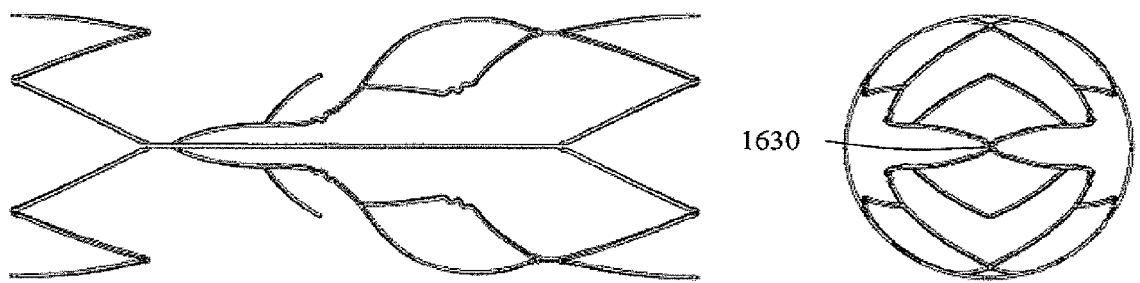
Figure 100:
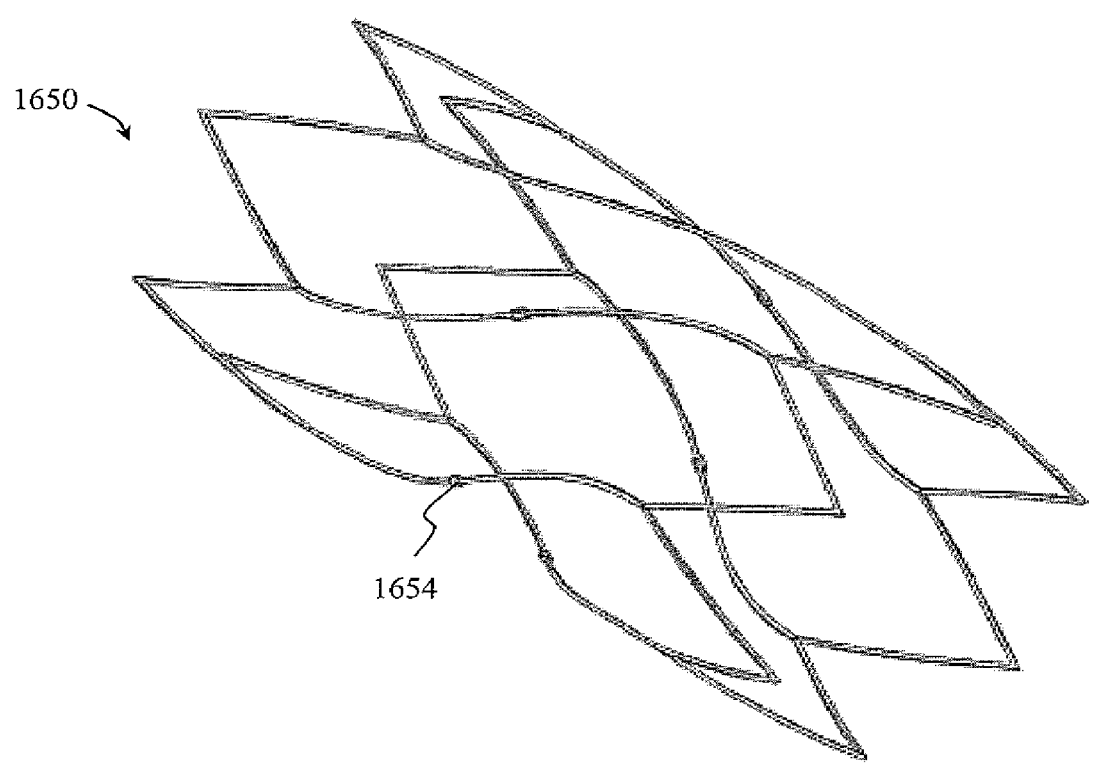
FIGS. 100 to 103 show device having helical filter elements extending between proximal and distal supports in the open configuration with eyelets positioned approximately half way along the filter elements, and in which the distal support hoop is twisted so that the eyelets of the helical filter elements move closer together and form a central apex where they are held in place.
Figure 101:
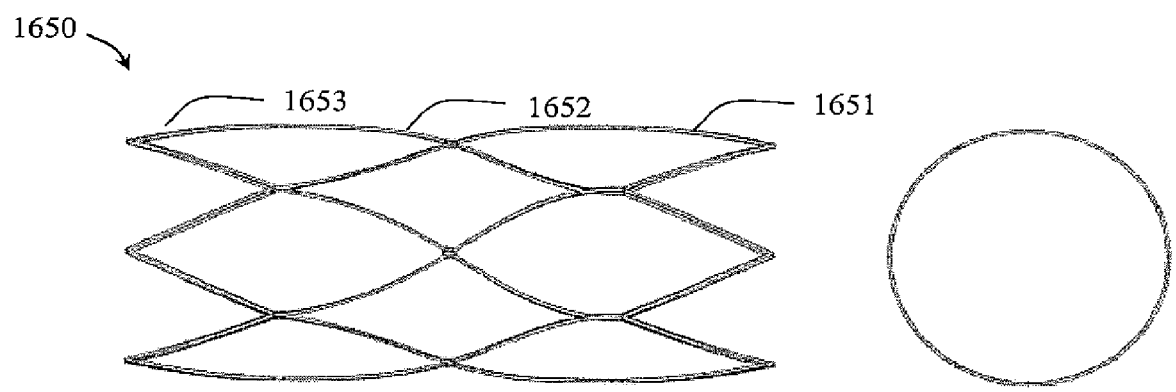
Figure 101:
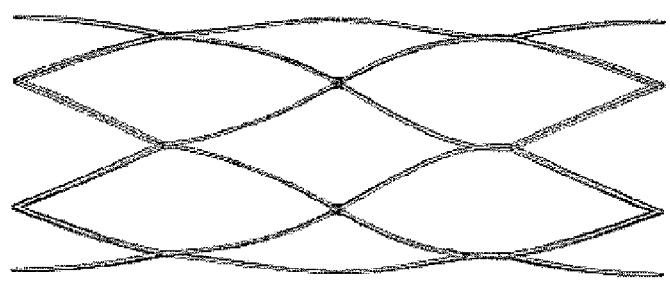
Figure 102:
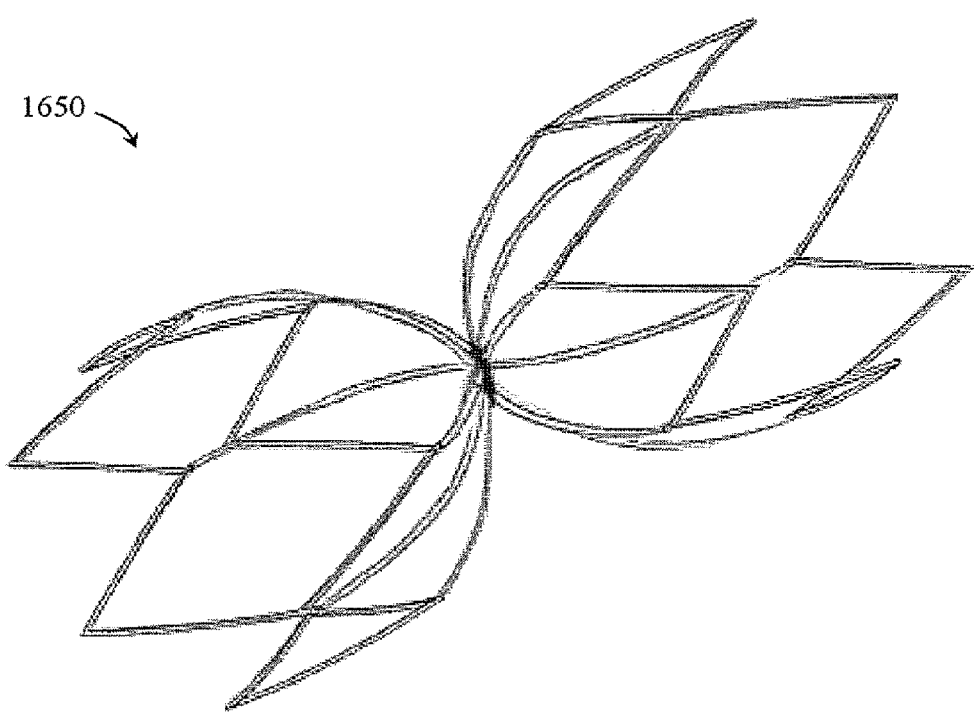
Figure 103:
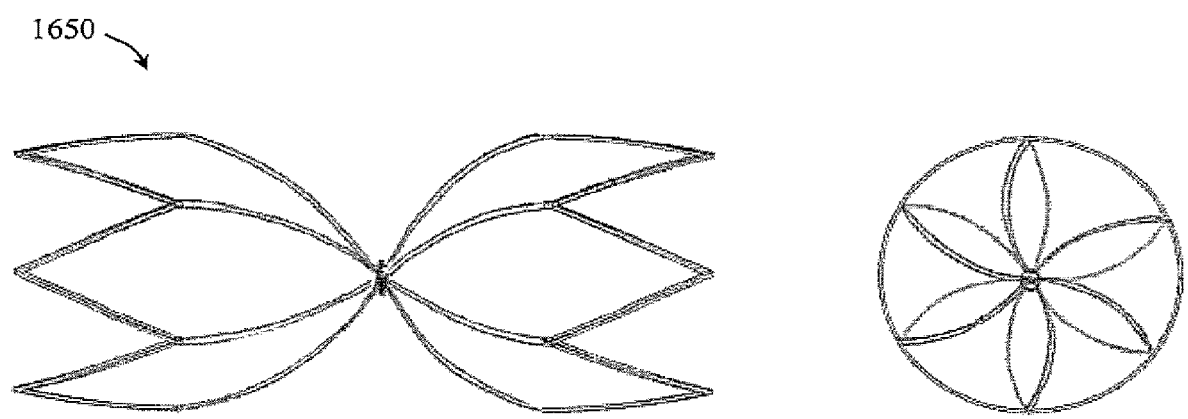
Figure 103:
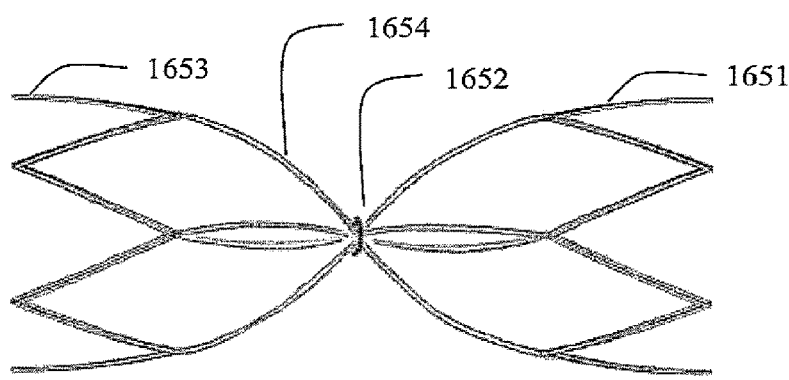

Referring to FIGS. 94 and 95 a device 1550 offers minimal obstruction to the blood flow due to its simple construction and has minimal interference with the vessel wall to reduce the likelihood of vessel trauma and to facilitate placement of a second filter at a later stage is desired without the need to overlap support frames. The filter holds clot centrally for optimal lysis or if deployed in reverse orientation, will direct blood clots to the vessel wall to maintain central blood flow in order to keep the flow from becoming turbulent after capturing clot which may cause thrombosis. Alternatively, biostable filter elements may extend from the parabolic spring support frame centrally to form a central apex held from opening by a biodegradable holder member. Device 1550 is similar to device 1550, except that flexible biodegradable filaments extend parallel to a line running across the distal peaks of the support frame 1551.

In a further embodiment, similar to devices 1, 100, 200, and 300, two parabolic springs are provided with connector elements extending between the distal peaks of the proximal spring and the proximal peaks of the distal spring. Filter elements may extend distally or proximally from the connector struts or support spring peaks to form a central apex where they are held together by a biodegradable holder member, preferably, two filter elements. Alternatively, two filter elements may extend from a single connector strut across the central axis where they are held adjacent the opposing connector strut by a biodegradable holder member. In a further embodiment, filter elements extend from free peaks of the proximal and/or distal support springs. It is appreciated that one filter element may be provided that extends across the central axis of the device.

Device 1600 is depicted in FIGS. 96 to 98*b*. A distal support 1603 comprises a proximal and distal support hoop with connector struts extending between them, filter extensions 1602 extend proximally from two opposing distal peaks of the proximal support hoop to filter springs 1603 that extend between the filter extensions and filter elements 1604. Filter elements 1604, configured to provide filtration while also being collapsible, extend to a central apex where they are held together by a biodegradable tie. After elapse of a predetermined period of time, the tie degrades and the filter elements retract to the vessel wall for unobstructed blood flow. Clot captured if present is pressed against the vessel wall by the filter element and will not escape due to the large area of the twin filter elements. The filter springs 1603 provide additional radial force to overcome endothelial growth and to break the filter elements apart if thrombus of fibrin formation is present and binds the filter elements together. Alternatively, the filter can be used in reverse orientation where clots would be directed centrally in the blood flow for optimal lysis. FIGS. 99*a* to 99*d* illustrate a further embodiment where connector struts 1629 extend between a proximal support hoop 1626 and a distal support hoop 1627 with filter elements 1628 extending proximally towards a central apex 1630 where they are held in position by a biodegradable holder member. Only two filter elements are provided such that clot caught between the filter elements and the vessel wall will be trapped after elapse of a predetermined period of time and be prevented from becoming an embolus. The filter elements are connected to one or more peaks of the distal support hoop, preferably two peaks in order to provide additional radial force to press the clots against the vessel wall and to overcome any restriction from endothelial growth and/or thrombus or fibrin formation at the apex. The filter elements are constructed with cells 1631 to provide sufficient filtration efficiency. The proximal and distal supports aid centring in the vessel.

A further embodiment 1650 is presented where helical filter elements 1652 extend between proximal and distal supports 1653 and 1651 respectively in the open configuration with eyelets 1654 positioned approximately half way along the filter elements. The distal support hoop is twisted about the longitudinal axis of the device relative to the proximal support so that the eyelets of the helical filter elements move closer together and form a central apex where they are held in place using a biodegradable holder member. After elapse of a predetermined period of time, the holder member degrades and the filter unwinds into a cylindrical profile for unobstructed blood flow. Refer to FIGS. 100 to 103.

Figure 104:
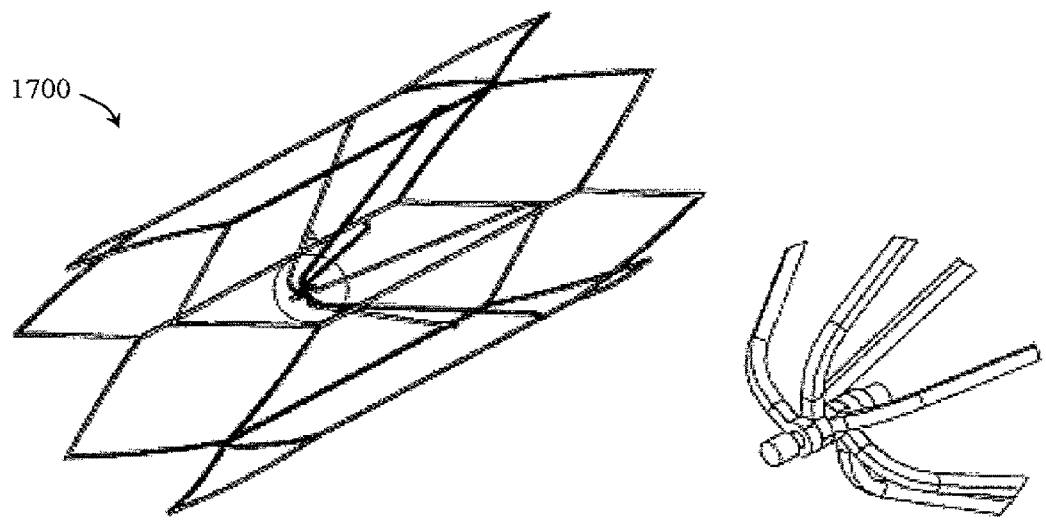
FIGS. 104 and 105 show a device in which each filter element has a slightly different length such that their ends are staggered at the central apex and form a lumen for insertion of a biodegradable pin-shaped holder.
Figure 105:
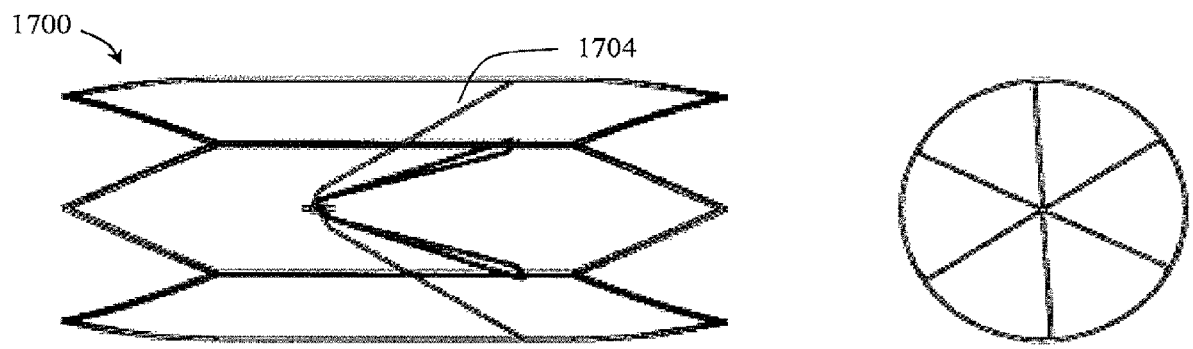
Figure 105:
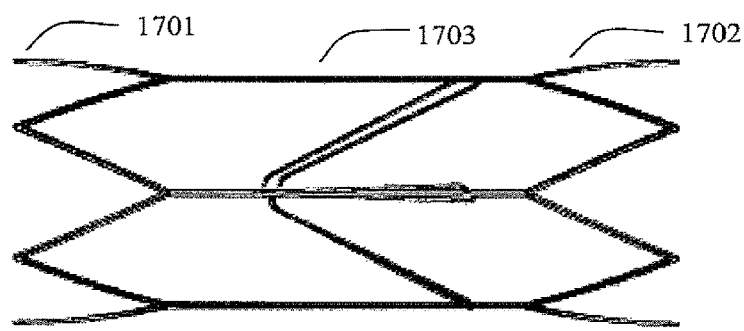

FIGS. 104 to 105 depict a device 1700 with a proximal support 1701, and distal support 1702, connector struts 1703 extending between the proximal and distal support, and filter elements 1704 extending from the connector struts towards a central apex, each filter element having a slightly different length such that the eyelets at the filter element ends are staggered at the central apex and form a lumen for insertion of a biodegradable pin-shaped holder member.

Figure 106:
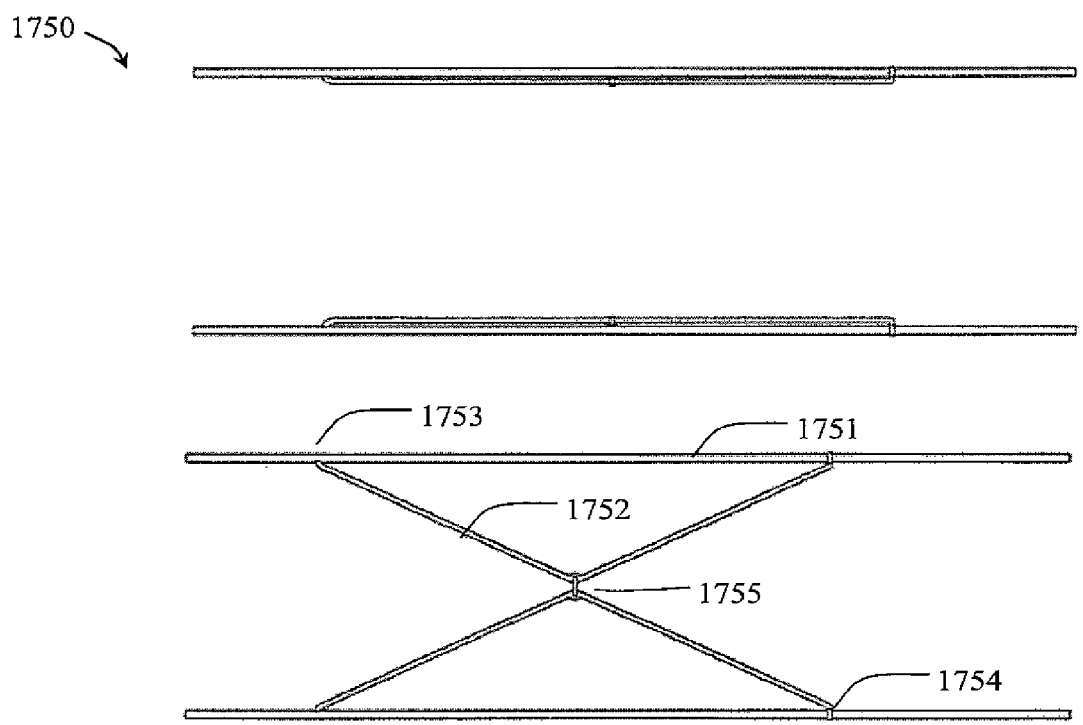
FIG. 106 illustrates a device with filter elements that have one end slidably attached to connector struts and with the other end fixed, and in which a biodegradable tie holds the filter elements centrally in the vessel to form a double cone filter.

FIG. 106 illustrates a device 1750 with an array of filter elements 1752 that have one end 1754 slidably attached to connector struts 1751 with the other end 1753 fixed. The connector struts extend between a proximal and distal support hoop (not shown) as described throughout this application. A biodegradable tie 1755 holds the filter elements centrally in the vessel to form a double cone filter. After elapse of a predetermined period of time, the holder member degrades and the filter elements retract to the vessel wall, any clot if present between the double cones will be pressed against the vessel wall rather than becoming an embolus.

Figure 107:
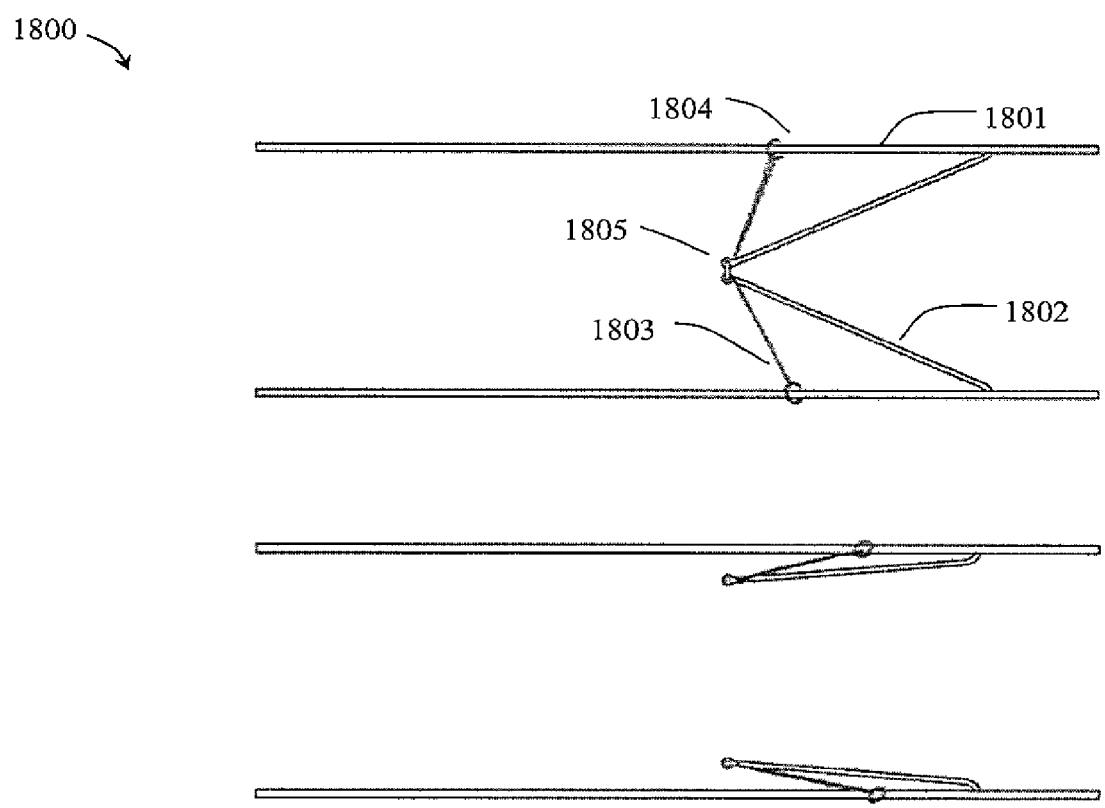
FIG. 107 shows a device in which secondary filter elements are attached to the proximal ends of filter elements, forming a proximal apex and the distal ends of secondary filter elements are slidably attached to connector elements that extend between proximal and distal supports.

FIG. 107 depicts a further embodiment where secondary filter elements 1803 are attached to the proximal ends of filter elements 1802 forming a proximal apex 1805 in the filtering configuration and wherein the distal ends of secondary filter elements 1802 are slidably attached to connector elements 1801 that extend between proximal and distal supports (not shown). The secondary filter elements form a connection between a plurality of filter element in order to hold clot if present upon conversion between the plurality of first filter elements 1802 that might otherwise pass through due to the plurality of gaps formed where the plurality of connector struts lie between the plurality of first filter elements. Therefore, upon conversion—clots (if present) pressed against the first filter elements by the blood flow will be pushed radially outwardly against the vessel wall while clots pressed against the secondary filter elements upon conversion will be pushed radially outwardly against the connector struts 1801 thereby preventing the captured clots from becoming an embolus upon conversion.

Figure 108:
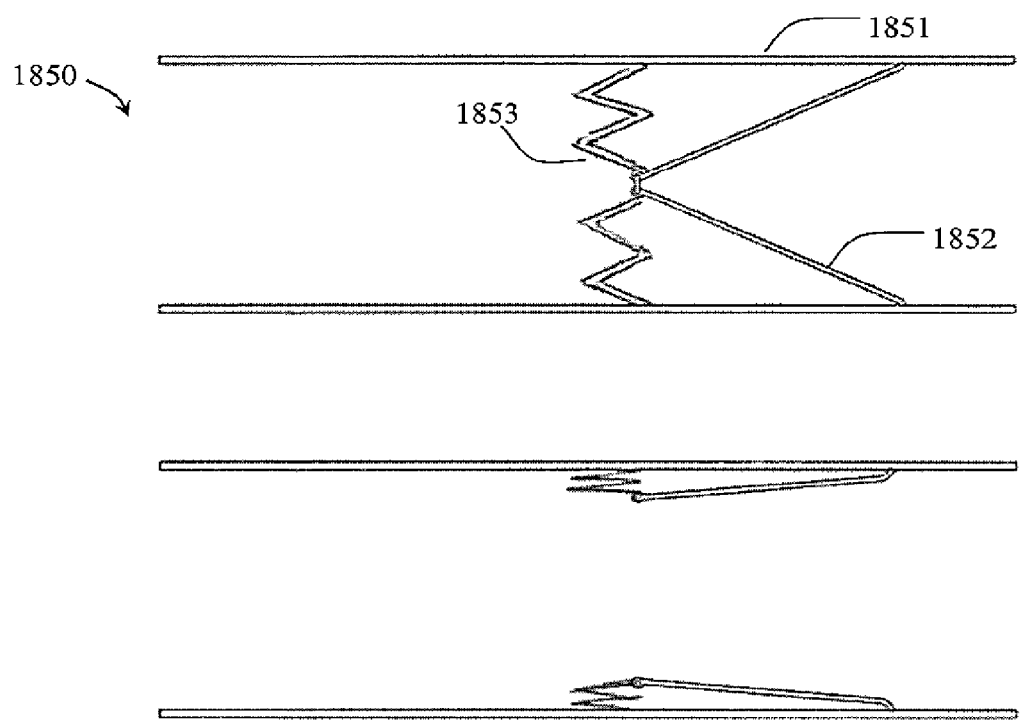
FIG. 108 shows a device in which spring-like filter elements extend between the connector struts and the apex such that upon conversion, the springs apply a force to the apex aiding in successful retraction to the vessel wall.

FIG. 108 depicts an embodiment 1850 comprising connector struts 1851 extending between proximal and distal supports (not shown) and filter elements 1852 extending towards a central apex in the filtering configuration. Spring like filter elements 1853 extend between the connector struts and the apex such that upon conversion, the springs apply a force to the apex aiding in successful retraction to the vessel wall. Alternatively, a radial hoop may be compressed by a holder member (for example—a biodegradable tube) and expand upon conversion for unobstructed blood flow.

Figure 109:
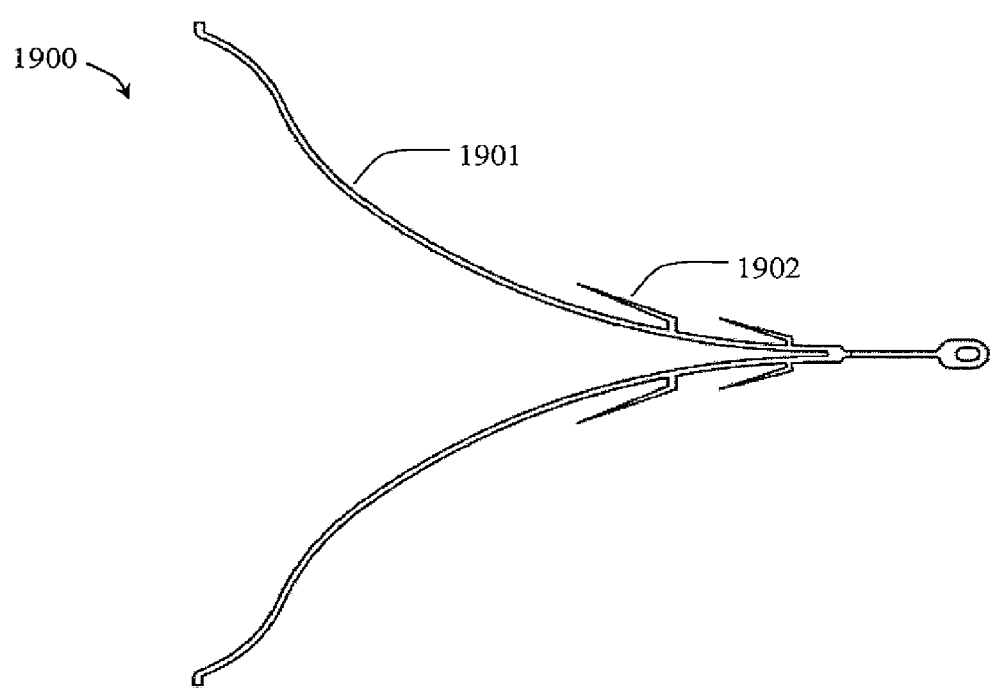
FIG. 109 illustrates V-shaped filter elements with barbs that can be bent out of plane such that they extend radially inwardly during filtering and post conversion, the barb features retaining a clot during conversion.

FIG. 109 illustrates v-shaped filter elements with barbs that can be bent out of plane such that they extend radially inwardly during filtering and post conversion. The barb features hold onto clot during conversion if present thereby prevent it from becoming an embolus.

Figure 110:
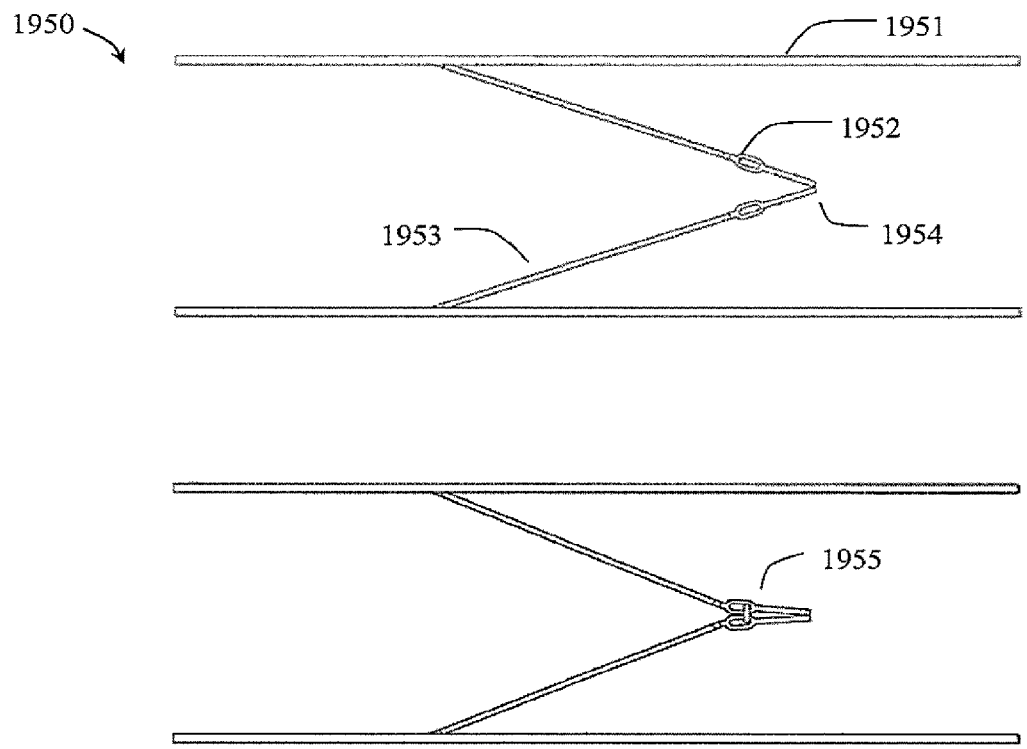
FIG. 110 depicts a device in which filter elements extend distally towards a central apex from connector struts and with eyelets positioned proximally of the proximal ends of the filter elements at the central apex.
Figure 111:
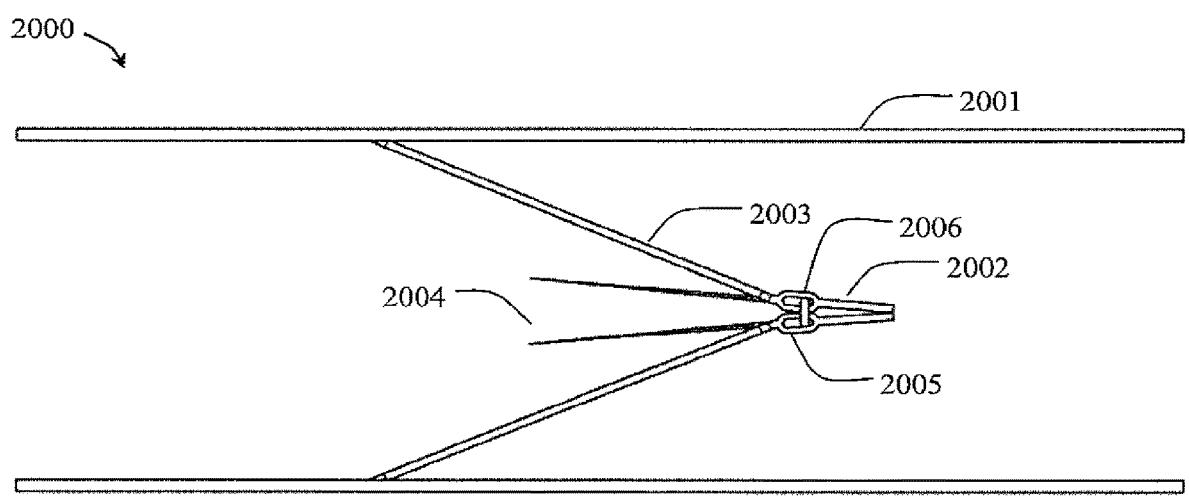
FIGS. 111 to 113 show a variant of the above device with spikes extending proximally to trap and/or break down clots after conversion.
Figure 112:
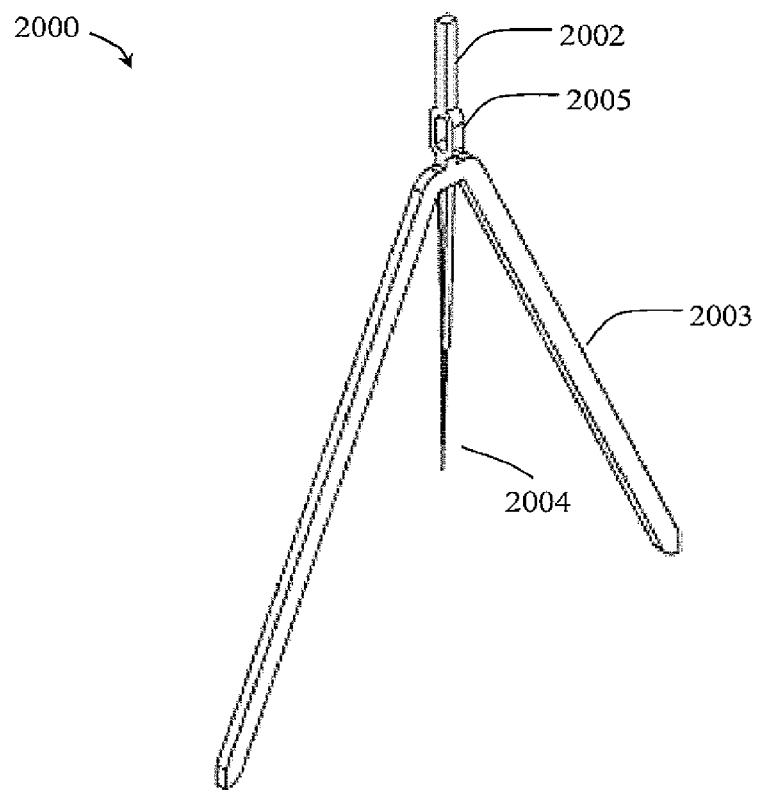
Figure 113:
Figure 113:
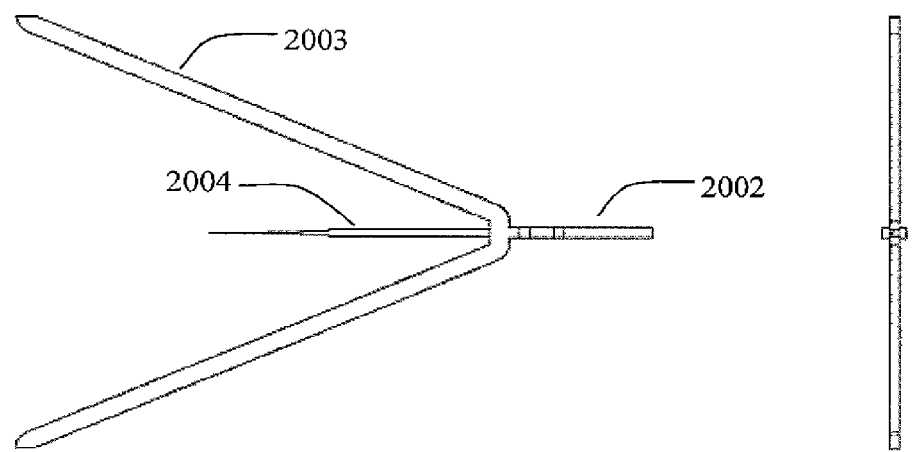

FIG. 110 depicts filter elements 1953 extending distally towards a central apex 1954 from a plurality of connector struts 1951 that extend between proximal and distal support hoops (not shown) with eyelets 1952 positioned proximally of the distal ends of the filter elements at the central apex 1954. A biodegradable holder member 1955 is threaded through the eyelets and tightened bringing them together and creating stored energy between the plurality of filter elements as the distal ends of the filter elements are forced to bend radially outwardly relative to the filter elements. If thrombus of fibrin formation is present upon conversion, the stored energy will release and aid in breaking the filter elements apart for successful retraction to the vessel wall while also aiding in overcoming endothelial growth at the vessel wall. A further embodiment 2000 is similar to that of 1950 except that spikes 2004 are provided that extend proximally from the eyelets 2003. If clot is captured during use it will be impaled on the spikes or caught between the spikes and the filter elements so that upon conversion the filter elements will bring the clot radially outwardly to the vessel wall. Refer to FIGS. 111 to 113. The spikes 2004 may bend out of plane, preferably radially inwardly in order to prevent then from causing vessel trauma post conversion of the biodegradable member 2006.

Figure 114:
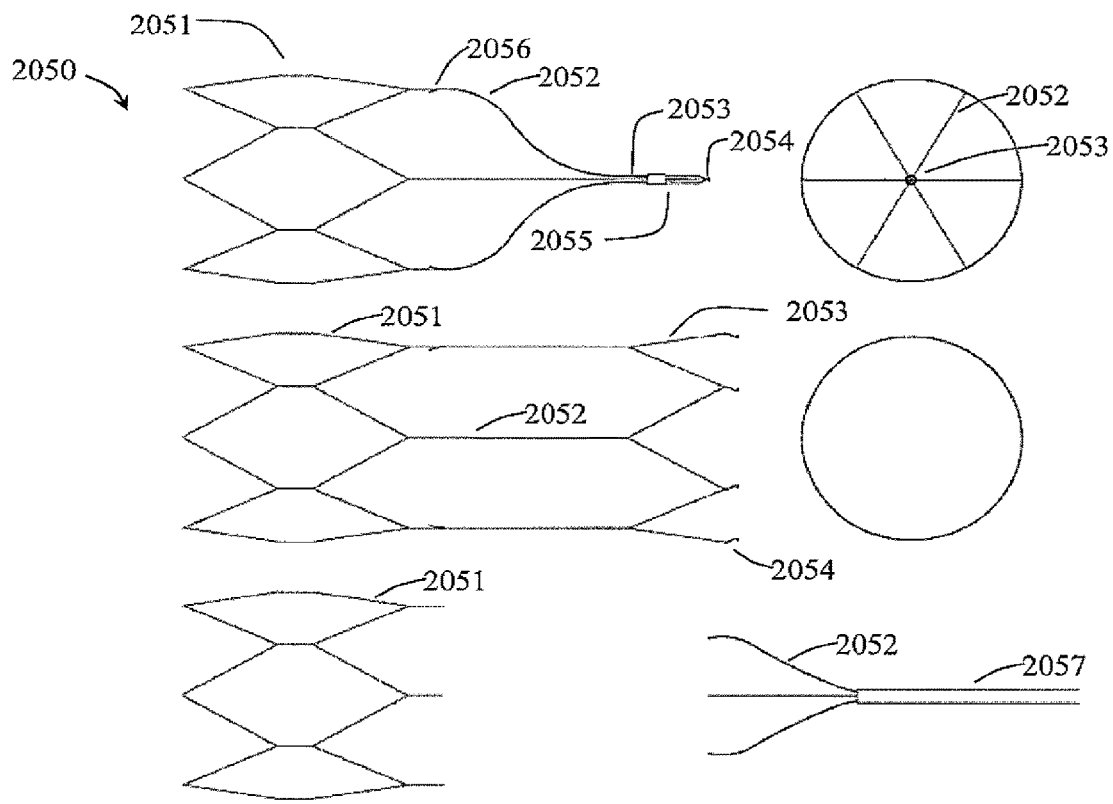
FIG. 114 shows a device that can be left in place to convert to an open configuration or removed prior to conversion with the aid of a snare and retrieval catheter.
Figure 115:
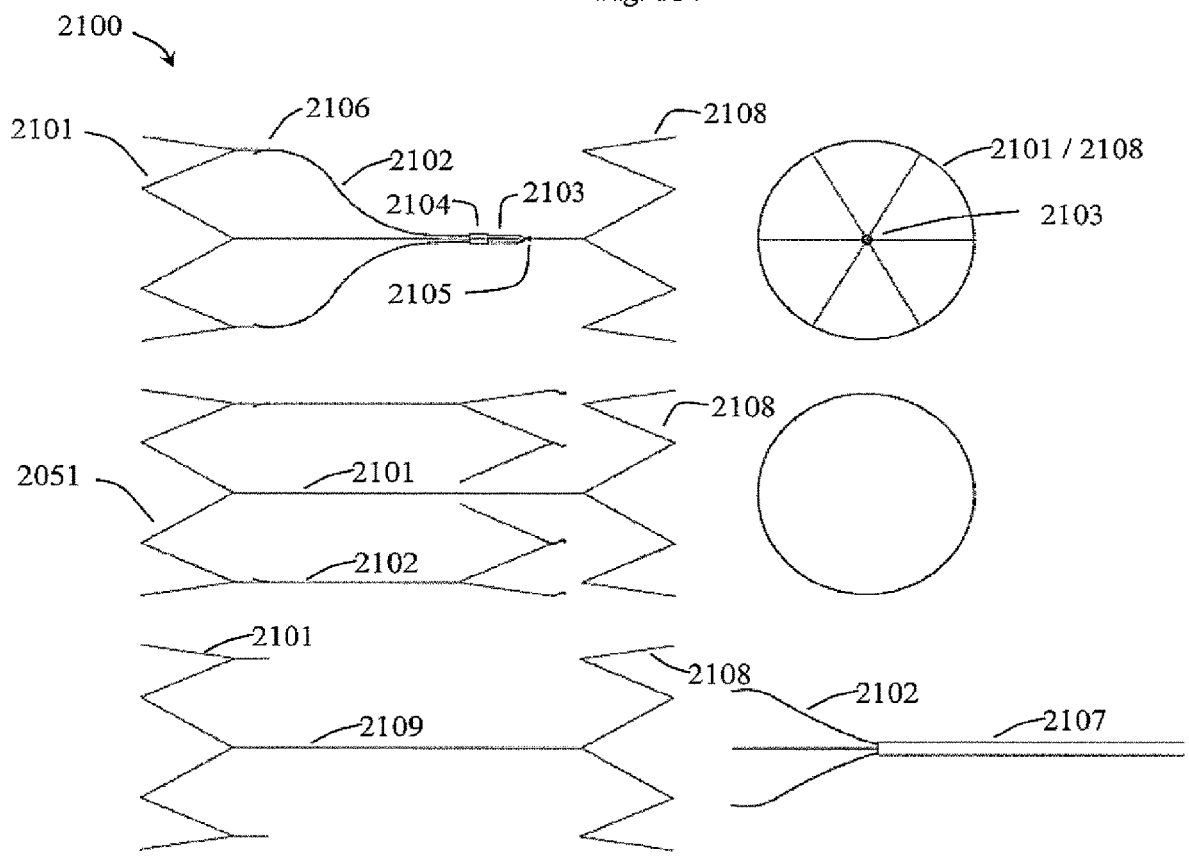
FIG. 115 shows a variant of the above device incorporating both proximal and distal supports in the filtering configuration.

Referring to FIG. 114, device 2050 comprises a proximal support 2051, filter elements 2052, a distal filter apex/support 2053, retrieval hooks 2054, a biodegradable holder member 2055 and a retrieval catheter 2057. The top image depicts the device in a filtering configuration while the middle image shows the device after degradation of the holder member 2055 where the distal filter apex, constructed of a compressed hoop, expands radially outwardly to form a distal support hoop in the open configuration. The compressed filter apex hoop has sufficient radial force to overcome any endothelial growth at the vessel wall and/or fibrin and thrombus formation at the apex if present in order to provide unobstructed bloodflow. The bottom image depicts the device during removal of the filter portion prior to degradation of the holder member 2055. Therefore, the filter portion may be removed or left in place to open passively. The proximal ends 2056 of filter elements 2052 are curved radially inwardly to prevent trauma to the vessel wall during use and during filter removal. The attachment between the filter elements and the proximal support 2051 may be biodegradable or an interference fit where a reasonably low force is required to pull the filter elements through the interference fitting. FIG. 115 depicts a further embodiment 2100 similar to 2050 where a proximal support 2101, filter elements 2102, a central filter apex/support 2103, retrieval hooks 2104, a biodegradable holder member 2105, a distal support 2108, connector struts 2109 extending between the proximal and distal supports and a retrieval catheter 2107. Here the central filter apex comprises two half hoops so that there is no overlapping in the open configuration shown in the middle image. Alternatively, the central apex/support may be provided as a complete hoop. The distal support 2108 aids centring in the vessel to prevent tilting of the device.

Figure 116:
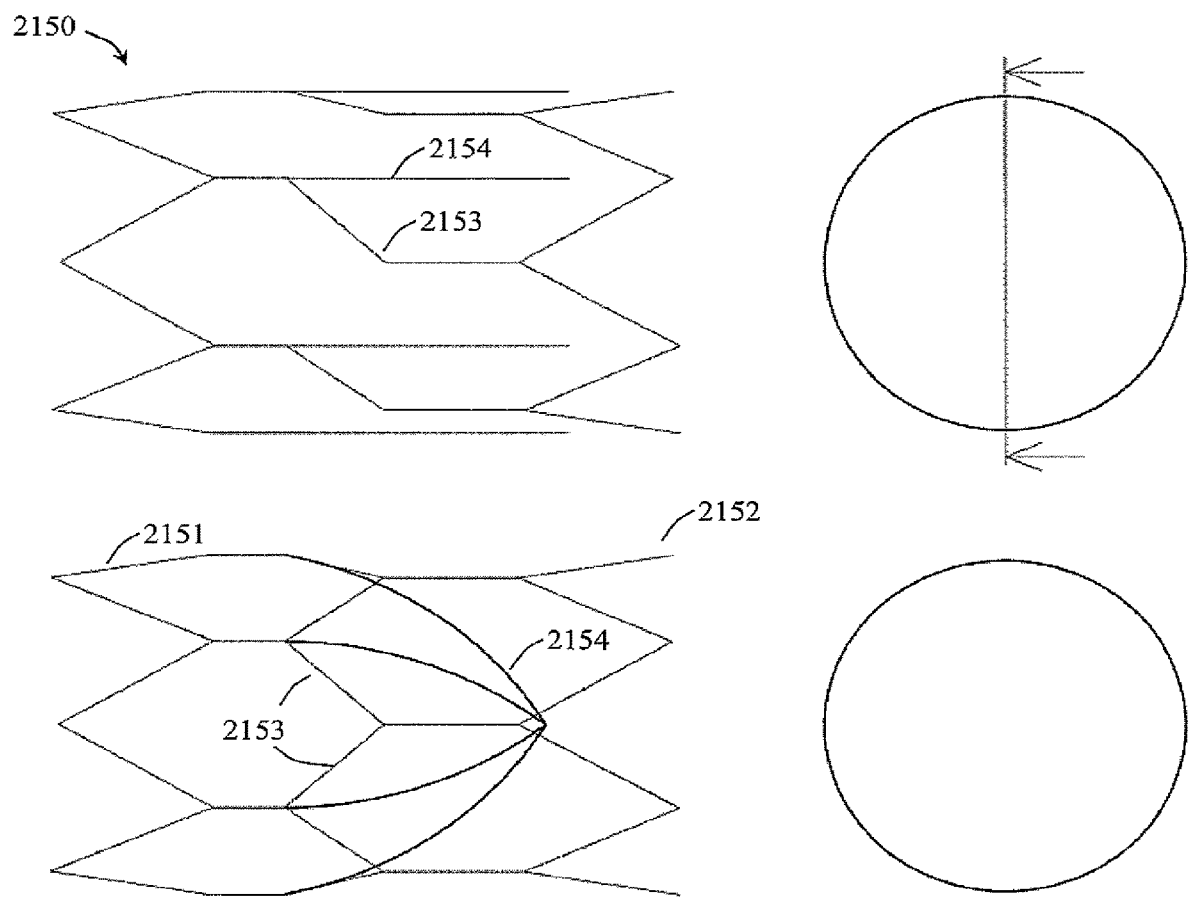
FIG. 116 depicts a device with stepped connector struts that extend between offset peaks of proximal and distal support hoops such that filter elements can extend in a straight line from a proximal segment of the connector struts.

Illustrated in FIG. 116, is embodiment 2150 where stepped connector struts 2153 extend between distal peaks of the proximal support 2151 and proximal peaks of the distal support 2152 that are offset from each other. The top image shows the open configuration (a sectioned view is proved for clarity) while the bottom image shows the device in the filtering configuration. Filter elements 2154 extend in a straight line continuing from the proximal segment of the connector struts 2153.

Figure 117:
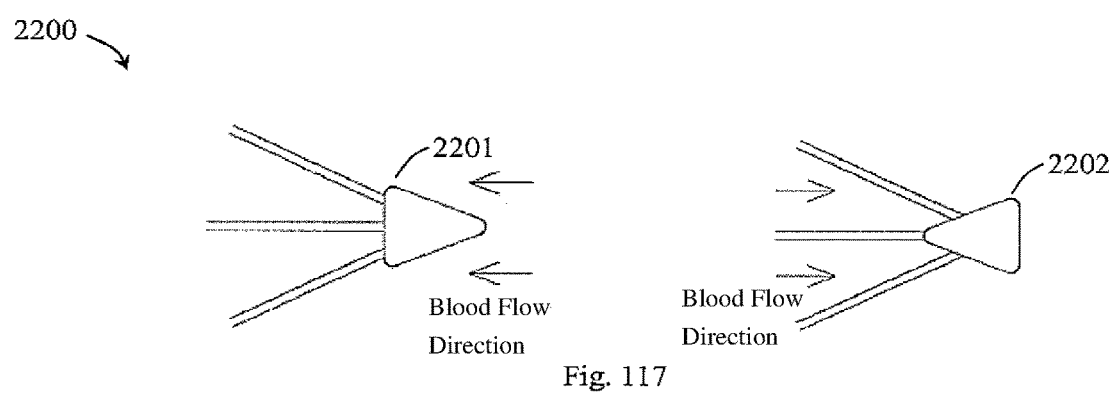
FIG. 117 shows a streamlined holder to reduce disturbance to the blood flow aiding in preventing thrombus and/or fibrin formation.

Referring to FIG. 117, an over moulded biodegradable apex 2201 and 2202 are shown in the left and right images respectively. Both apices have a conical construction that points in the direction of blood flow in order to reduce the stress of blood flow at the apex to aid in preventing fibrin and/or thrombus formation.

Figure 118:
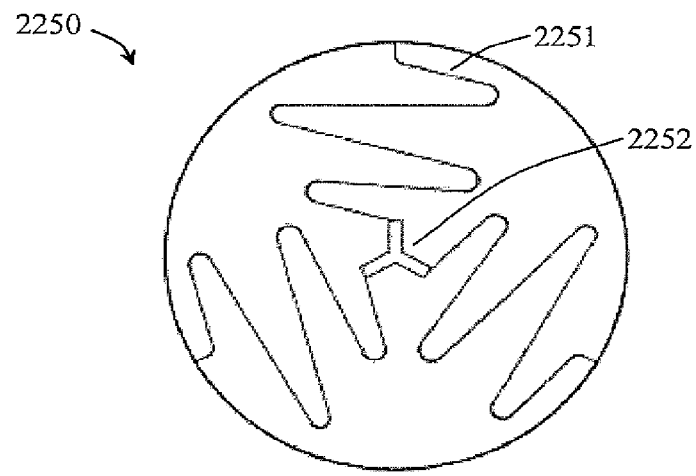
FIGS. 118 to 120 depict various embodiments with only three filter elements.
Figure 119:
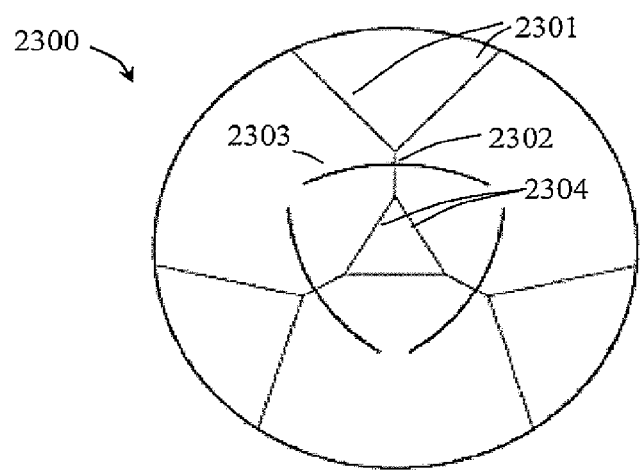
Figure 120:
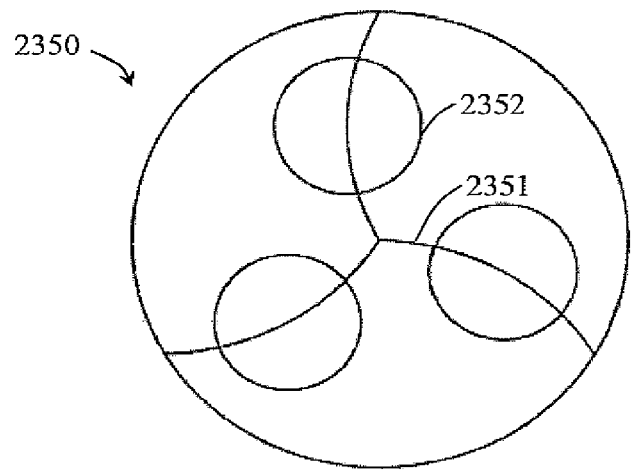

FIGS. 118 to 120 depict further embodiments with proximal and distal support hoops with connector struts extending between them and a set of three filter elements extending centrally towards an apex. Device 2250 has zigzag shaped filter elements 2251 with a tri-spoke biodegradable holder member 2252. Holder 2252 is designed to minimise obstruction to blood flow preventing thrombus and/or fibrin formation. Device 2300 is provided with filter elements comprising proximal v-shaped struts 2301 extending centrally from connector struts to converge into single struts 2302 before diverging into V-shaped struts 2304 where struts 2303 extend in a curve from struts 2302. Device 2350 has filter elements with struts 2351 extending towards a central apex and curved cellular struts 2352 extending around struts 2351. Reducing the number of filter elements provides less obstruction to blood flow at the apex to aid in reducing thrombus and/or fibrin formation.

FIG. 121 to FIG. 140 illustrate holders which can be used with filters of various embodiments. The holders have excellent conversion attributes with low resistance to opening upon conversion. Conversion attributes include a) the density of surface area obstructing blood flow at the apex and b) the separation between filter element ends at the apex.

Obstruction to blood flow can cause areas of recirculation and stagnation that promote fibrin and/or thrombin formation. If the density of surface area obstructing blood flow is high in a particular location larger areas of stagnation and recirculation will form at that location. Therefore, distributing the surface area of components at the apex over a larger cross sectional area of a blood vessel will reduce the density of surface area at the apex thereby reducing areas of stagnation and recirculation and decreasing the likelihood of fibrin and/or thrombin formation.

The distance between filter element ends can be increased in order to separate filter element ends to reduce the likelihood of fibrin and/or thrombin formation extending from one filter element end to another. The formation of fibrin and/or thrombin around filter element ends held in close proximity may lead to a band of fibrin and/or thrombin extending around the filter element ends that may cause resistance to opening. The effect of increased separation between filter element ends is enhanced when the cross sectional area of material linking filter element ends is less than that of the filter element ends. This is due to a reduced obstruction to blood flow in the vicinity of the holder material linking the filter element ends that provides reduced areas of stagnation and recirculation compared to that at the vicinity of the filter element ends.

Where a filament or thread incorporating a knot is used as a holder to link filter element ends together, the knot and threading arrangement can be optimised to provide a smaller profile thereby reducing obstruction to blood flow and minimising the likelihood for fibrin and/or thrombin to form.

Each of the embodiments in FIGS. 121 to 140 is described in detail below. The invention is not limited to the embodiments described but may be varied in construction and detail. For example, a single-stranded filament holder may be applied to devices described as having multiple stranded filament holders or a different number of filter elements.

Figure 139:
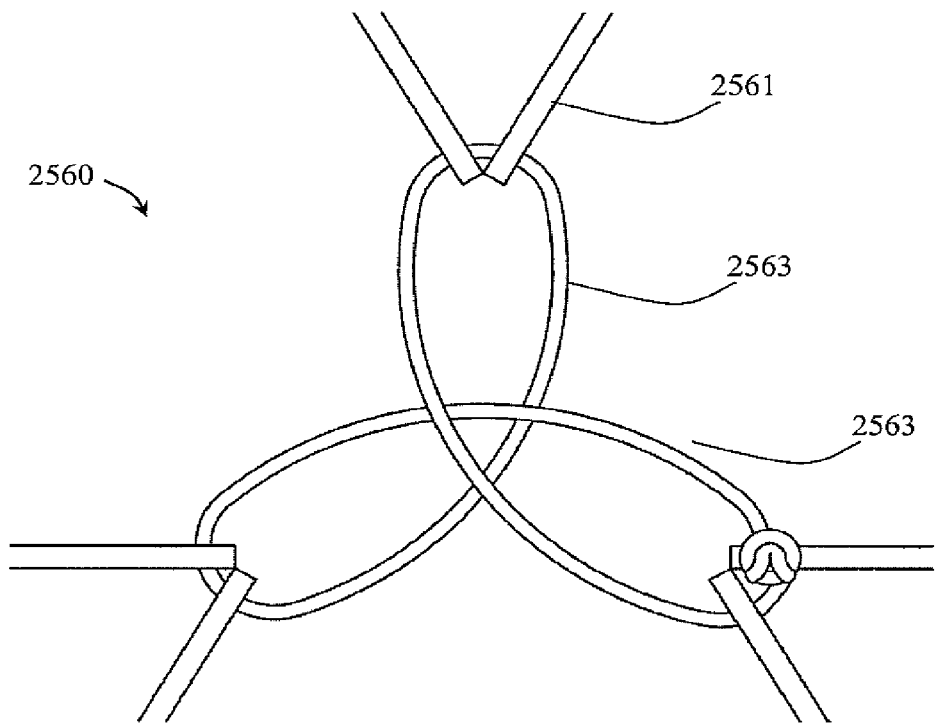
Figure 140:
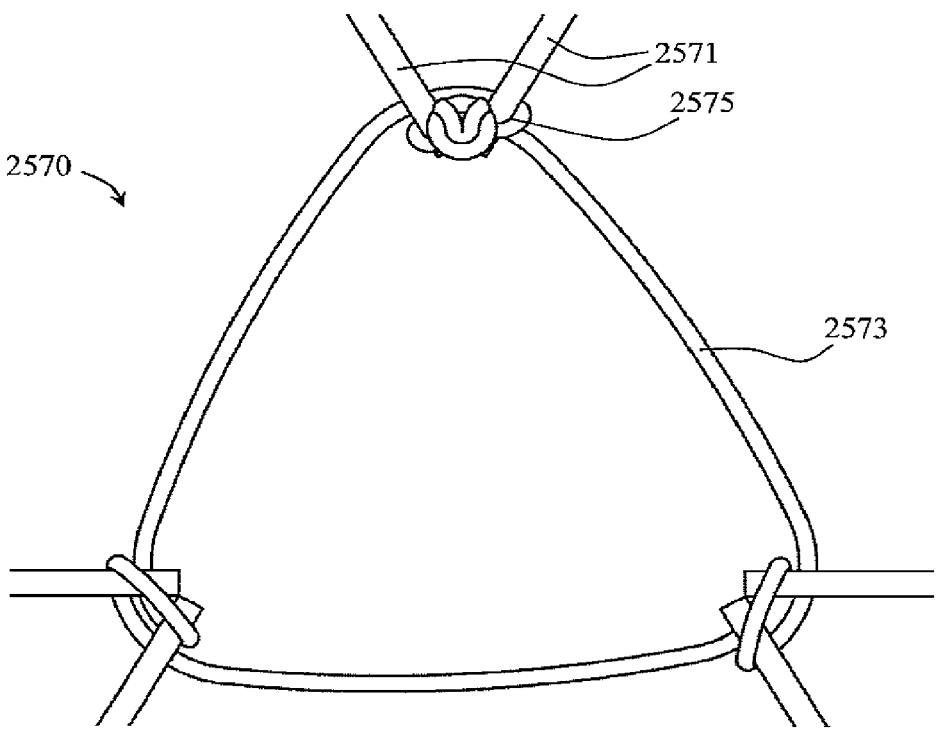

The embodiments shown in FIGS. 121 to 138 have separation between all filter element ends in the closed configuration. This is achieved by increasing the central space around which the holder extends. FIGS. 139 and 140 illustrate embodiments where one or more filter element ends are grouped together by looping the holder filament around one or more filter element openings. Given the same number of filter elements, grouping filter elements gives rise to a larger separation between groups than there would be between individual filter element ends if compared to ungrouped filter elements. Increased separation reduces the likelihood of fibrin and/or thrombin formation spanning between filter element ends which may cause resistance to opening by binding the filter elements together. Also, there would be more opening force by say two filter element ends together than by an individual element. This would mitigate the effect of any fibrin/thrombin growth.

Figure 121:
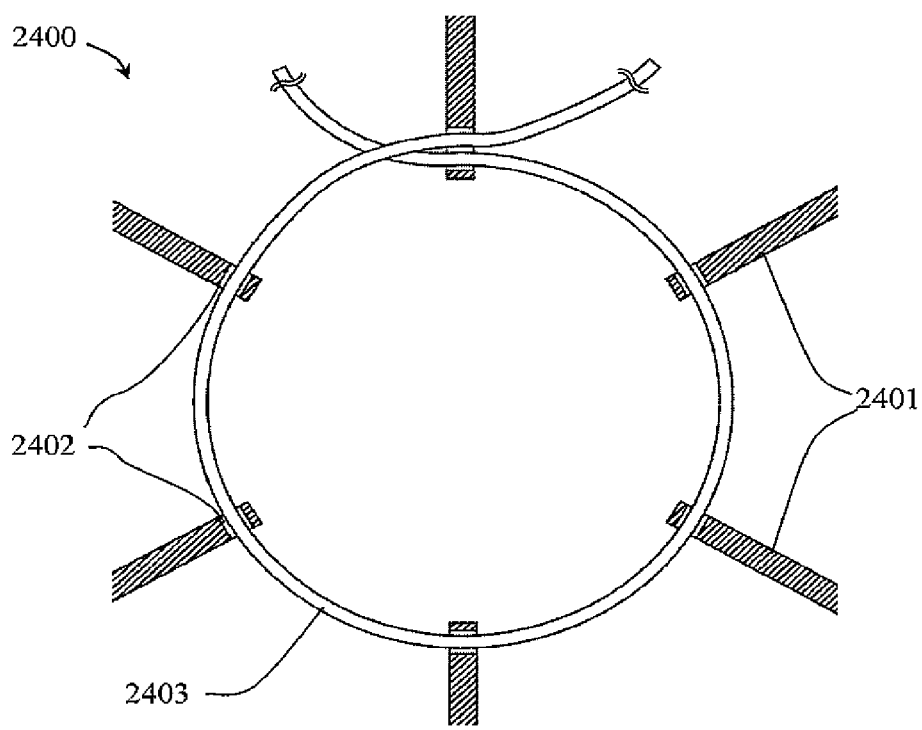
FIGS. 121 to 140 are end views showing filter apexes in which filter element ends are restrained by a holder comprising a filament which is trained in various manners through and/or around the filter element ends to restrain the filter elements while providing a small cross-sectional area facing blood flow, thereby reducing risk of fibrin growth at the apex.
Figure 122:
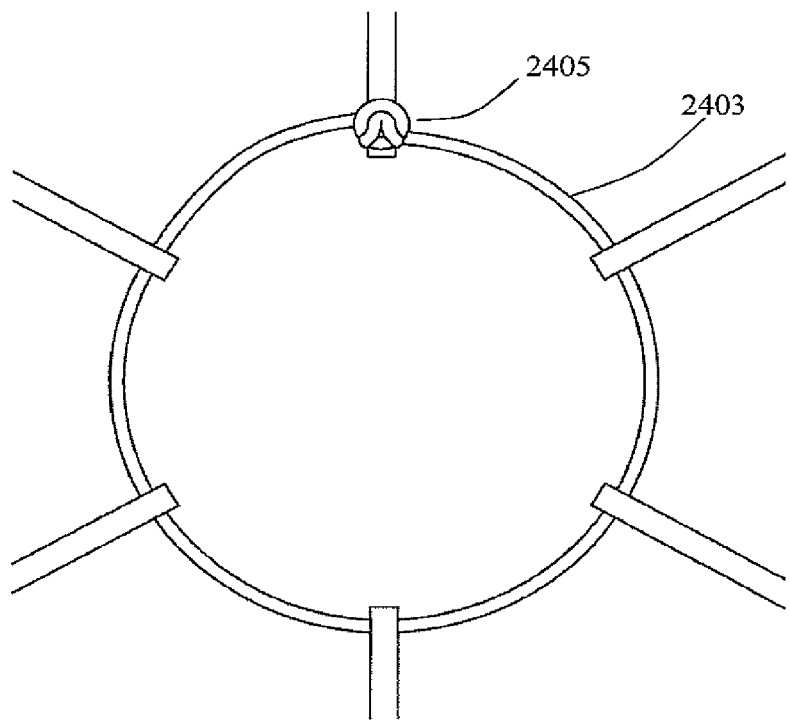
Figure 123:
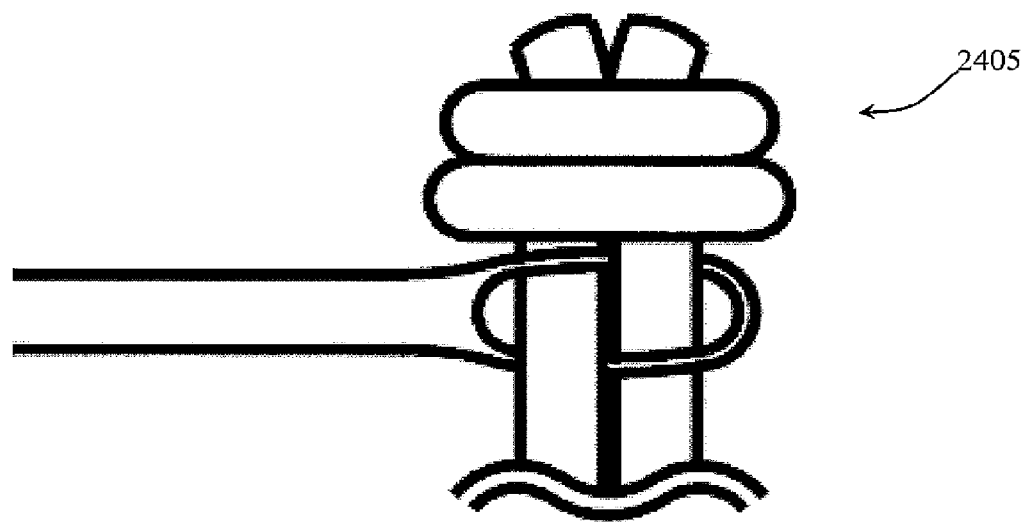

FIGS. 121 to 123 depict a filter apex (which may be central on the device longitudinal axis or not) 2400 formed by filter element ends 2401 having eyelets 2402. A holder is provided by a single-stranded filament 2403 which is trained through the eyelets 2402 and forms a single knot 2405 at one eyelet 2402. The holder thus holds in a restrained position the filter element ends 2401. The filament 2403 is threaded through one of the eyelets 2402 twice before tying a knot to close the loop—the knot used is preferably a stopper knot. FIG. 121 shows a cross sectional view before tying the knot while FIG. 122 shows the arrangement after tying the knot. FIG. 123 shows a side view of the knot 2405 and the eyelet 2402 to which it is tied.

Filter element eyelets through which a filament is threaded may be sized differently depending on how many times the filament is threaded through it. The eyelets may be in the form of holes which are machined or laser cut or etched in the side wall of the filter element ends. Alternatively, the eyelets may be applied in the radial direction provided the eyelets are twisted and shape set so that the array of eyelets are arranged in a manner that allows a filament to be threaded through in a circular fashion. However, untwisted filter element ends incorporating eyelets in the side wall may not obstruct blood flow to the same degree that twisted filter elements will due to the increased complexity of the twisted geometry.

Figure 124:
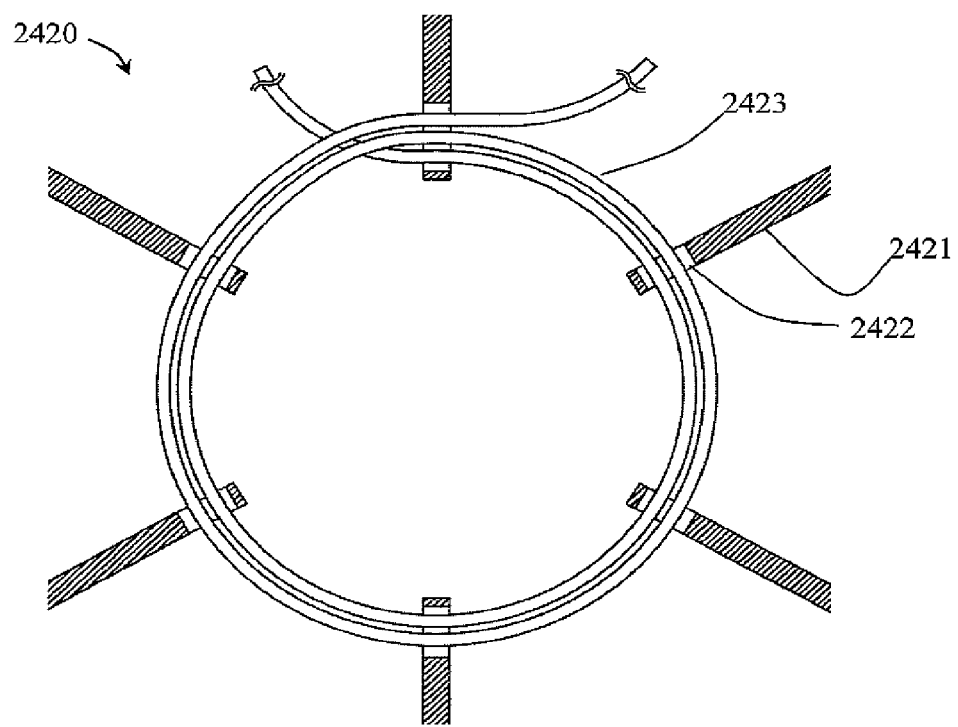
Figure 125:
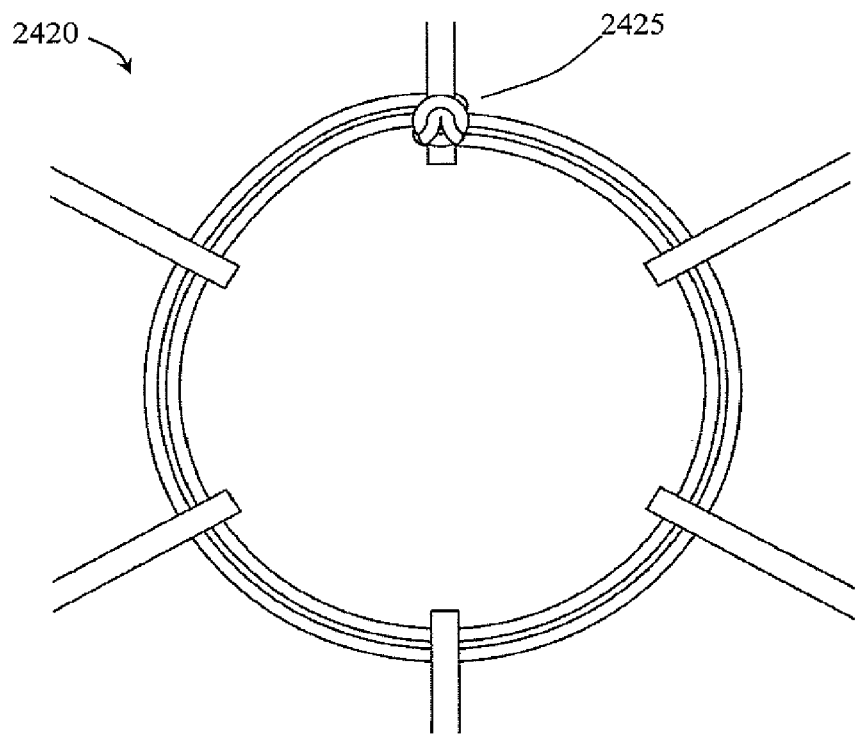
Figure 126:
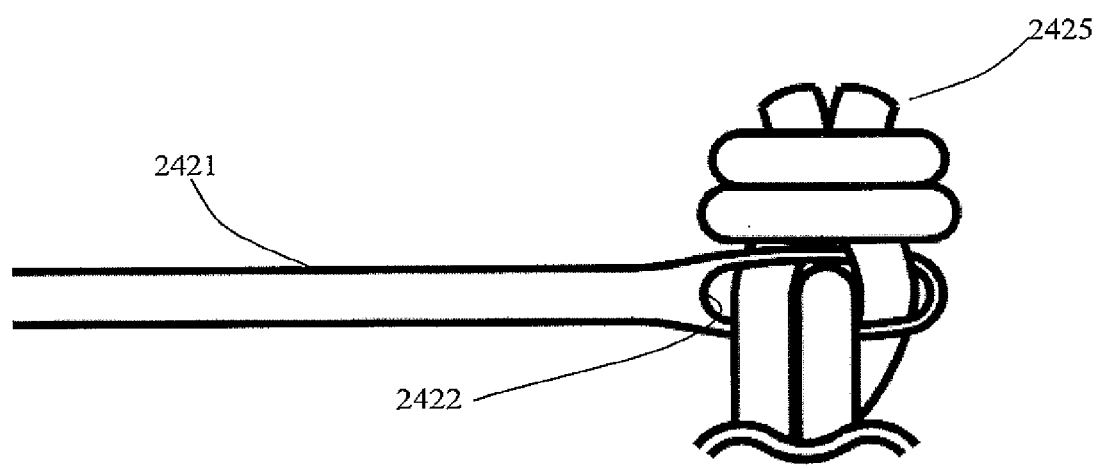

A filter apex 2420 depicted in FIG. 124 to FIG. 126 has a number of filter elements 2421 with openings 2422 facing circumferentially. A holder filament 2423 is threaded through one of the openings 2422 three times and twice through the remaining filter elements. The free ends of the filament 2423 are tied in a knot 2425 where the filament extends through a filter element opening 2422 three times. The knot used is preferably a stopper knot. FIG. 124 shows a cross sectional view before tying the knot while FIG. 125 shows the arrangement after tying the knot. FIG. 126 shows a side view of the filter element end where the knot is tied.

Figure 127:
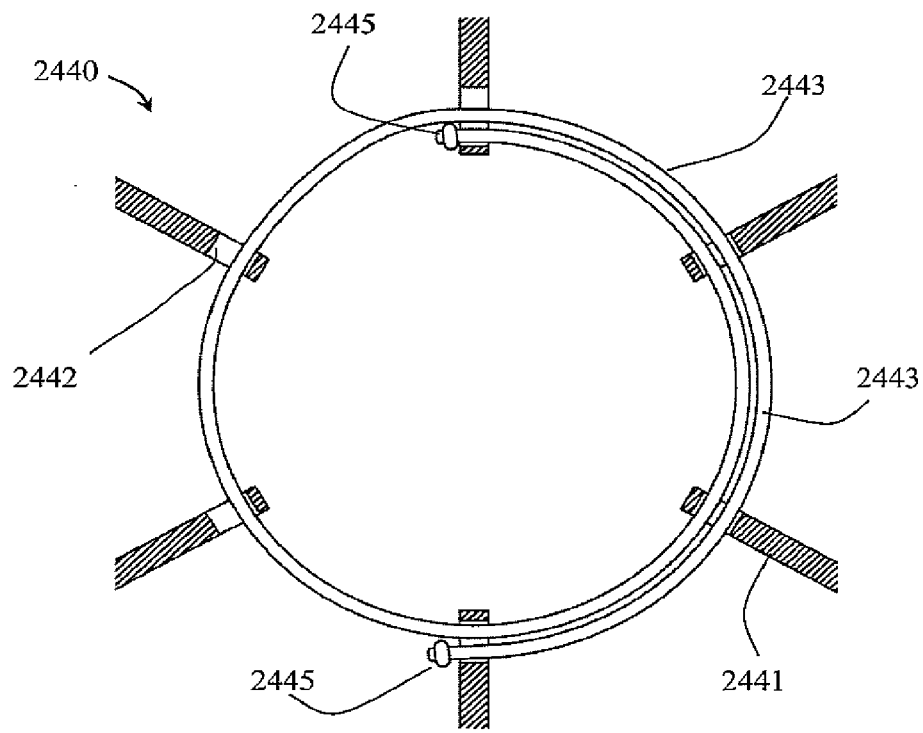

In another embodiment, shown in FIG. 127, a filter apex 2440 is formed by filter elements 2441 having eyelets 2442 and a holder filament 2443 with a double knot 2465. The filament 2443 extends through the eyelets 2442 at least once and each free end is tied in a knot 2445, preferably a stopper knot. This arrangement provides knots with a smaller surface area compared to that of a knot where two strands of filament are tied in a knot together. While there are more knots in this embodiment, the density of surface area obstructing blood flow is small.

Figure 128:
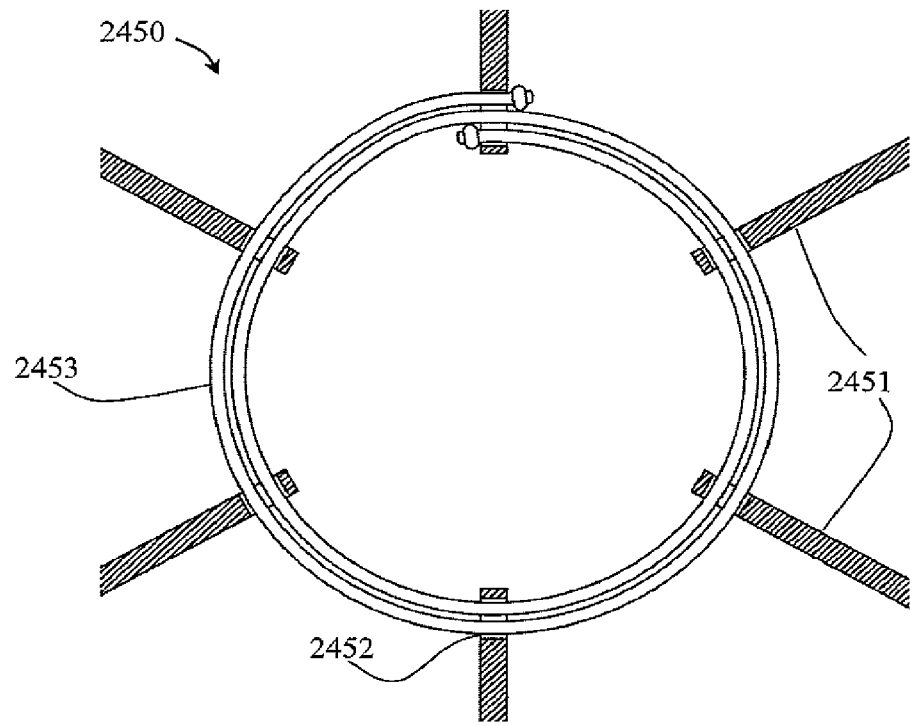

A number of arrangements may be envisaged using this approach, for instance, FIG. 128 shows a filter apex 2450 in which a filament 2453 extends through one filter element opening 2452 three times and twice through the remaining eyelets 2452. The ends of the filament 2453 are each individually tied adjacent a single eyelet 2452.

Figure 129:
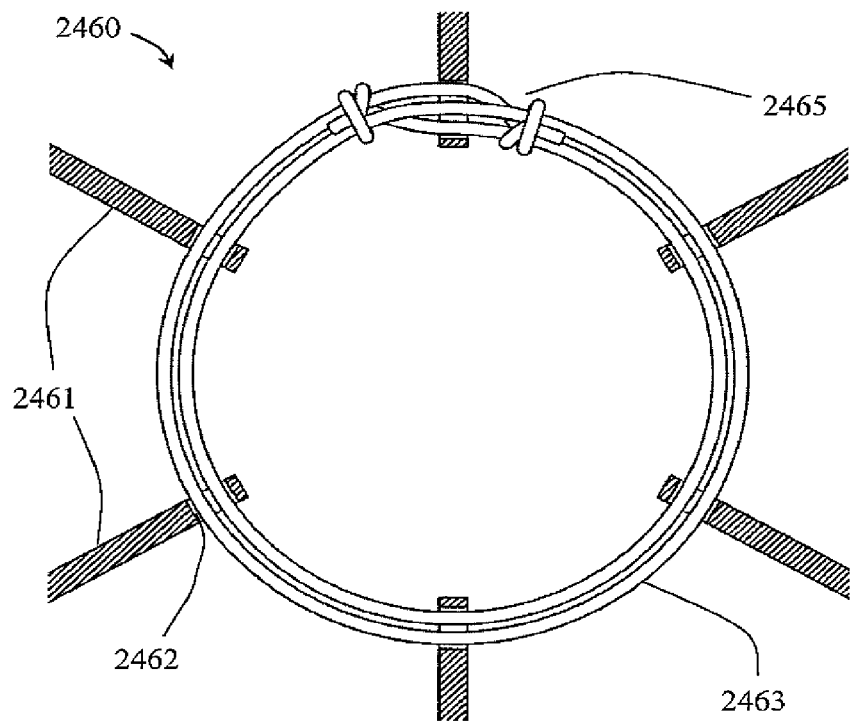

In another double knot embodiment, in a filter apex 2460 shown in FIG. 129 a knot 2465 is tied over the adjacent filament extending through filter element openings in a loop. This keeps the knot coupled to multiple filament loops to prevent it from extending into the blood flow providing a more streamlined profile.

Figure 130:
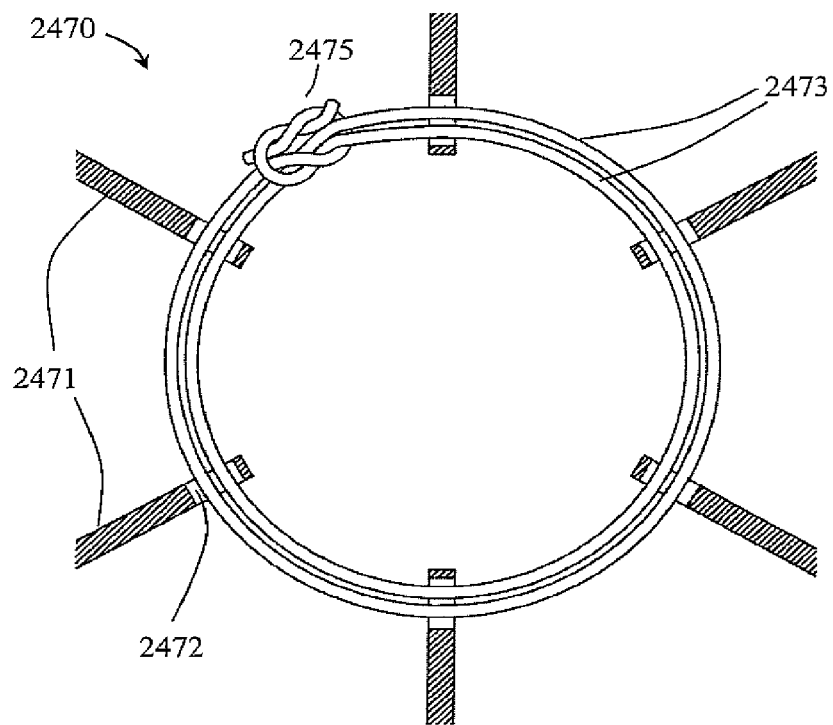

Referring to FIG. 130 a filter apex 2470 has filter element ends 2471 with eyelets 2472. A holder comprises a filament 2473 and a reef or surgical knot 2475 is tied by the filament ends and is located about mid-way between two eyelets 2472. The single-stranded filament 2473 extends through each of the filter element openings 2472 twice. However, it is possible to supply a single filament extending only once through each of the filter element openings—in this case a reef knot is applied directly with the two free filament ends. The reef knot provides a lower cross sectional area when compared to a stopper knot tied with two filament ends, thereby reducing obstruction to blood flow.

Figure 131:
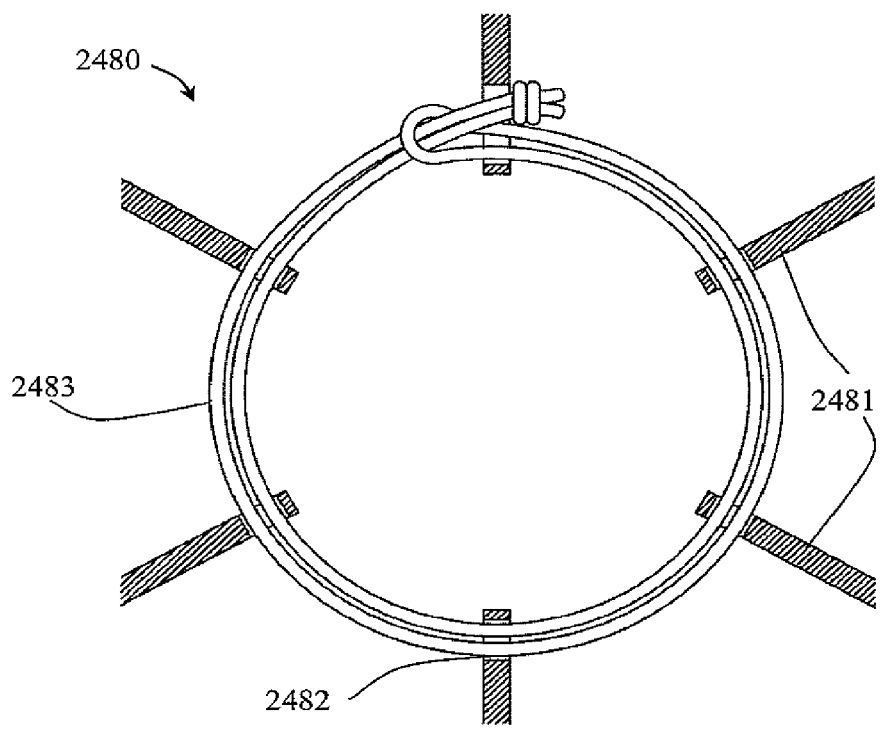

FIG. 131 depicts a filter apex 2480 formed by filter element ends 2481 with eyelets 2482 and a holder filament 2483 which forms a single knot extending through one filter element opening four times and the remaining filter element openings twice. The filament 2483 includes one loop beside the filter element 2481 with filament extending through four times and the two free ends of filament 2483 are tied on the other side of said filter element 2481. An alternative may include the two free ends of filament looping over said filter element and through the filament loop before tying a knot so that the filament loop and knot are on the same side of said filter element. In yet another embodiment, only one of the free ends of filament is looped over said filter element and through said filament loop before being tied in a knot with the other free filament end so that the knot is positioned on top of the filter element end.

Figure 132:
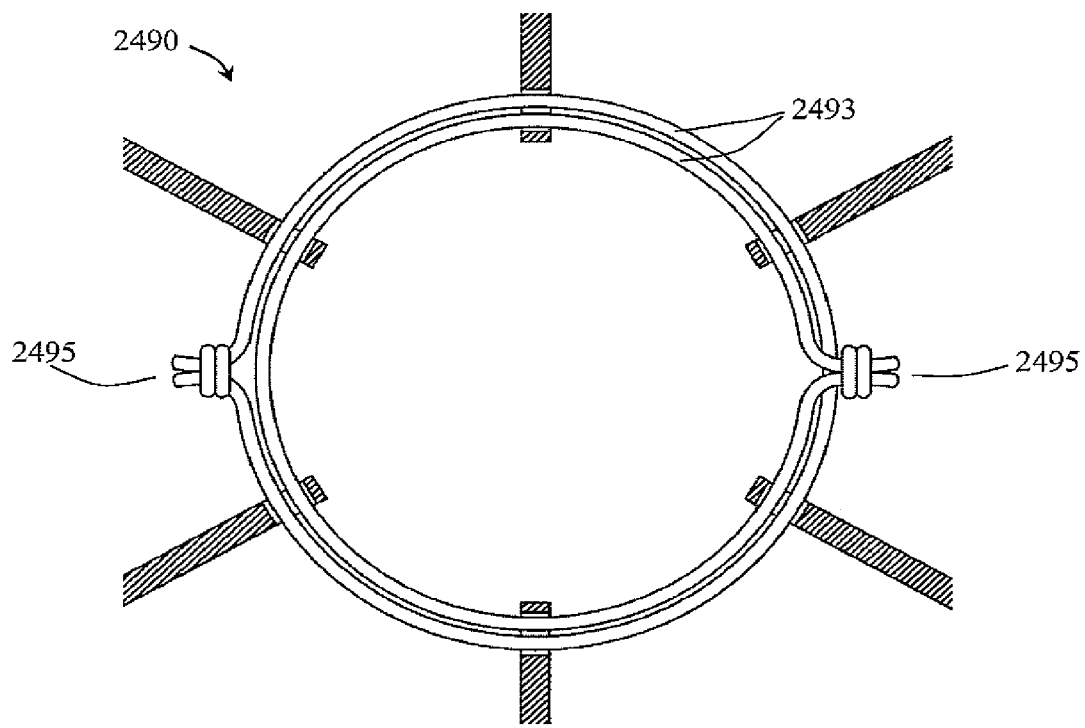

In another embodiment, shown in FIG. 132, in an apex 2490 two strands of filament 2493 are threaded through each of the filter element openings 2492 with knots 2495 tied opposite to one another. This provides a holder with a more distributed surface area density when compared to a holder including two strands of filament with 4 free ends tied together in a knot as described in FIG. 8e and FIG. 8f of our earlier application WO2010082187. Two strands of filament offer additional security should one of the strands inadvertently break prematurely, because one of the strands will always be tied slightly tighter than the other, the tighter strand will take the initial load and in the event of premature failure—the looser strand will become tensioned and keep the device in the filtering configuration until elapse of the predetermined protection period. Further, one of the loops may be inadvertently nicked or damaged during manufacturing, thus the secondary loop decreases the likelihood of a damaged filament leading to opening of the filter prematurely.

Figure 133:
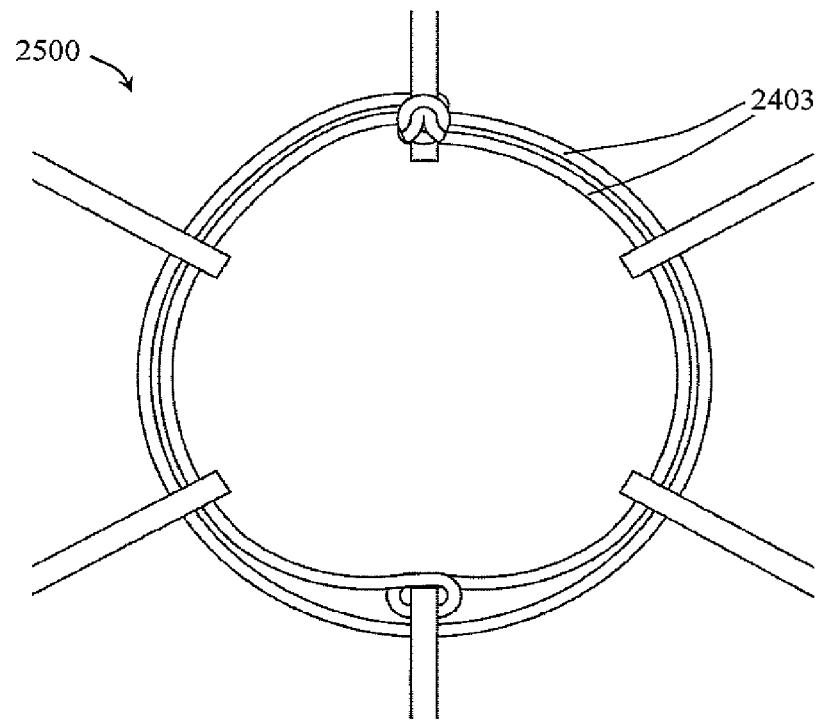

An embodiment in FIG. 133 depicts an apex 2500 having a holder with a single stranded filament threaded through one of the filter element ends three times, and the remaining filter element ends twice, wherein the two free ends of the filament are tied in a knot where the filament extends through one of the filter elements three times and wherein the filament loops around a filter element opposite to the one with the knot so that the filament changes from extending clockwise to counter clockwise or vice versa.

Figure 134:
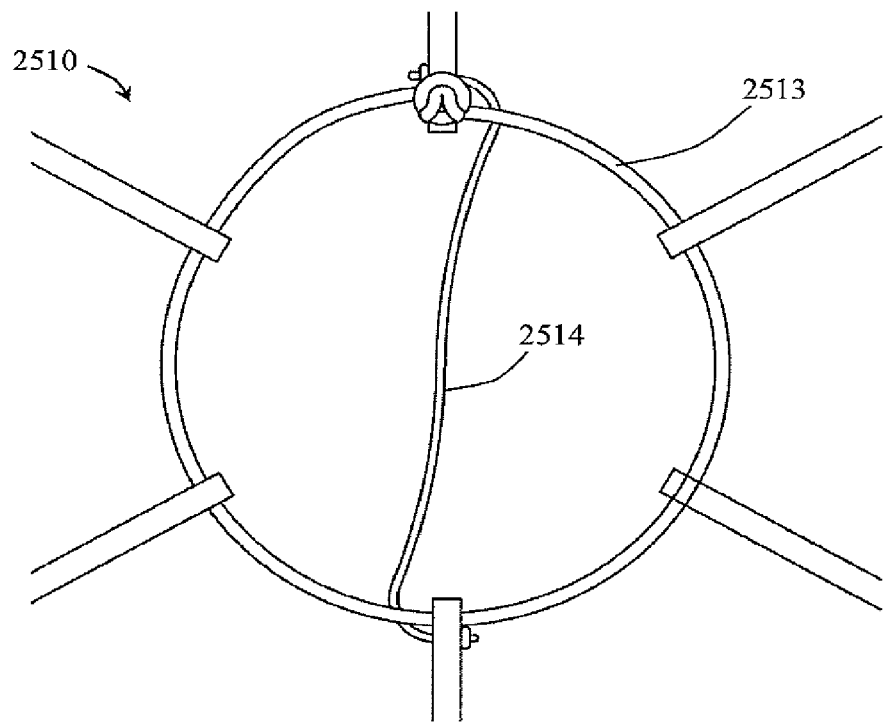

FIG. 134 depicts an apex 2510 including two filaments 2513 and 2514, one (2513) with a larger cross sectional area extending through each of the filter element openings once and twice though one where the free ends of the filament are tied together in a knot. The second filament (2514) with smaller cross sectional area extends diametrically through an opening in one filter element to another filter element directly opposite. A knot is tied at either end of the filament 2514 in order to secure it in place. The second filament 2514 serves to split the passage defined by the first filament 2513 extending in a hoop into two semi-circular shaped passages. This will increase the capture efficiency of the device in the case where more separation is provided between filter element ends. The smaller cross sectional area of the secondary filament 2514 reduces the likelihood of flow disturbances.

Figure 135:
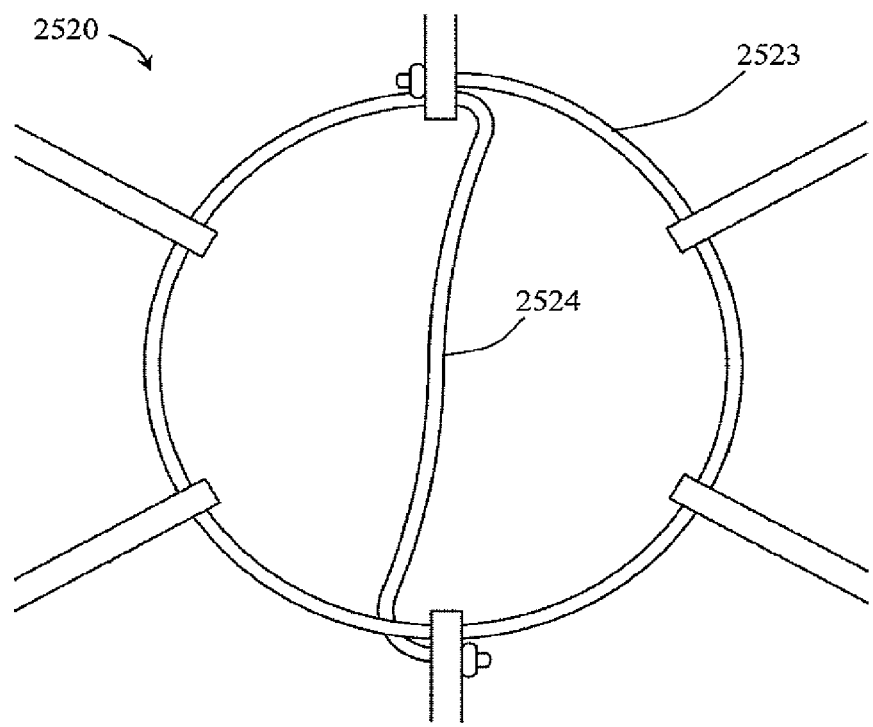

In another embodiment, a broadly similar holder is shown in FIG. 135 in which a single filament 2523 extends through two opposite filter element ends twice and through the remaining filter elements once. A segment 2524 of the same filament traverses across the lumen between the two filter elements that the filament extends through twice. A knot is tied at either end of the filament to secure in place.

Figure 136:
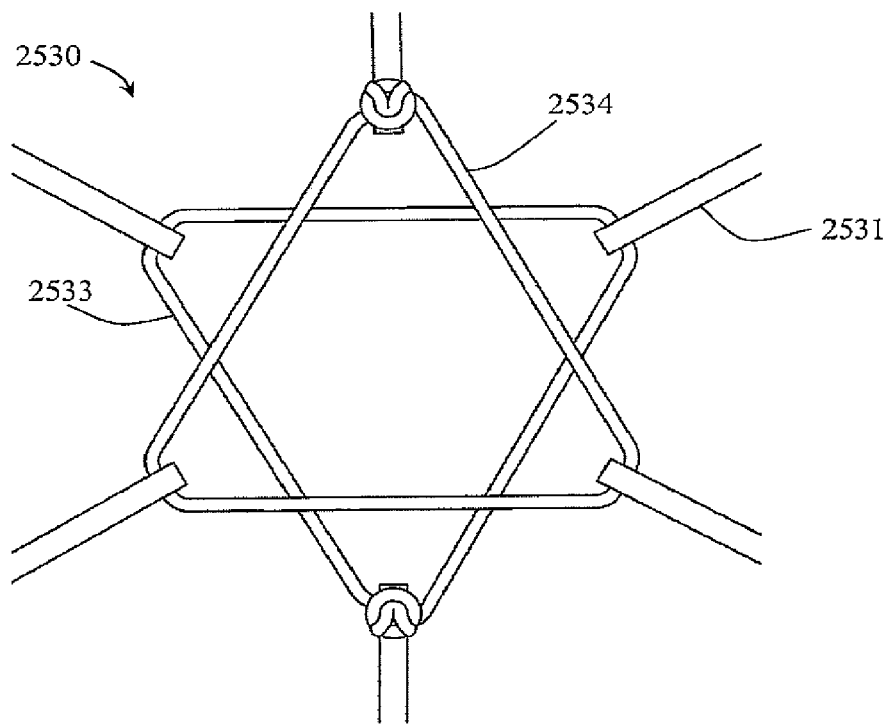

Referring to FIG. 136 a filter apex 2530 comprises two separate filaments 2533 and 2534 is shown in FIG. 136. Each filament extends twice through one filter element and once through two filter elements where six filter elements 2531 are supplied. The filter elements 2531 where the filaments extend through twice are opposite one another and are the location for tying a knot to secure in place. This arrangement provides two overlapping triangles forming a star shape. This holder offers increased separation while improving capture efficiency when compared to a device with a hoop-shaped arrangement with the same separation between filter element ends.

Figure 137:
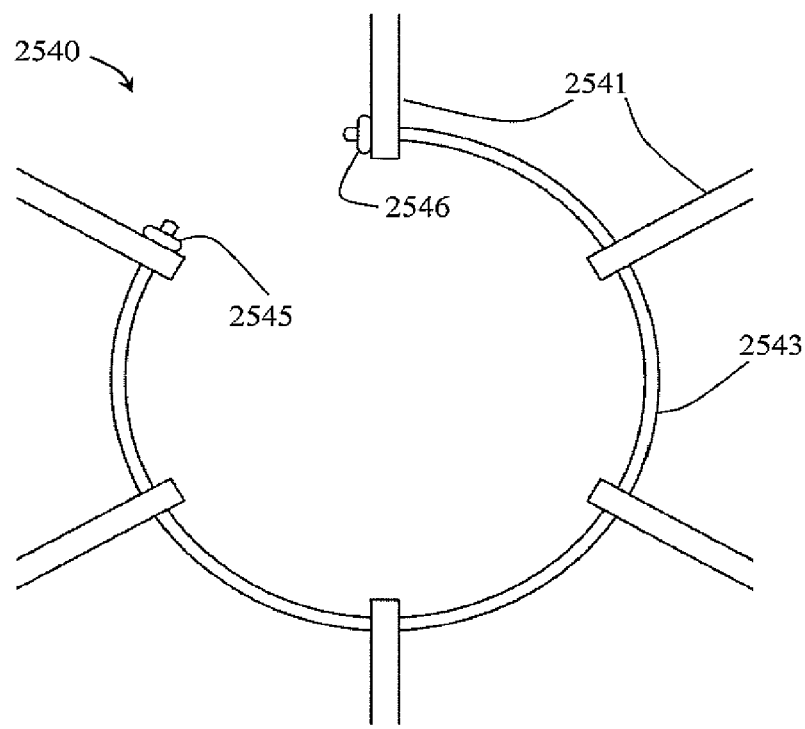

Depicted in FIG. 137 is an apex 2540 wherein a single filament 2543 extends through each of the filter element ends 2541 once and a knot 2545, 2546 is tied at either end of the filament 2543 and adjacent to one another. This provides a C-shaped holder with less material than if there was a complete hoop.

Figure 138:
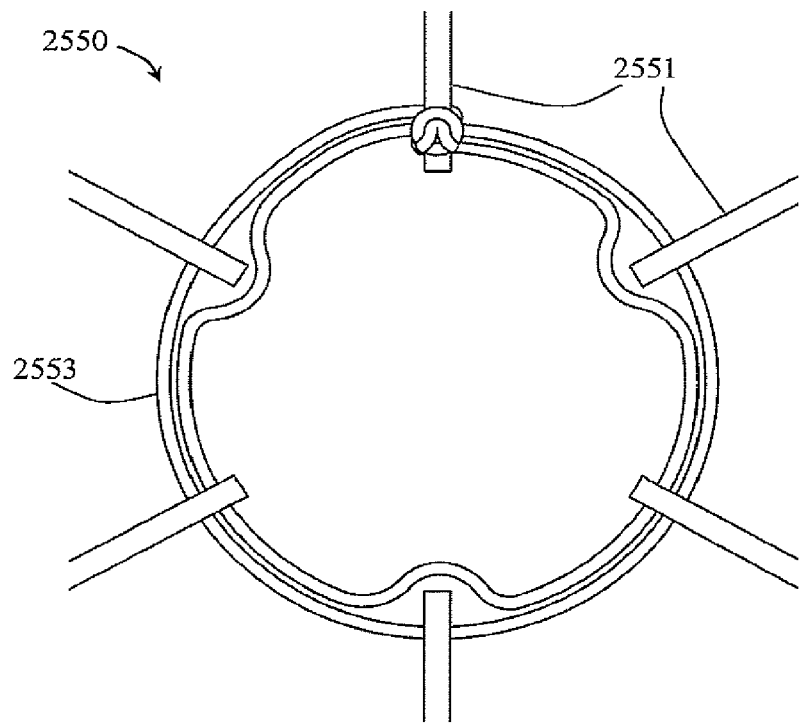

FIG. 138 illustrates an apex 2550 including a single filament 2553 extending through one filter element 2551 three times, two filter elements twice, and three filter elements once. It thus forms a hoop-shaped holder wherein a knot is tied onto the filter element that the filament extends through three times using the free ends of the filament 2553.

An apex 2560 with grouped filter element ends 2561 is shown in FIG. 139, wherein a single filament 2563 extends through one of the filter elements 2561 twice and only once through the remaining filter elements. A knot 2565 secures the filament 2563 to the filter element 2561 that the filament extends twice through and the filament extends from a set of grouped filter elements to a set of filter elements across, skipping the adjacent set of grouped filter elements providing a shamrock-shaped holder. This holder offers increased separation without the creation of a large central space when compared to hoop-shaped holders.

A further filter apex, 2570, is shown in FIG. 140. A single filament 2573 extends through each of a number of grouped filter element ends 2571 twice, and loops around each set of filter elements wherein one of the loops includes a knot 2575 to secure the filament 2573 in place. This arrangement provides a triangular-shaped holder in which six filter elements are supplied with grouped filter elements 2571.

The invention is not limited to the embodiments described but may be varied in construction and detail. For example the invention may be applied to devices having only a single proximal support hoop. The embodiments may be combined with teachings in our previous application U.S. 61/145,382 with embodiment for clot retention post conversion and, wherein, teachings in this application enhance the conversion step from filtering to non-filtering.

Any of the embodiments disclosed may be provided with biostable holder members to provide permanent filtration. Also, the filter apex may be central or off-centre with respect to the device longitudinal axis. Also, where the device has a holder engaging eyelets in the ends of the filter elements, the eyelet may be closed or it may be open with a small gap for insertion of the holder.

What is claimed:

1. A vascular filter device comprising:
a support for engaging a wall of a blood vessel;
a filter supported on the support and comprising a plurality of V-shaped or Y-shaped filter elements each filter element having two proximal segments connected to the support and a distal segment having a reception space at a distal end thereof configured to receive a biodegradable holder, the biodegradable holder configured to at least temporarily restrain the filter elements at a distal apex when the filter elements are across at least part of a cross-section of a blood vessel when in a filtering closed position;
wherein the distal segment extends radially outwardly at an angle to the two proximal segments; and
wherein at least one filter element extends radially outwardly with respect to a vascular filter device longitudinal axis when unconstrained.

2. A vascular filter device as claimed in claim 1, wherein at least one filter element extends in a curve with a concave portion facing radially outwardly in an unconstrained configuration.

3. A vascular filter device as claimed in claim 1, wherein a circumferential width of at least one filter element varies along its length.

4. A vascular filter device as claimed in claim 1, wherein the filter elements are configured to be held in the filtering closed position by the biodegradable holder.

5. A vascular filter device as claimed in claim 4, wherein the biodegradable holder is flexible such that it is slack when in a compressed delivery configuration and wherein the biodegradable holder is taut and forms a planar structure in the filtering closed position.

6. A vascular filter device as claimed in claim 1, wherein the two proximal segments with a length of less than 10 mm and the distal segment are configured, to be temporarily restrained in a filtering closed position across at least part of a cross-section of a blood vessel;
said at least one filter element extends radially outwardly when unconstrained, further said at least one filter element is configured so that the two proximal segments have an angle with respect to the longitudinal axis of between 45° radially inwardly and 45° radially outwardly, the support and at least one filter element are configured so that the filter element has at its distal segment a radial outward force in a range of 0.1 N to 1.0 N where the vascular filter device has an unconstrained diameter in a range of 20 mm to 40 mm.

7. A vascular filter device as claimed in claim 1, wherein at least one filter element extends radially outwardly in a non-planar path.

8. A vascular filter device comprising:
a support for engaging a wall of a blood vessel;
a filter supported on the support and comprising a plurality of V-shaped or Y-shaped filter elements each filter element having two proximal segments connected to the support and a distal segment having a reception space at a distal end configured to receive a biodegradable holder, the biodegradable holder configured to at least temporarily restrain the filter elements at a distal apex when the filter elements are across at least part of a cross-section of the blood vessel when in a filtering closed position, and
wherein at least one filter element extends radially outwardly from the support with respect to a vascular filter device longitudinal axis when unconstrained,
wherein with respect to the longitudinal axis, the two proximal segments extends at an angle of between 45° radially inwardly and 45° radially outwardly, wherein the distal segment extends radially outwardly at an angle to the two proximal segments, and wherein a two proximal segments length is less than 10 mm, and
wherein when unconstrained, the distal segment extends radially outwardly from the two proximal segments at an angle of between 5° and 60°.

9. A vascular filter device as claimed in claim 8, wherein the two proximal segments have a length of less than 7 mm.

10. A vascular filter device as claimed in claim 9, wherein a distal segment length is in a range of 15 mm to 30 mm.

11. A vascular filter device as claimed in claim 8, wherein a distal segment length is in a range of 10 mm to 40 mm.

12. A vascular filter device as claimed in claim 8, wherein when unconstrained, the distal segment extends radially outwardly at an angle of between 10° and 45° relative to the longitudinal axis of the vascular filter device.

13. A vascular filter device as claimed in claim 8, wherein a circumferential width of the filter element varies along its length.

14. A vascular filter device as claimed in claim 8, wherein the filter elements are held in the filtering closed position by a biodegradable holder.

15. A vascular filter device as claimed in claim 8, wherein the biodegradable holder is flexible and configured to be slack when in a compressed delivery configuration and wherein the biodegradable holder is configured to be taut and to form a planar structure in the filtering closed position.

16. A vascular filter device as claimed in claim 8, wherein the distal segment extends radially outwardly at an angle to the two proximal segments.

* * * * *